(12) United States Patent
Sluyterman van Langeweyde et al.

(10) Patent No.: US 9,352,415 B2
(45) Date of Patent: May 31, 2016

(54) METHOD FOR GENERATING AN ABLATION PROGRAM, METHOD FOR ABLATING A BODY AND MEANS FOR CARRYING OUT SAID METHOD

(75) Inventors: Georg Sluyterman van Langeweyde, Jena (DE); Jesús-Miguel Cabeza-Guillén, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 1531 days.

(21) Appl. No.: 11/884,379

(22) PCT Filed: Feb. 15, 2006

(86) PCT No.: PCT/EP2006/001364
§ 371 (c)(1),
(2), (4) Date: Aug. 15, 2007

(87) PCT Pub. No.: WO2006/087180
PCT Pub. Date: Aug. 24, 2006

(65) Prior Publication Data
US 2008/0058781 A1   Mar. 6, 2008

(30) Foreign Application Priority Data

Feb. 15, 2005  (DE) .......................... 10 2005 006 897
Mar. 22, 2005  (DE) .......................... 10 2005 013 252

(51) Int. Cl.
*A61B 18/20*      (2006.01)
*B23K 26/073*     (2006.01)
(Continued)

(52) U.S. Cl.
CPC ........... *B23K 26/073* (2013.01); *A61F 9/00806* (2013.01); *B23K 26/03* (2013.01); *B23K 26/032* (2013.01); *B23K 26/034* (2013.01); *B23K 26/0622* (2015.10); *B23K 26/402* (2013.01); *A61F 9/008* (2013.01);
(Continued)

(58) Field of Classification Search
USPC ......................................... 128/898; 606/3–12
See application file for complete search history.

(56) References Cited

U.S. PATENT DOCUMENTS 5,186,184 A    2/1993  Aindow et al.
5,348,551 A *  9/1994  Spears et al. ..................... 606/5
(Continued)

FOREIGN PATENT DOCUMENTS

DE   41 37 646 A1   5/1993
DE   196 23 749 A1  5/1997
(Continued)

OTHER PUBLICATIONS

Seiler, Theo, et al., "Refraktive Chirurgie der Hornhaut," Edition 1, ENKE in the Georg Thieme Verlag, Stuttgart/New York, 2000 (ISBN 3-13-118071-4), Chapter 6.1, pp. 150-196.
(Continued)

*Primary Examiner* — William Thomson
*Assistant Examiner* — Jeffrey Lipitz
(74) *Attorney, Agent, or Firm* — Patterson Thuente Pedersen, P.A.

(57) ABSTRACT

In a method for generating an ablation program for ablation of material from a surface of a body according to a predetermined desired ablation profile by emission of pulses of a pulsed laser beam onto the surface, the ablation program is generated from the desired ablation profile as a function of the shape of a beam profile of the laser beam and of an inclination of the surface to be ablated and/or considering a water content of the material to be ablated.

30 Claims, 17 Drawing Sheets

(51) Int. Cl.
*B23K 26/03* (2006.01)
*B23K 26/40* (2014.01)
*A61F 9/008* (2006.01)

(52) U.S. Cl.
CPC .......... *A61F 2009/0088* (2013.01); *A61F 2009/00872* (2013.01); *A61F 2009/00882* (2013.01); *B23K 2203/30* (2015.10)

(56) References Cited

U.S. PATENT DOCUMENTS

| | | | |
|---|---|---|---|
| 5,624,437 A * | 4/1997 | Freeman et al. | 606/12 |
| 5,642,287 A | 6/1997 | Sotiropoulos et al. | |
| 5,843,070 A | 12/1998 | Cambier et al. | |
| 5,993,441 A | 11/1999 | Muller et al. | |
| 6,056,740 A | 5/2000 | Shimmick | |
| 6,210,401 B1 * | 4/2001 | Lai | 606/12 |
| 6,261,220 B1 | 7/2001 | Frey et al. | |
| 6,290,695 B1 | 9/2001 | Kuhnert et al. | |
| 6,293,938 B1 | 9/2001 | Muller et al. | |
| 6,421,652 B2 | 7/2002 | Loeb et al. | |
| 6,497,701 B2 | 12/2002 | Shimmick et al. | |
| 6,559,934 B1 | 5/2003 | Yee et al. | |
| 6,569,154 B2 | 5/2003 | Campin et al. | |
| 6,572,606 B2 * | 6/2003 | Kliewer et al. | 606/5 |
| 6,592,574 B1 | 7/2003 | Shimmick et al. | |
| 6,666,855 B2 | 12/2003 | Yee et al. | |
| 6,694,173 B1 | 2/2004 | Bende et al. | |
| 6,706,036 B2 * | 3/2004 | Lai | 606/12 |
| 6,755,819 B1 * | 6/2004 | Waelti | 606/5 |
| 6,848,790 B1 | 2/2005 | Dick et al. | |
| 6,887,231 B2 * | 5/2005 | Mrochen et al. | 606/5 |
| 7,044,944 B2 | 5/2006 | Campin et al. | |
| 7,128,737 B1 | 10/2006 | Goder et al. | |
| 2001/0010003 A1 * | 7/2001 | Lai | 606/107 |
| 2003/0105457 A1 | 6/2003 | Mrochen et al. | |
| 2003/0153904 A1 | 8/2003 | Patel | |
| 2003/0208190 A1 * | 11/2003 | Roberts et al. | 606/5 |
| 2004/0019346 A1 * | 1/2004 | Chernyak | 606/5 |
| 2004/0059398 A1 * | 3/2004 | Yee et al. | 607/89 |
| 2004/0172013 A1 | 9/2004 | Sumiya | |
| 2004/0236392 A1 | 11/2004 | Dick et al. | |
| 2005/0107775 A1 | 5/2005 | Huang et al. | |
| 2005/0171515 A1 * | 8/2005 | Chernyak | 606/5 |

FOREIGN PATENT DOCUMENTS

| | | |
|---|---|---|
| WO | WO 01/50945 A2 | 7/2001 |
| WO | WO 01/67978 A1 | 9/2001 |
| WO | WO 01/85075 A1 | 11/2001 |
| WO | WO 2005/011544 A1 | 2/2005 |

OTHER PUBLICATIONS

Srinivasan, R., "Ablation of Polymers and Biological Tissue by Ultraviolet Lasers," *Science*, vol. 234, Oct. 31, 1986, pp. 559-565,.

Fisher, Brian T., et al., "Assessment of Transient Changes in Corneal Hydration Using Confocal Raman Spectroscopy," *Cornea*, vol. 22(4), 2003, pp. 363-370.

Mark H. Feldman et al., "The effect of water content on the 193 nm excimer laser ablation", *Clinical and Experimental Ophthalmology*, 2002, pp. 99-103.

* cited by examiner

METHOD FOR GENERATING AN ABLATION PROGRAM, METHOD FOR ABLATING A BODY AND MEANS FOR CARRYING OUT SAID METHOD

BACKGROUND OF THE INVENTION

The present invention relates to a method for generating an ablation program for ablation of material from a surface of a body according to a predetermined desired ablation profile by emitting pulses of a pulsed laser beam onto said surface, to a method for ablating material from a surface of a body according to a predetermined desired ablation profile, to a method for forming control signals to control a laser ablation device for ablating material from a surface of a body according to a predetermined desired ablation profile by means of pulses of a pulsed laser beam emitted by the laser ablation device, and to means for carrying out these methods.

The ablation, i.e. removal, of material from a surface of a body by means of a pulsed laser beam is basically known. During ablation, laser radiation or a laser beam is directed onto the surface to be ablated, where material of the body absorbs at least part of the laser radiation and, if the intensity or the input of energy is sufficient, material is removed from the surface. Therefore, laser ablation can be employed to shape a body in a non-contacting manner, with high precision, in particular even with only small depths of removal.

Various laser ablation methods are known for shaping.

In a variant which is suitable for ablation of a body that is approximately spherical in the region of ablation, laser beam pulses are directed onto the surface, with the target location onto which the respective pulse is to be directed as well as the shape and size of the beam cross-section on the surface being set according to a predetermined ablation program. In many cases, the target location is constant for all pulses and is then not explicitly defined.

In another, particularly important variant, also referred to as "spot scanning" method, material is removed from the surface by guiding a pulsed laser beam over the surface according to a predetermined ablation program. The ablation program is then understood to be a series of target locations on the surface or of corresponding data representing the positions of the target locations onto which at least one pulse of the laser beam is to be respectively directed. If the beam or pulse properties of the used laser radiation are variable, the ablation program can further include at least one indication of a beam or pulse property, particularly defining the energy of the pulse or the fluence, i.e. the energy of the pulse in relation to the irradiated area on a plane which is orthogonal to the direction of the laser beam on the surface of the body. If the laser is working at a constant pulse energy or fluence during ablation, there is no need to provide data representing the pulse energy or fluence for each pulse or target location.

The ablation program is determined on the basis of a predetermined desired ablation profile, i.e. of the definition of desired depths of ablation or depths of removal of the material to be ablated by the pulses as a function of the location on the surface. When generating the ablation program, it is often assumed that each pulse ablates a single-pulse ablation volume which is given by the cross-section of the laser beam at the surface, assumed to be orthogonal to the direction of the beam for this purpose, and by the ablation depth. If several pulses impinge at the same location, the depths of ablation add up so that a greater total depth is achieved. The ablation program is then determined such that by emission of the pulses respective ablation volumes or single-pulse volumes are removed from the surface at the target locations given by the ablation program, so that, on the whole, the desired ablation profile is achieved in the best possible way.

An important field of application of laser ablation according to the so-called "spot scanning" method is the laser ablation of plastic lenses, e.g. contact lenses, or particularly also of corneal tissue in photo-refractive keratectomy or LASIK for correction of defective vision, in particular in the human eye.

In order to obtain as precisely as possible the ablation profile to be achieved, i.e. the desired ablation profile, it is essential that the ablation effect of an individual pulse be well-known when generating the ablation program.

As already mentioned, the process of ablation is determined by the energy per surface area impinging on the surface to be processed or by the effective fluence, in which case, typically, ablation actually occurs only above a material-dependent threshold value for the energy per surface area.

In the case of surfaces which are inclined with respect to the laser beam impinging on them, it has been observed that ablation is less deep than would be expected in the case of orthogonal impingement. This can be explained partially by the fact that the spot produced by the laser beam on the surface has a greater surface area due to the inclination than in the case of perpendicular impingement, whereby the actual fluence on the surface is reduced with respect to the fluence in the case of perpendicular impingement.

WO 01/85075 A1 describes a method for generating a control program according to which a laser spot is passed in a spatially and temporally controlled manner over a cornea that is to be photo-refractively corrected in order to ablate a predetermined desired ablation profile from the cornea. When generating the control program, the influence of the angle between the laser beam and the surface of the cornea on the energy density of the laser spot impinging on the surface of the cornea and/or of that portion of the laser beam energy impinging on the surface of the cornea which is reflected away from the surface is taken into consideration.

WO 01/87201 A1 describes a system for the correction of optical errors in an eye, said system comprising a wavefront analyzer which responds to a wavefront coming from the eye, thereby determining an optical path difference between a reference wave and said wavefront. A converter provides an optical correction on the basis of the path difference and a radially dependent function of ablation efficiency. The correction of ablation efficiency uses a compensating polynomial of the form $A+B\rho+C\rho^2+D\rho^3+ \ldots +X\rho^n$, wherein $\rho$ designates a standardized radius which is measured from a central region of the cornea and takes a value of 1 at the outer edge of the region to be corrected. The coefficients of the polynomial are determined by comparing the desired ablation depth with the achieved ablation depth, i.e. by experimentation.

However, the two methods just mentioned leave sufficient space for an improvement in accuracy of the ablation by using an improved ablation program.

When treating defective vision in the human eye by ablation using an excimer laser, the cornea of the eye is shaped such by ablation that a refractive error which causes said defective vision is removed to the largest possible extent. Using conventional methods, the desired refraction can be achieved in approximately 95% of cases with an accuracy of approximately +/−1 diopter.

However, in individual cases there may be problems with night vision and a reduction in contrast sensitivity of twilight vision, which are due to changes in the asphericity of the cornea by the laser surgical treatment. In a healthy eye or an eye which does not have defective vision, the cornea is somewhat prolate and has a negative asphericity with values for the asphericity parameter Q of approximately −0.25. This asphericity compensates for spherical aberrations in the lens of the eye. After laser surgical treatment of near-sightedness, the cornea tends to be somewhat flattened, with the asphericity being substantially greater than in the healthy eye or the eye not having defective vision. These deviations may be at least partially due to the fact that the actual ablation profile achieved by ablation differs from the predetermined desired ablation profile.

For improved ablation, WO 95/27534 describes a method and a system for carrying out photo-refractive keratectomy so as to produce a desired refractive correction in the corneal tissue. Said method and system use control of the effect of liquid on the surface of the cornea in order to reduce the interfering influence of the liquid on the desired ablation process while maintaining the water content of the cornea. It is suggested to control the mean repetition frequency of pulses emitted onto the cornea's surface, so as to reduce an accumulation of liquid between pulses, without dehydrating the cornea, or to select an increased fluence for the pulse emitted onto the cornea's surface so as to reduce the effect of liquid accumulated on the cornea's surface. It is further suggested that, before a pulse intended for ablation is emitted to a site, evaporation energy should be supplied to the latter.

These known methods also still leave room for improving the accuracy of ablation by the use of an improved ablation program.

SUMMARY OF THE INVENTION

Therefore, it is an object of a first aspect of the present invention to provide a method for generating an ablation program, which allows high-precision ablation, and means for carrying out said method. A further object consists in providing a corresponding method for ablating material from a surface of a body, said method allowing high precision of ablation, and means for carrying out said method of ablation.

According to the first aspect of the invention, said object is achieved by a first method for generating an ablation program, namely a method for generating an ablation program for ablation of material from a surface of a body according to a predetermined desired ablation profile by the emission of pulses of a pulsed laser beam onto the surface, wherein the ablation program is generated from the desired ablation profile as a function of the shape of a beam profile of the laser beam and of an inclination of the surface to be ablated.

An ablation program, in particular the ablation program generated by means of the first generating method of the invention and to be used for ablation, is understood to be—as described above—at least one definition of a sequence of target locations or target directions onto or in which the pulses of the laser beam are emitted. In addition, the ablation program can either contain or predetermine either one value of pulse energy or of fluence for the entire sequence or, for each pulse or group of pulses, one value each of the pulse energy or fluence to be used for the pulse or group of pulses. In the second case, the values may depend on the target location. In this case, the ablation profile is understood to be an indication of the ablation depth as a function of the location on the surface or of a direction of the laser beam with respect to the body. Thus, said profile may be a desired, theoretical or actual profile.

The method considers the inclination of the surface, i.e. the inclination of the surface relative to the direction of the laser beam on the surface or relative to a fixed reference direction. The reference direction may be, for example, a direction given by a predetermined central direction of the laser beam from which the laser beam is deflected only at very small angles in order to reach different target locations on the surface of the body. The inclination of the surface of the body is generally position-dependent and is preferably considered, at least by approximation, for each pulse in a manner depending on the position of the target location of the pulse.

The invention or the described aspect of the invention is based on the concept, among others, that the energy per surface area actually effective for ablation, i.e. the effective fluence, of a pulse of the pulsed laser beam impinging on the surface of the body depends not only on the surface's inclination relative to the direction of the laser beam at the surface, but also on the beam profile of the laser beam, in particular at the surface of the body. The beam profile is understood to be the course of the intensity or of the surface area-related energy or fluence of the pulse over the beam cross-section near the surface. The shape of the beam profile does not include any absolute values of intensity or energy or of the fluence relating to a cross-sectional area which is perpendicular to the laser beam, but merely includes the run of these quantities. Therefore, the method is suitable, in particular, for ablation with laser beams having a non-constant beam profile.

In the following, fluence is understood to be the energy of the laser radiation with respect to a surface area orthogonal to the direction of the laser beam. This should be distinguished from the fluence effective for ablation, which shall be referred to hereinafter as effective fluence and designates the energy per surface area of the surface which may be inclined. The effective fluence is identical with the fluence only when the direction of the laser beam is orthogonal to the surface. The fluence of a pulse is understood to be the value at a given point, preferably the center, of the beam profile. Since the beam shape is assumed to be known, this indication suffices to specify the beam profile.

In many cases, ablation only takes place if the effective fluence locally exceeds a material-dependent threshold value of the fluence for material removal. Portions of the beam profile with values for the effective fluence that are below this threshold value do not lead to ablation, so that the actual ablation by a pulse may differ significantly from the ablation assumed in known methods for generating an ablation program. Consideration of only the inclination of the surface relative to the laser beam and a corresponding magnification of the spot generated by the laser beam on the surface, does not take this effect into consideration and would therefore lead to an inaccurate prediction of the ablation volume ablated by one single pulse. Therefore, the consideration of the ablation's dependence on the beam profile is advantageous, particularly when using laser beams whose fluence is below the material-dependent threshold fluence value in some regions of the beam cross-section. Thus, by simultaneous consideration of the inclination to the surface to be ablated and of the shape of the beam profile, an ablation program to be used for ablation can be generated, which, in the case of an ablation according to said ablation program, leads to an ablation profile that comes very close to the desired ablation profile to be achieved or is ideally identical therewith.

Of course, the ablation program may also depend on further variables, e.g. further beam parameters, such as the beam diameter at the surface of the body, the threshold fluence value at which ablation begins, and further variables.

The generating method for generating an ablation program can be carried out according to the first aspect of the invention by means of a first generating device. The device for generating an ablation program for ablation of material from a surface according to a desired ablation profile by emitting pulses of a pulsed laser beam onto the surface comprises a data processing device which is provided to carry out the first generating method according to the invention.

In particular, the data processing device may comprise a processor for execution of a computer program by means of which the ablation program can be generated according to the first generating method of the invention, if the computer program is executed on the computer, as well as a memory in which the program is stored.

The desired ablation profile may be represented in any desired manner. For example, it may be given by points on a predetermined point grid in a reference planes and by definitions of the ablation depth which are respectively assigned to said points. However, it is also possible to define the desired ablation profile parameterized by at least one functional parameter and a value of the functional parameter, the function and the value of the functional parameter being selected such that the function defines the ablation depth depending on the functional parameter's value and on the location in the reference plane. In the case of a function-related representation, polynomials, splines, Zernike polynomials or other representations may be used, for example.

The surface data required to generate the ablation program and from which the inclination can be directly determined allow to directly define the surface inclination as a function of the location, the gradients of the surface level above a predetermined reference plane in which the locations are indicated, or even the levels of the surface above the reference plane as a function of the location, particularly allowing to use also the possibilities of representation mentioned with respect to the desired ablation profile. If these data do not explicitly contain the inclination, e.g. given as corresponding angles, this information can be simply determined by gradient formation and/or the use of trigonometric relationships.

Depending on the application, the desired ablation profile and/or the data relating to the surface inclination can be stored in the data processing device, which is particularly convenient if several identical bodies are to be ablated one after the other. If different desired ablation profiles are respectively used for different ablations, the data processing device may comprise an interface for determining the desired ablation profile, which interface may be provided by corresponding circuits and/or by a software interface. The desired ablation profile can then be input or read in via the interface, for example.

Although the surface data may change with respect to the inclination of the surface, the first generating device according to the invention may further comprise an interface for determining surface data which directly or indirectly represent the inclination of the surface. The interface may be provided in the same manner as the interface for determining the desired ablation profile.

The further object of providing an ablation method is achieved by a first method of ablation, namely a method for ablating material from a surface of a body according to a predetermined desired ablation profile by means of a pulsed laser beam, which is guided over the surface and has a predetermined beam profile shape, wherein an ablation program is generated by the first generating method according to the invention, and pulses of the laser beam are directed onto the surface according to the generated ablation program.

The pulses may preferably be emitted periodically, although this need not necessarily be the case.

Moreover, the object is achieved by a first device for ablation, namely a device for ablation of material from a surface of a body which comprises a laser emitting a pulsed laser beam, a deflecting device for controlled deflection of the laser beam, and a generating device according to the invention.

In addition to the first generating device according to the invention, the first ablation device of the invention comprises a laser suitable for ablation and a deflecting device by means of which a laser beam emitted by the laser can be directed onto the surface to be ablated. The deflecting device and the laser are controllable as a function of the ablation program generated by the first generating device so that pulses of the pulsed laser beam emitted by the laser are directed onto corresponding target locations on the surface.

In order to control the deflecting device and/or the laser, the first generating device may preferably comprise a control unit for controlling a laser to emit the laser beam and/or a deflecting device for deflecting the laser beam according to a generated ablation program. In this case, the control unit may be provided independently of the data processing device and may be connected to the latter by a data link for transmission of the ablation program. The control unit is preferably realized, at least partially, by units of the data processing device which allow control commands to be output to the laser and/or the deflecting device by the ablation program in connection with corresponding circuits of the control unit. Therefore, the laser and/or the deflecting device in the ablation device is preferably connected to the control unit via a corresponding control link. This allows to achieve a particularly simple construction.

The inclination of the surface and the shape of the laser beam profile may be taken into consideration in different ways. In order to enable the use of conventional methods for generating ablation programs and, in particular, methods for generating ablation programs assuming a constant beam profile, i.e. a so-called "top hat" profile, the inclination of the surface and the shape of the beam profile can be effected by way of a pre-compensation of the errors occurring in simple generating methods, by which pre-compensation the desired ablation profile is suitably modified. For this purpose, it is preferred that, in order to consider the inclination of the surface and the shape of the beam profile, the desired ablation profile is used to determine a modified or pre-compensated desired ablation profile as a function of at least the shape of the beam profile and the inclination of the surface at a respective target location on the surface, and the ablation program is generated on the basis of the modified or pre-compensated ideal ablation program. In order to determine the ablation program from the modified or pre-compensated desired ablation profile, simple generating methods can be used which, according to the first aspect of the present invention, are understood to be generating methods which do not simultaneously use the beam profile and the surface inclination to generate the ablation profile. Examples of such simple generating methods are described in DE 19727573 C1 or EP 1060710 A2, the respective contents of which are hereby incorporated into this description by reference.

The desired ablation profile is preferably modified such that ablation according to the ablation program generated on the basis of the modified desired ablation program results at least approximately in the desired ablation profile to be achieved. The errors which occur using a simple generating method in order to generate an ablation program by not considering the beam profile and the inclination of the surface relative to the beam can be compensated for by a corresponding modification of the desired ablation profile, i.e. of the output data for generating the ablation program, so that a simple generating method can still be used as a consequence. In this connection, the type and extent of the pre-compensation or modification may depend on the properties of the simple generating method used or on the model-related assumptions providing the basis of said method. In this way, an enhancement of ablation precision can be achieved while it is possible to resort to simple generating methods.

For this purpose, it is preferred that for at least two surface regions to be ablated one value of a modification function be respectively determined as a function of at least one of the shape of the beam profile and the inclination of the surface in the respective region and that the modified or pre-compensated desired ablation profile be determined using the desired ablation profile and the values of the modification function. The ablation program may thus be generated, in particular, by a simple generating method. The values of the modification function are preferably calculated for each pulse or for each surface location onto which a pulse is to be directed. For each region or for each target location, the values can be calculated anew. However, it is also possible to calculate the values only once and then store them in a table, for example as a function of the inclination, from which table they can then be respectively read out if required.

Preferably, the modification function additionally depends on the intensity, the energy or the fluence of the pulses used for ablation. In particular, the modification function may also depend on a threshold value for the energy or for the effective fluence, said value indicating the energy or effective fluence at which ablation of the material begins to occur.

In particular, the modification function may depend on the dimension-less ratio of the fluence and the threshold fluence value and/or the angle of inclination.

According to another alternative, which also allows the use of simple methods to generate ablation programs, it is envisaged that a preliminary ablation program be determined from the desired ablation profile, that for at least one of the pulses to be emitted a desired value be determined for its energy or fluence depending on the shape of the beam profile, on the inclination of the surface in the region onto which the pulse is to be emitted, and on a prediction of the ablation depth using the preliminary ablation program, and that the generated ablation program comprise the target location of the pulse according to the preliminary ablation program and the determined desired value for the energy or fluence of the pulse. In this case, the pulse energy or fluence near the surface is determined. This means that there is no need to modify the desired ablation profile. Rather, an occurring reduction of the actual ablation depth with respect to an ablation depth assumed for perpendicular impingement of the laser beam on the surface and for a constant beam profile, is accounted for by changing, for example increasing, the energy or fluence of the pulses. Thus, pulses are subsequently emitted onto a predetermined region during ablation with an energy corresponding to the inclination of said region and to the beam profile used. The indication of the pulse energy together with the respective location onto which the pulse is to be directed is then part of the finally generated ablation program used for ablation.

The setting of the energy or fluence of a pulse may be effected in at least three ways which may be applied alternatively or in combination. In a first variant, the laser beam is attenuated in order to set the energy or fluence of a pulse. For this purpose, the control unit is preferably provided to control a modulator which attenuates the laser beam. For this purpose, the first ablation device according to the invention comprises, in addition to the control unit, a modulator which is connected to the control unit and attenuates the laser beam under control of the control unit. Any means allowing to reduce the intensity of the laser beam emitted by the laser may serve as the modulator. For example, Pockel's cells or liquid crystal elements with controllable transmittance can be used. For example, the modulator may have a polarization-dependent effect or a wavelength-dependent effect. The use of modulators allows easy setting of the pulse energy in any type of laser.

In the second variant, the laser used to emit the pulsed laser beam may be controlled so as to set the energy or fluence of a pulse. For this purpose, the control unit, in particular, may be suitably provided to control the laser. In the first ablation device according to the invention, the laser is then preferably controllable by means of the control unit. When excimer lasers are used, the control unit can control, in particular, the high voltage for charging a capacitor or a multiplicity of capacitors in order to store energy for generating a laser pulse. Control of the pulse energy or fluence of the laser has the advantage that less energy is needed.

As a third variant, the beam cross-section of the laser beam on the surface may be changed in order to set the fluence of a pulse. For this purpose, the first ablation device according to the invention may possess a corresponding beam-shaping optical device which is controlled by the control unit.

If maximum precision, i.e. a minimum deviation between the desired ablation profile and the actual ablation profile, is to be achieved during ablation, it is preferred to determine a preliminary ablation program from the desired ablation profile, to predict a predicted ablation profile using the preliminary ablation program as a function of the beam profile shape and the inclination of the surface, and to use the predicted ablation profile to generate the ablation program to be used. The prediction of the ablation profile or of the ablation depth may be effected by a suitable model. This approach allows high precision, because a comparison can be made between the predicted ablation profile and the desired ablation profile.

Particularly when using a modification function or a modified fluence or pulse energy, the modification function or the fluence or pulse energy can be preferably determined for one respective target location each of a pulse and thus for the entire pulse. The modification function is then assumed to be spatially constant for the given pulse, which represents a good approximation if the change in inclination relative to the size of the distance between adjacent points of impingement of laser pulses is small. This is in line, particularly, with the procedure of simple generating methods wherein only single-pulse ablation volumes are considered. This approach has the advantage of being simple. However, it is preferred, particularly with regard to great changes in surface inclination, that the predicted ablation profile be determined at least at two points which are spaced apart by less than the diameter of the laser beam on the surface of the body. In other words, the predicted ablation profile is determined using a spatial resolution that is better than the diameter of the laser beam on the surface of the body. For example, the predicted ablation profile may be used for points of a point grid whose grid spacing is smaller than the diameter of the laser beam. This method variant has the advantage that any change in the inclination of the surface can be taken into consideration.

In the alternative method in which an ablation profile is predicted, a pre-compensated desired ablation profile is preferably determined using the predicted ablation profile and the predetermined desired ablation profile, and the ablation program to be used is generated from the pre-compensated desired ablation profile. This alternative has the advantage that a simple, e.g. known generating method for generating the ablation program to be used can be employed after generating the pre-compensated desired ablation profile. The influences of the beam profile shape and/or of the surface inclination which are not considered by simple generating methods are taken into consideration by the corresponding pre-compensation which depends on the shape of the beam profile and on the inclination of the surface, so that during ablation according to the ablation program to be used, the desired ablation profile is obtained at least approximately.

The described procedure using a predicted ablation profile already allows good pre-compensation. In order to achieve particularly high precision, the ablation program to be used is preferably generated in an iterative manner in that a preliminary ablation program is determined in at least one actual iteration step from a modified desired ablation profile determined in an earlier step, an actual predicted ablation profile is predicted on the basis of the preliminary ablation program as a function of the beam profile shape and of the surface inclination, an actual modified desired ablation profile is determined using the actual predicted ablation profile, and the ablation program to be used is generated as a function of the predetermined desired ablation profile and at least one of the modified desired ablation profiles after the last iteration loop. In this iterative method, a successive improvement of the ablation program and, thus, particularly high precision can be achieved. In the first iteration step, the desired ablation profile can be used instead of a modified desired ablation profile.

When using a pre-compensated or modified desired ablation profile, one value each of a modification function is preferably determined for at least two surface regions to be ablated, as a function of at least the value of the predicted ablation profile and the predetermined desired ablation profile. The pre-compensated ablation profile is then determined using the predetermined desired ablation profile and the values of the modification function. In an iterative approach, the modification function can be determined particularly as a function of the predetermined desired ablation profile and of the modified ablation profiles so that, after the last iteration loop, the pre-compensated desired ablation profile is first determined using the modification function and via the modification function depending on the predetermined desired ablation profile and on the modified desired ablation profiles, and then the ablation program to be used is generated from the pre-compensated desired ablation profile, for example by using a simple generating method. The use of a modification function allows particularly easy consideration of the influences of the beam profile shape and of the surface inclination. In this case, the modification function may be provided analytically and may then explicitly depend, in particular, on the intensity, the energy or the fluence of the pulses to be used for ablation, or it may be given by values at supporting locations of the desired ablation profile or supporting locations for describing the surface, which are numerically determined.

For example, iteration may be aborted after a predetermined number of iteration loops. However, an abortion criterion preferably verified in at least one iteration is whether the predicted ablation profile determined in a previous iteration corresponds to the ablation profile predicted in the current iteration step according to a predetermined criterion, and if it is found to correspond, no further iteration steps are passed through. A criterion to be verified may be, for example, whether the ratio of the predicted ablation profiles for all locations in the region to be ablated in two subsequent iteration loops differs by less than a predetermined limit value of 1. Alternatively, it may be verified, for example, whether the differences between the predicted ablation profiles for all locations in the region to be ablated in two subsequent iteration loops are smaller than another predetermined limit value.

Under certain circumstances, the predicted ablation profile, due to the calculation at discrete locations, for example on a grid, is not smooth, but has peaks which represent artifacts. Therefore, the corresponding predicted ablation profile or a function determined therefrom, in particular the desired ablation profile or the function given by the values of the modification function, is preferably smoothened prior to generating the actual ablation program. For this purpose, use can be made, in particular, of corresponding equalizing methods or low-pass filters.

In order to be able to consider with maximum precision the influence of the beam profile shape and of the surface inclination, e.g. in the form of the modification function or the determination of the predicted ablation profile, a model is preferably used by means of which the profile of the ablation depth can be predicted for a pulse as a function of the shape of the beam profile. In doing so, models may be used which either represent the entire volume ablated by a pulse or even locally represent the ablation depth as a function of at least the fluence at the location with a resolution greater than the beam cross-section. Such models are generally known.

In particular in case the generation of the ablation program using the first method according to the invention requires a relatively great amount of time as compared to the duration of the actual ablation, it is recommended to generate the ablation program prior to beginning the ablation. The ablation program, i.e. the series of target locations onto which the pulses are to be directed, and, where appropriate, the corresponding pulse energies, may then be temporarily stored in order to be successively read out later when effecting the actual ablation.

If a change in fluence or in the energy of the pulses occurs as a function of the surface inclination and of the beam profile shape, it is preferred to determine during ablation the energy or fluence of at least two pulses as a function of the beam profile shape and the surface inclination in the respective region onto which the respective pulse is emitted. In particular, only a preliminary ablation program may be initially present, for example one which has been generated by a simple generating method and which indicates the target locations onto which the pulses are to be directed. For each of the target locations, the pulse energy or fluence can then be suitably determined, and the pulse energy or fluence can be controlled. Thus, the ablation program comprises the target locations of the preliminary ablation program, supplemented by the corresponding settings for the pulse energies or the fluence values. An advantage of this embodiment is that it enables part of the ablation program of use to be generated during ablation, particularly also allowing consideration of changes in the beam profile during ablation.

The beam profile need not necessarily be variable over time. Rather, the shape of the beam profile may be constant for a given ablation device, so that the generating method can always use the same shape of the beam profile which may then be stored, for example, in the generating device. As an alternative, it is possible that the functional shape of the beam profile, for example corresponding to a parametrized Gaussian function, is fixed, in which case, however, a shape-determining parameter, e.g. the half width in case of a Gaussian function, is read in. However, in order to allow for any desired variability of the beam profile shape during ablation or even during subsequent ablations, it is preferred that the data processing device in the generating device according to the invention comprise an interface for input of data characterizing the shape of the beam profile of the laser beam. In this case, too, the interface may comprise a physical and/or a software interface. The beam profile may in turn be described either in the form of values for intensity, energy or fluence as a function of the position in the beam profile, or by indicating values of shape parameters of a function which is parametrized by the shape parameters and which represents the shape of the beam profile. In particular, the interface may be provided for manual input of data and/or for automatic transmission of data via a data link.

In order to facilitate detection of a beam profile, the generating device preferably comprises a device for detecting the shape of the beam profile of the laser beam. This device detects not only the shape of the beam profile, but preferably also enables detection of at least one further beam parameter, e.g. the cross-section of the laser beam. According to this method, it is then preferred that in order to generate the ablation program, the beam profile be measured, preferably automatically, for which purpose the device for detection of the beam profile may be used. The detection or measurement may be effected before generating the ablation program or, if the ablation program is generated fast enough, during generation of the ablation program or during ablation. If a computer program is used to carry out the generating method, said program comprises respective instructions for controlling the device for detection of the beam profile and for reading in suitable data.

For this purpose, the device particularly preferably comprises a spatially resolving detector for laser radiation, which detector is connected to the data processing device, and a beam splitter which is arranged in the beam path of the laser beam and which deflects part of the laser beam onto the detector.

As an alternative, detection methods using a movable slit aperture, pinhole aperture or edge aperture can be used, which is suitably moved in a scanning manner in front of a radiation detector arranged behind it; the beam profile is then determined from the measured values. Such a method is described, for example, in U.S. Pat. No. 6,666,855.

In order to generate the ablation program, it is necessary to know the inclination of the surface in the region to be ablated. If surfaces with a simple geometry are present, manual input of corresponding surface parameters, from which the inclination can be determined in a position-dependent manner, is possible. For example, it is possible to indicate the radius of curvature in case of a spherical geometry as it is present in the cornea, the two main curvatures in case of a torical surface, as well as the coordinates of the central positions (spherical or torus axis, respectively) in case of a lateral offset of the above-mentioned surfaces, the angle and direction of inclination in case of a simple inclined, planar surface, and an aspherity parameter in case of aspherical surfaces, such as surface regions of an ellipsoid.

The corresponding data can be input simply via the corresponding interface. However, in the first generating method according to the invention topographical data of the surface are preferably detected in order to generate the ablation program. The detected surface topography data define the inclination of the surface either directly or allow the inclination to be determined. In principle, the interface for detection of the surface data can be provided for manual input of the data or for reading the data in from a predetermined data carrier or from a corresponding device. However, the data are preferably acquired automatically. This has the advantage that it is then easier to correlate a coordinate system in which the desired ablation profile is given with a coordinate system in which the surface data are defined. For this purpose, the first generating device comprises a device for acquiring topographical data of the surface to be ablated. Said device can be controlled by the data processing device to automatically acquire the data. In particular, the device for acquiring topographical data is suitable to acquire data relating to the inclination of the surface to be ablated. Surface topography data or inclinations can be determined, for example, by Placido ring methods or devices, strip projection methods or devices, or by optical coherence tomographs.

Like the surface topography data, the desired ablation profile may be input manually from a data carrier or via a data link, principally after prior determination. However, it is preferred that, in order to generate the ablation program, data for determining the desired ablation profile be acquired, preferably automatically. For this purpose, the first generating device preferably comprises a device for acquiring data in order to determine the desired ablation profile. Said device is preferably controlled by the data processing device. For example, in case of the correction of defective vision, it is possible to use corresponding diagnostic instruments and methods for determining the eye's refractive power and particularly also aberrometers or wavefront analyzers, e.g. of the Hartmann-Shack type. Calculations can be performed by means of suitable computer program modules either via a separate, suitably programmed computer or preferably by using the data processing device that is present in the device anyway.

In this connection, it may prove advantageous if data are read in which indicate the position of a reference point of a coordinate system for the surface to be ablated and/or of a reference point of a coordinate system for the desired ablation profile. In particular, the relative positions of these reference points with respect to each other or their positions in a common coordinate system can be indicated. As reference points, the corresponding coordinate origins are preferably used. For this purpose, the device preferably comprises an input interface by means of which a reference point of a coordinate system for the surface to be ablated and/or a reference point of a coordinate system for the desired ablation profile can be input. If the shape to be ablated does not have rotation symmetry, data relating to the orientation of the coordinate systems relative to each other may also be additionally read in, where appropriate. The data processing device is preferably provided to transfer the data of the desired ablation profile or of the surface topography or inclination, respectively, to a common coordinate system.

If the data indicating the surface topography or inclination and the data of the desired ablation profile are automatically determined, the method according to the invention may also be used, in particular, in ablation methods in which the surface topography and optical properties are determined and a temporary desired ablation profile is determined and is at least partially ablated during ablation. Such a method is described, for example, in WO 01/12113 A1, the respective contents of which are hereby incorporated in the description by reference.

In addition to the beam profile and the inclination, in particular of biological material like the cornea of the eye, there may also be individual differences in the properties of the corneal material and, as the case may be, changes in the shape of the surface appearing during or after treatment and caused by treatment. Therefore, it is preferred to effect pre-compensation as a function of an ablation property of the material, which property depends on the individual body, and/or as a function of a change in surface and/or material properties to be expected during and/or as a result of ablation. As used herein, a surface property is also understood to be a change in shape. For this purpose, a corresponding correction factor can be used in addition to the inclination-dependent modification function. Thus, effects such as the water content of the material or, particularly in case of a material treatment in a living body, a change in surface shape after ablation by healing effects can thus be advantageously taken into consideration.

In order to be able to effect an even more precise ablation, it is preferred, according to the first generating method in which the material contains water, to pass the laser beam over the surface during the ablation to be carried out, and to generate the ablation program on the basis of the desired ablation profile, additionally considering a water content of the material to be ablated. In this manner, the influence of the water on the ablation behavior can also be taken into consideration.

A computer program containing program code to carry out a generating method of the invention, in particular the first such method, is suitable to generate the ablation program when the program is being executed on a computer.

Moreover, the subject matter of the invention is a computer product comprising program code stored on a computer-readable data carrier in order to carry out a generating method of the invention, in particular the first such method, when the computer program product is being executed on a computer. A data carrier is understood herein to be any data carrier, in particular a magnetic data carrier, such as a diskette or hard disk, for example, a magneto-optical data carrier, an optical data carrier, e.g. a CD, DVD or Blue Ray Disc, or any other non-volatile memory, such as a so-called Flash-ROM, for example.

A computer is understood here to be any data processing device, in particular a data processing device of the first generating device, by which the method can be carried out when the program is being executed thereon. In particular, said device may comprise a digital signal processor and/or a programmable microprocessor by which the method is carried out completely or in part. The processor may be connected to a storage device in which the computer program and/or data for execution of the computer program is/are stored.

As mentioned above, for example when using a laser beam with a beam profile that varies considerably, e.g. a Gaussian beam profile, a rather significant portion of the fluence may be below the threshold for the ablation of material in some regions, e.g. at the borders of the laser spot generated by the laser beam on the surface or of the beam profile, respectively. These pulse components do not lead to ablation, but only result in often undesired heating of the material.

Therefore, the first ablation method of the invention preferably uses a laser beam which has a beam profile, at least near the surface of the body, that is not below a predetermined minimum intensity or fluence over the entire cross-section. The threshold value for the ablation of material from the body to be processed is used at least approximately as the minimum intensity or minimum fluence. The use of a beam profile having a Gaussian shape which is cut off at the edges, being also referred to as a "truncated Gaussian" profile, is particularly preferred, because it is easy to generate. For this purpose, the ablation device preferably comprises a beam-shaping device, by means of which the beam profile of the laser beam can be shaped such that, at least near the surface of the body, the beam profile is not below the predetermined minimum intensity or minimum fluence over its entire cross-section.

A method for ablating material from a surface of a body according to a predetermined desired ablation profile by means of a pulsed laser beam having such a beam profile and being passed over the surface, and an ablation device for ablation of material from a surface of a body, which device comprises a laser emitting a pulsed laser beam, a deflecting device for controlled deflection of the laser beam, and a generating device according to the invention as well as a beam-shaping device by means of which a beam profile of the laser beam emitted by the laser can be shaped such that, at least near the surface of the body, the beam profile is not below the predetermined minimum intensity value over the entire cross-section of said profile, also constitutes an invention per se, independent from the method according to the invention for generating an ablation program and from a corresponding ablation method.

A second aspect of the present invention is based on the second object—which is to be regarded as principally independent from the first object—to provide a method for generating an ablation program for the ablation of water-containing material from a surface of a body according to a predetermined desired ablation profile by emission of pulses of a pulsed laser beam onto the surface, which method minimizes deviations between the desired ablation profile and the actual ablation profile actually achievable by ablation using the ablation program, said deviations being due to properties of the body. A further object on which the second aspect of the invention is based consists in providing means for carrying out said method.

This second object is achieved by a second method for generating an ablation program, namely a method for generating an ablation program for the ablation of water-containing material from a surface of a body according to a predetermined desired ablation profile by emission of pulses of a pulsed laser beam onto the surface, wherein the ablation program is generated on the basis of the desired ablation profile and considerating a water content of the material to be ablated.

In this connection, an ablation program, in particular the ablation program generated by means of the generating method according to the invention and used for ablation, is understood to be—as described above—at least one indication of a series of beam shapes of a pulsed laser beam and/or of target locations or directions by which or onto which or into which the pulses of the laser beam are emitted. In addition, the ablation program can contain or predetermine either one value of the pulse energy or of fluence for the entire sequence or, for each pulse or group of pulses, one value each of the pulse energy or fluence to be used for the pulse or group of pulses. In the second case, the values may depend on the target location. In this case, the ablation profile is understood to be an indication of the ablation depth as a function of the location on the surface or of a direction of the laser beam with respect to the body. Thus, said profile may be a desired, theoretical profile or an actual profile.

The second method for generating an ablation program is based on a predetermined desired ablation profile. The desired ablation profile may be represented in any desired manner. For example, it may be given by points on a predetermined point grid in a reference plane and by indications of the ablation depth which are respectively assigned to said points. However, it is also possible to indicate the desired ablation profile by at least one function parametrized by at least one functional parameter and by a value of the functional parameter, the function and the value of the functional parameter being selected such that the function indicates the ablation depth depending on the functional parameter's value and on the location in the reference plane. In the case of a function-related representation, polynomials, splines, Zernike polynomials or other representations may be used, for example.

The second method is provided for generating an ablation program for the ablation of water-containing material. The water may be contained in the material in any concentration or in any weight or volume percentage, but the material is assumed to be substantially dimensionally stable at least on a time scale of several minutes. The water may be incorporated in a matrix or may be bound, preferably physically, to a further substance of the material. The material may be, in particular, biological tissue. Particularly preferably, the method may be used for ablation of material from the cornea of the human eye. In order to take the water content into consideration, it may be given particularly in the form of corresponding data. The water may, of course, include still further substances, e.g. salts or other dissolved matter.

The invention, i.e. the aspect of the invention given by the second method, is based on the concept, among others, that the ablation depth caused by emission of a laser pulse onto the body and down to which material is ablated by the individual laser pulse depends on the water content in the volume to be ablated. This dependence could be due, for example, to the fact that for ablation the energy of a pulse serves to detach the entire material, including the water contained therein. The water may have a different absorption for the laser radiation and a different evaporation heat than at least one further substance which the material comprises. If the water content changes, the ablation properties may also change due to the modified composition of the material.

Now, when generating the ablation program, the water content is preferably taken into consideration such that the actual ablation profile achieved by an ablation according to the ablation program corresponds as closely as possible to the desired ablation profile. The primary object here is to take the water content into consideration for predetermining the properties and target locations of pulses to be emitted, but not to influence the water content, for example, in the sense of keeping it constant. Thus, it is not attempted to keep the water content of the body, e.g. the cornea, or a liquid film on the body as constant as possible by selection of the ablation conditions, but the ablation program is adapted to the existing or the expected water content of the body.

The consideration of the water content may be effected, in particular, such that the dependence of a pulse's ablating effect on the water content, in particular on a variation of the water content, and optionally also the change in water content by the ablation is detected. Variations in water content may occur particularly in a body spatially as well as during the course of the ablation, i.e. temporally, on the one hand, and as a deviation from a typical, e.g. statistical, mean value between several bodies, on the other hand.

Taking the water content into consideration allows to generate an ablation program which leads to an actual ablation profile during ablation, said profile coming very close or even corresponding to the desired ablation profile even in case of water contents that vary from ablation to ablation or vary in the material. This is very advantageous, in particular, for the ablation of biological tissue.

The ablation program may depend on still further parameters, e.g. beam parameters such as the beam diameter at the surface of the body, the pulse energy or fluence used, the pulse repetition frequency, as well as other material properties of the material to be ablated.

The second generating method according to the invention can be carried out by means of a second generating device according to the invention. Such a device for generating an ablation program for the ablation of water-containing material from a surface of a body according to a predetermined desired ablation profile by emission of pulses of a laser beam onto the surface, wherein the laser beam is passed over the surface, comprises a data processing device which is provided to carry out the second method according to the invention for generating an ablation program.

In particular, the data processing device may comprise a processor for execution of a computer program by means of which the ablation program can be generated according to the generating method of the invention, in particular the second generating method, when the computer program is executed on the computer, as well as a memory in which the program is stored. Moreover, the data processing device may also comprise a physical and/or software interface via which the desired ablation profile or data for calculating it can be read or input into the device. This is of particular advantage if different desired ablation profiles are to be used for different ablations.

A further object of the invention, particularly with regard to the second aspect, is a method for generating control signals to control a laser of a laser ablation device to emit a pulsed laser beam and/or a deflecting device of the laser ablation device so as to deflect the laser beam in order to ablate water-containing material from a surface of a body according to a predetermined desired ablation profile by means of pulses of a pulsed laser beam, wherein an ablation program for the predetermined desired ablation profile is generated by the second generating method according to the invention and control signals are output to the laser and/or the deflecting device in accordance with the ablation program.

Accordingly, a device for generating control signals for a laser and/or a deflecting device of a laser ablation device, in order to ablate water-containing material from a surface of a body according to a predetermined desired ablation profile by means of pulses of a pulsed laser beam, is also an object of the invention, said device comprising a second generating device according to the invention for generating an ablation program on the basis of the predetermined desired ablation profile, and a control unit for emitting control signals according to the generated ablation program to the laser and/or the deflecting device for deflection of the laser beam emitted by the laser.

The control unit, by means of which the control signals are generated and preferably emitted, can be provided independently of the data processing device and can be connected to the latter by a data link for transmission of the ablation program. It is preferably realized, at least in part, by units of the data processing device by means of which control commands can be output to the laser and/or to the deflecting device by the ablation program in combination with suitable circuits of the control unit, which advantageously results in a particularly simple construction. The deflecting device and the laser are controllable as a function of the ablation program generated by the first generating device so that pulses of the pulsed laser beam emitted by the laser are directed onto corresponding target locations on the surface.

The laser ablation device may comprise, in particular, the control signal-generating device, which results in the advantage of a particularly compact design. Therefore, the laser and/or the deflecting device in the laser ablation device is/are preferably connected to the control unit via a corresponding control link.

Ablation according to the above-mentioned "spot scanning" method has the advantage that, in most cases, simply any ablation profile can be ablated. Therefore, the generating method and the generating device preferably serve to generate an ablation program for the ablation of water-containing material from a surface of a body according to a predetermined desired ablation profile, by emitting pulses of a laser beam onto the surface, over which said laser beam is passed. The ablation program then preferably comprises a series of target locations and target directions with which or onto which or in which the pulses of the laser beam are preferably emitted. If pulses are sequentially emitted onto the same target location, the target location has to be specified only once, if the number of pulses to be emitted onto said target location is specified at the same time.

In the following, preferred embodiments and improvements of the invention according to a second aspect will be described, which also represent, in particular, preferred embodiments and improvements of the first aspect of the invention, i.e. of the first generating method, the first generating device, the first ablation method and the first computer program, in which the beam shape and the inclination are taken into consideration.

In principle, it may suffice for the generating method to assume the water content of the material to be constant throughout the entire volume to be ablated. However, it is preferred that, when generating the ablation program, the water content taken into consideration is a function of the location on the surface or in a region to be ablated. This approach has the advantage that, on the one hand, local differences in the water content of the region to be ablated, which is defined by the desired ablation profile, or volume to be ablated and, on the other hand, the differences caused by the ablation, for example between the periphery of the region to be ablated and its center, can be taken into account, which leads to higher precision of the ablation.

The water content can preferably be taken into consideration when generating the ablation program to be used for ablation, by using a model which represents the dependence of the ablation depth which is achieved by at least one pulse emitted onto a target location at the surface, or of the ablation volume which is achieved by the at least one pulse emitted onto a target location at the surface, on the water content of the material to be ablated by the pulse. In particular, the model may be given by a function which depends on a parameter that depends on or represents the water content, said function at least approximately indicating the ablation depth for a pulse of the pulsed laser beam with predetermined pulse properties, e.g. a given pulse energy or fluence. Such models can be obtained by theoretical considerations or from experimental studies of the ablation depth or of the ablation volume in case of ablation by a single pulse, as a function of at least the water content and the subsequent representation of the results by suitable functions. In particular, in a method step or in a computer program by means of which the generating method is carried out, the model may be taken into consideration in such a way that formulae derived from the model are evaluated with parameters of the model during execution of the program.

The model preferably contains as a parameter an ablation rate which depends on the water content. This advantageously allows consideration of the fact that the water content influences the ablation depth.

Typically, not every laser pulse results in ablation. Therefore, the method preferably comprises determining a threshold fluence value for the ablation of material from the surface of the body and determining the threshold value as a function of the water content. This approach has the advantage that an effect of the water contained in the material on the actual occurrence of an ablation can be taken into consideration in a simple and controlled manner.

Indications as to the water content in the material may enter into the method in different ways. In principle, this merely requires the use of corresponding data. Thus, a fixed further model of the water content can be used for a predetermined type of material, for which purpose the data processing device of the generating device may comprise a corresponding program module stored in a memory in the generating device, in which module the further model, including corresponding parameter values, is encoded in a fixed manner. As an alternative, a parameter value may also be permanently stored in a parameter file.

Pulses already emitted onto a region of the body can influence the water content of said region or of adjacent regions. Therefore, the generating method preferably uses a further model indicating, for a predetermined region of the material, the influence that pulses of the pulsed laser beam which have impinged on this region or on adjacent regions have on the water content. The model needs to define the influence only approximately. In particular, the model may indicate the influence in that it depends on the desired ablation depth in said region, which depth is a very good approximation of the number of pulses to be emitted onto said region, where appropriate, in a non-linear manner. A region may be particularly understood to be a column of material which column is substantially orthogonal to the surface and is successively ablated by impinging pulses, with the water content in the remaining part of the column changing due to ablation. This approach has the advantage that a measurement of the water content during ablation is not absolutely necessary. The ablation program considers this effect already when the ablation program is being generated. The model of the ablation depth or of the ablation volume and the further model are preferably selected such that, as the desired ablation depth or the number of pulses to be emitted onto the same region increases, the ablation effect of a pulse increases, i.e. the ablation depth or the ablation volume generated by a pulse increases. This particularly allows to reduce the problems of correcting near-sightedness or far-sightedness by conventional ablation methods, wherein the ablation actually achieved in regions of a small desired ablation depth ends up being too small as compared to the desired ablation depth.

However, if variations in the water content of the otherwise substantially identical material may occur in different bodies and/or if it should be possible to generate ablation programs for ablation of different materials, the generating method preferably acquires data which describe the water content, in particular spatially resolved on the surface or in the region to be ablated, or from which the water content, in particular spatially resolved on the surface or in the region to be ablated, can be determined. The generating device then preferably comprises an interface for acquisition of data which describe the water content of the material or from which the water content can be determined. The data processing device is preferably provided to determine the water content from the data from which the water content of the material can be determined. If the water content is assumed to be constant in the region to be ablated, it may suffice to read in only one corresponding value via the interface. If the water content is taken into consideration in a spatially resolved manner, corresponding data in the form of a field of values indicating the water content may be given for a parameter at predetermined locations of support in the volume to be ablated or on a reference surface intended to describe the volume. As an alternative, it is possible to describe the water content by a parametrized, position-dependent function in providing the parameter values of said function.

The details of the water content may be determined in different ways. Thus, according to one embodiment, the water content is preferably determined by empirical studies of various samples of the material. Particularly in the case of biological material, surveys can be carried out on material or tissue of the same type, but from different individuals of a species, wherein an average water content is determined which then enters into the generation of the ablation program. In this case, it may be assumed, in particular, that the water content is approximately constant over the entire region to be treated. This approach has the advantage that it does not require individual data concerning the respective body to be treated and that it is thus easily and quickly applicable. In particular, corresponding values can be permanently stored in the data processing device, although input via an interface as mentioned above is also possible.

During ablation, the water content of the material may change due to the ablation. Therefore, the generating method preferably uses a model for the water content or the change in the water content of the material as a function of at least the number and/or the position of pulses previously emitted onto the same location and/or adjacent locations in order to take the water content into consideration when generating the ablation program. Thus, the change in water content during the ablation may be advantageously considered without requiring a measurement of the water content during ablation. Values of parameters which may optionally appear in the model can be determined, for example, empirically as above.

In order to obtain high precision of the ablation, i.e. a small deviation between the desired ablation profile and the actual ablation profile achieved by ablation according to the generated ablation program to be used, it is preferred, however, that the generating method determine the water content from data measured at the body. This has the advantage that no assumptions concerning the water content have to be used. The water content need not be explicitly calculated; rather, it may suffice to determine a quantity which unambiguously determines the water content, which quantity is then inserted into a formula in which the dependence on the water content itself is replaced by the dependence on said quantity. The data processing device of the generating device is preferably adapted to determine the water content from the data measured on the body. For this purpose, a computer program running in the data processing device may contain suitable program code. The measurement of the data may be effected prior to generating the ablation program and, in particular, prior to ablation or during generation of the ablation program and formation of the control signals.

In particular, the data may be read in, for example, via a suitable interface as mentioned above, from a data carrier, a user interface, or a measuring device. The data are preferably measured at the body automatically. For this purpose, the generating device may comprise a control interface for a measuring device measuring data at the body, which data indicate the water content or from which the water content can be determined, said control interface allowing the output of control commands to the measuring device for acquiring measured data. This allows the total processing time to be substantially reduced.

As data measured at the body, use is preferably made of data allowing the water content in the material at the surface or in a region to be ablated to be determined in a spatially resolved manner. If the data are measured automatically, said measurement is thus preferably effected in a spatially resolved manner in the material at the surface or in a region to be ablated. In this manner, the water content can be advantageously taken into consideration in a position-dependent manner, which leads to enhanced precision of ablation.

The data may be acquired prior to the actual ablation. However, in a particularly preferred embodiment of the invention, suitable data are also acquired while forming control signals according to a first part of the ablation program or during ablation, thus enabling very precise control of ablation.

The water content can be determined in different ways. In particular, one of the possibilities mentioned below or a combination of these possibilities can be used. According to a first alternative of the generating method, the determination of the water content uses data which indicate the temperature of the surface. For this purpose, the generating device may preferably comprise a device for detecting a temperature of the surface, said device being connected to the data processing device via a data link in order to transmit acquired temperature data to the data processing device, and wherein the data processing device is adapted to determine the water content of the material as a function of the temperature data. This embodiment has the advantage that a temperature measurement can be simply carried out in a spatially resolved, non-contacting manner, too, by using suitable infrared cameras as measuring device, for example.

As a further possibility, in determining the water content data are preferably used which indicate properties of optical radiation emitted by the material in the body's region to be ablated. The corresponding data are preferably acquired automatically. For this purpose, the generating device may comprise a spectrometer, which is preferably connected to the data processing device via a data link, for analysis of radiation emitted by the body's region to be ablated. The data processing device may then be adapted to determine the water content as a function of the data acquired by the spectrometer. For this purpose, a computer program stored in the data processing device may contain program code for determining the water content as a function of the data acquired by the spectrometer. This alternative has the advantage that, on the one hand, a non-contacting acquisition of the data and, on the other hand, precise detection of the water content is possible. Moreover, it is also possible to detect the radiation in a spatially resolved manner, thus enabling a position-dependent determination of the water content. In a laser ablation device comprising a laser, which emits the laser beam, and a generating device, the viewing direction or direction of detection of the spectrometer is preferably inclined with respect to the laser beam at the surface of the body. This enables easy integration of the spectrometer into the laser ablation device.

Particularly preferably the determination of the water content uses data which are obtainable by confocal Raman spectroscopy of optical radiation from the surface. For this purpose, the generating device preferably comprises a device for carrying out confocal Raman spectroscopy, which device is connected to the data processing device via a data link so as to transmit acquired spectroscopic data to the data processing device, which data processing device is preferably adapted to determine the water content of the material as a function of the spectroscopic data. This method allows particularly good specificity of the measurement for water.

As a further possibility, the determination of the water content may use data which indicate the properties of fluorescent radiation emitted by the body's region to be ablated. For this purpose, the generating device may preferably comprise a device for detection of fluorescent radiation, which device is connected to the data processing device via a data link for transmission of detected fluorescent-radiation data, said radiation being emitted by material at the surface of the body upon irradiation of the body's surface to be ablated, and wherein the data processing device is preferably adapted to determine the water content of the material as a function of the fluorescent-radiation data. The fluorescent radiation may be either excited by irradiating the body's region to be examined with a radiation source not used for ablation or, if possible, by irradiation with laser radiation from the laser used for ablation. This alternative is characterized in that the instrumental requirements for carrying out the measurement can be kept relatively low.

A still further possibility consists in that the determination of the water content uses data which indicate the refractive index in the material. The generating device may preferably comprise an optical coherence tomograph for determining the refractive index of the material, said tomograph being connected to the data processing device via a data link in order to transmit measured data. This takes advantage of the fact that the refractive index of the material may depend on the water content. An advantage of this variant may be that the optical coherence tomograph can also be used for measurements of topography at the surface of the body. The coherence tomograph may further be used to determine the thickness of the cornea before and/or during ablation, i.e. to effect a pachymetric measurement. In particular, this allows to prevent the residual thickness of the cornea being below a predetermined minimum value.

The water content may be considered in different ways. Thus, for example, known generating methods may be modified in ways allowing to use models for ablation which take the water content into account. However, this may require a new design of these methods.

Therefore, according to a further possibility, in order to generate the ablation program to be used, it is preferred to generate from the predetermined desired ablation profile an ablation profile which is pre-compensated as a function of the water content in order to take into account the water content and to generate the ablation program from the pre-compensated ablation profile. The desired ablation profile is preferably modified such that the ablation according to the ablation program generated on the basis of the modified desired ablation profile yields the desired ablation profile to be achieved at least approximately. It is possible, in particular, to use a simple generating method in order to generate the ablation program from the modified or pre-compensated desired ablation profile. In connection with the second aspect of the present invention, a simple generating method is understood to be a generating method which does not take the water content of the material into consideration when generating the ablation program. The errors which occur when using a simple generating method in order to generate an ablation program not considering the water content can be compensated for by a corresponding modification of the desired ablation profile, i.e. of the input data for generating the ablation program, such that a simple generating method can be used then. In this connection, the type and extent of the pre-compensation or modification may depend on the properties of the simple generating method used or on the model-related assumptions providing the basis for said method. Thus, said modification alters the desired ablation profile by way of a pre-correction or pre-compensation such that deviations between the desired ablation depth and the actual ablation depth which may result from not considering the water content of the material when generating an ablation program by a simple predetermined generating method, which does not consider the water content, can be pre-compensated for by changing the predetermined desired ablation profile in the opposite direction or magnitude. This embodiment has the advantage that simple generating methods may be employed to generate the ablation program to be used, allowing the use of methods already validated. Examples of such simple generating methods are described in DE 19727573 C1 or EP 1060710 A2, the respective contents of which are hereby incorporated in this description by reference.

For this purpose, a modification function is preferably used in order to determine the pre-compensated ablation profile, said function depending explicitly or implicitly on the water content of the material to be ablated. In particular, for at least two surface regions to be ablated one respective value of a modification function can be determined as a function of at least the water content of the material at the surface in the respective region, and the modified or pre-compensated desired ablation profile can be determined using the desired ablation profile and the values of the modification function. The ablation program may thus be generated, in particular, by a simple generating method. The values of the modification function are preferably calculated for each pulse or for each surface location onto which a pulse is to be directed. For each region or for each target location, the values can be calculated anew. However, it is also possible to calculate the values only once and then store them in a table, for example as a function of the water content or a quantity depending on the latter, from which table they can then be respectively read out if required. This approach allows the pre-compensated desired ablation profile to be determined in a particularly simple manner. In this case, the modification function may depend explicitly on the water content of the material at the target location or implicitly via at least one further parameter of the modification function.

The modification function may be determined or derived particularly using the aforementioned model for the ablation depth achieved by a single pulse as a function of the water content or by the ablation volume achieved by a single pulse as a function of the water content and, where appropriate, the further model for modifying the water content by ablation, and may thus include said model to that extent.

Preferably, the modification function depends on the intensity, the energy or the fluence of the pulses used for ablation. The modification function may also depend on a threshold value for the energy or effective fluence, said value indicating the energy or effective fluence at which an ablation of the material begins to occur and preferably depending on the water content in the material. In particular, the modification function may depend on the dimension-less ratio of the fluence and the threshold fluence value.

During ablation, the water content of the material may change due to the pulses having already impinged on the body. Since it may be required, under certain circumstances, to emit several pulses onto one target location in order to achieve a desired ablation depth, it is preferred according to the generating method that the value of the modification function at a respectively given location depends on a desired ablation depth at said location given by the desired ablation profile. This has the advantage that the dependence on the water content of the material can be easily taken into consideration even for great ablation depths simply before the actual ablation. The modification function may depend on at least one further parameter which itself depends, in particular, on the water content present in the material or on the modification of the water content by the impingement of a pulse.

It may further prove to be favorable to generate a preliminary ablation program from the desired ablation profile and, in order to establish the ablation program to be generated as a function of the water content, at least a fluence value implicitly or explicitly given by the preliminary ablation program, or a pulse energy of a pulse to be emitted onto the target location given by the ablation program, which energy is implicitly or explicitly given by the preliminary ablation program, is modified as a function of the water content at the target location and is assigned to the target location as an indication. The preliminary ablation program may be generated by any generating method; in particular, a simple generating method may be used which generates the preliminary ablation program from the predetermined desired ablation profile without taking the water content of the material into consideration. However, it is also possible to generate a preliminary ablation program, for example by taking the water content into consideration only in an approximate or simplified manner, and to subsequently correct said program by changing the pulse energy or the fluence value, respectively. Therefore, when determining the change in the fluence value or pulse energy, consideration can be given, in particular, to the fact which assumptions or models were used to generate the preliminary ablation program.

The change in the fluence value may be determined or derived, in particular, by using the aforementioned model for the ablation depth achieved by a single pulse as a function of the water content or for the ablation volume achieved by a single pulse as a function of the water content and may contain said model to that extent.

The energy or fluence setting of a pulse may be effected in at least three ways which may be applied alternatively or in combination. In a first variant, the laser beam is attenuated in order to set the energy or fluence of a pulse. For this purpose, a control signal is preferably formed, said signal allowing to control the transmission of a modulator which attenuates a laser beam used for ablation. To this end, the control unit is preferably adapted to form and emit control signals for control, according to a generated ablation program, of a modulator attenuating the laser beam. In addition to the control unit, the laser ablation device preferably comprises a modulator which is connected to the control unit and attenuates the laser beam due to control signals from the control unit. Any means allowing to reduce the intensity of the laser beam emitted by the laser may serve as the modulator. For example, Pockel's cells, glass disks rotatable under the control of a drive unit and comprising radial sectors of different transmittance, or liquid-crystal elements with controllable transmittance can be used. For example, the modulator may have a polarization-dependent effect or a wavelength-dependent effect. The use of modulators allows easy setting of the pulse energy in any type of laser.

In the second variant, the laser used to emit the pulsed laser beam may be controlled so as to set the energy or fluence of a pulse. For this purpose, control signals controlling the laser of the laser ablation device can be formed, by means of which signals the fluence or the pulse energy of pulses emitted by the laser is controlled. The control unit may be accordingly adapted to form and emit control signals to control the laser according to a generated ablation program. The laser in the laser ablation device is then preferably controllable by means of the control unit. When excimer lasers are used, the control unit can control, in particular, the high voltage for charging a capacitor or a multiplicity of capacitors in order to store energy for generating a laser pulse. Controlling the pulse energy or fluence of the laser has the advantage that less energy is needed.

As a third variant, the beam cross-section of the laser beam on the surface may be changed in order to set the fluence of a pulse. For this purpose, control signals controlling a beam-shaping optical device can be formed in the beam path of the laser beam according to a generated ablation program, said optical device serving to set the beam cross-section, and said control signals can be emitted to the beam-shaping optical device. The control unit may be provided accordingly to form and emit control signals for controlling a beam-shaping optical device in the beam path of the laser beam according to a generated ablation program, said optical device serving to set the beam cross-section. For this purpose, a laser ablation device may comprise a corresponding beam-shaping optical device, which is arranged in the beam path of the laser beam and is controlled by the control unit to change the beam cross-section.

An ablation program, in particular an ablation program wherein the fluence or energy of the pulses used is changed, can be generated prior to the actual ablation. However, it is preferred, in the method for generating control signals, that after a first part of the ablation program has been generated and corresponding control signals have been emitted, at least one further part of the ablation program that has to be executed is generated and corresponding control signals are emitted. This makes it advantageously possible to begin ablation already while the program is still being generated so as to shorten the time between providing the desired ablation profile and ending ablation.

Moreover, it enables a particularly preferred embodiment of the method for generating and emitting control signals, in which a preliminary ablation program is generated on the basis of the desired ablation profile and the water content is determined in order to generate the at least one further part of the ablation program for at least one target location on the surface given by the preliminary ablation program, and the preliminary ablation program is changed by generating the ablation program as a function of the determined water content. This has the advantage that a change in water content during ablation, such change being the result of environmental influences or of a previous ablation at the same location or at an adjacent location, for example, can be allowed for during ablation. In particular, the preliminary ablation program may already have been generated taking into consideration, for example, a water content which corresponds to a statistical mean value, wherein individual variations in water content are taken into consideration during ablation. The preliminary ablation program is preferably converted to the ablation program to be executed or to be used, respectively, by changing the fluence or the pulse energy of pulses to be emitted, said change depending at least explicitly or implicitly on the water content.

It is preferred, particularly in the last-mentioned embodiment, to acquire data by measurements on the body during emission of control signals, which data indicate the water content of the material or from which the water content of the material can be determined. For this purpose, the generating device may automatically control the data measurement device via a control interface.

When generating the ablation program, still further influences can be taken into consideration, which are not taken into account, in particular, by known generating methods, such as those described in DE 19727573 C1 or EP 1060710 A2. Thus, it is preferred that the ablation program be generated also as a function of the humidity of the air at the surface and/or the thickness of a liquid film on the surface. This further embodiment has the advantage that it also takes into consideration influences having an indirect influence on the water content in the material. Moreover, the thickness of the liquid film on the surface can influence the ablation efficiency, if the liquid film has to be evaporated first by the pulses prior to ablation of material. Both the humidity and the thickness of the liquid film may be measured preferably during ablation and may be taken into consideration when generating the ablation program. For this purpose, the generating device preferably comprises an interface for input of data that indicate the humidity or the thickness of the liquid film, and particularly preferably comprises a device for measuring the data indicating the humidity or the thickness of the liquid film. This advantageously allows a particularly compact design and automatic measurement.

It is further preferred for the ablation program to be generated also as a function of a shape of a beam profile of the laser beam and/or of an inclination of the surface. The inclination of the surface is preferably given at least approximately with respect to the laser beam. If the laser beam is swiveled around small angles only, e.g. less than 5°, a central or middle position of the laser beam can be selected, for example, as the reference direction relative to which the inclination is determined. This further embodiment is based on the concept, among others, that the energy per area actually effective for ablation, i.e. the actually effective fluence, of a pulse of the pulsed laser beam impinging on the surface of the body depends not only on the surface's inclination relative to the direction of the laser beam on the surface, but also on the beam profile of the laser beam, in particular on the surface of the body. The beam profile is understood to be the course of the intensity or of the area-related energy or fluence of the pulse over the beam cross-section near the surface. The shape of the beam profile does not include any absolute values of intensity or energy or of the fluence relating to a cross-sectional area which is perpendicular to the laser beam, but merely includes the course of these quantities. Therefore, the method is suitable, in particular, for ablation with laser beams having a non-constant beam profile. This variant of the method has the advantage that even very arcuate surfaces can be ablated with high precision by means a laser beam which, in particular, need not have a constant beam profile. The surface data required to generate the ablation program and from which the inclination can be directly determined, allow to directly define the surface inclination as a function of the location, the gradients of the surface's levels above a predetermined reference plane in which the locations are indicated, or even the levels of the surface above the reference plane as a function of the location, particularly allowing to use also the means of representation mentioned with respect to the desired ablation profile. If these data do not explicitly contain the inclination, e.g. given by corresponding angles, this information can be simply determined by gradient formation and/or using trigonometric relationships.

Depending on the application, the desired ablation profile and/or the data relating to the surface inclination can be stored in the data processing device, which is particularly convenient if several identical bodies are to be ablated one after the other. Although the surface data may change with respect to the inclination of the surface, the generating device according to the invention may still comprise an interface for detecting surface data which directly or indirectly represent the inclination of the surface. The interface may be provided in the same manner as the interface for detecting the desired ablation profile. The surface data are preferably acquired automatically for which purpose the data processing device may comprise a corresponding control interface emitting control commands to a device for acquiring surface data.

As the device for acquiring surface data, the generating device may particularly comprise a topographical measurement system detecting the topography of the surface and/or an aberrometer detecting optical properties of the body. This design has the advantage that, because the topographical system is provided in the device, simple and precise detection of the surface topography of the surface to be ablated becomes possible without an additional alignment of the coordinate systems in which the inclinations or the surface topography data and the desired ablation profile as well as, where appropriate, the water content data are defined.

Taking into consideration the inclination of the surface and/or the shape of the beam profile may be achieved, in particular, by determining a pre-compensated desired ablation profile in order to take the shape of the beam profile and/or the inclination of the surface into consideration on the basis of the desired ablation profile using a modification function which depends on the shape of the beam profile and/or the inclination of the surface, and generating the ablation program on the basis of the determined desired ablation profile, which has been pre-compensated with respect to the influences of the beam profile shape and/or the surface inclination. In order to generate the ablation program on the basis of the desired ablation profile which has been pre-compensated with respect to influences of the beam profile shape and/or of the surface inclination, generating methods may be used again which do not take a dependency on the beam profile shape and/or on the surface inclination into account. In this way, a compensation of errors by way of a pre-correction or pre-compensation can be advantageously effected, wherein the desired ablation profile is modified such that errors occurring due to the use of a generating method which does not consider a dependence on the beam profile shape and/or on the surface inclination are suppressed during ablation according to the ablation program at least with good approximation. The modification function preferably contains the influences of both the water content and the surface inclination and the shape of the beam profile. This advantageously allows the generation of the ablation profile to be simplified.

Particularly preferably, the method involves determining for at least two surface regions to be ablated one respective value of the beam- and/or inclination-dependent modification function as a function of at least the beam profile shape and/or the surface inclination in the respective region and determining a value of the water content-dependent modification function, as well as determining the pre-compensated desired ablation profile by the use of the desired ablation profile and of the values of the modification functions, in particular the product of the modification functions. In particular, the uncompensated desired ablation profile for determining the pre-compensated ablation profile can be multiplied, for respectively given target locations, with the product of the modification functions for said locations. Such pre-compensation can be carried out in a particularly easy and fast manner.

A computer program containing program code to carry out the generating method of the invention, in particular the second such method, is suitable to generate the ablation program when the program is being executed on a computer.

Moreover, the invention provides a computer product comprising program code stored on a computer-readable data carrier in order to carry out the generating method of the invention, in particular the second such method, when the computer program product is being executed on a computer. A data carrier is understood herein to be any data carrier, in particular a magnetic data carrier, e.g. a diskette or hard disk, a magneto-optical data carrier, an optical data carrier, such as a CD, DVD or Blue Ray Disc, for example, or any other non-volatile memory, such as a so-called Flash-ROM, for example.

A computer is understood here to be any data processing device, in particular a data processing device of the second generating device, by which the method can be carried out when the program is being executed thereon. In particular, said device may comprise a digital signal processor and/or a programmable microprocessor by which the method is carried out completely or in part. The processor may be connected to a storage device in which the computer program and/or data for execution of the computer program is/are stored.

The concepts according to the second aspect of the invention may be advantageously employed for ablation of a desired ablation profile from biological material, in particular the cornea, for laser surgical treatment of a visual defect in the human eye, e.g. by means of PRK, LASIK or LASEK.

The invention can be embodied comprising one or several of the following features:

Data for determining the desired ablation profile are acquired in order to generate the ablation program.

Data are read in which represent the position of a reference point of a coordinate system for the surface to be ablated and/or of a reference point of a coordinate system for the desired ablation profile.

A laser beam is used which has a beam profile near the surface of the body that does not decrease below a predetermined minimum intensity or minimum fluence over the entire cross-section.

A device for acquisition of data for determining the desired ablation profile is provided.

An input interface is provided by means of which a reference point of a coordinate system for the surface to be ablated and/or a reference point of a coordinate system for the desired ablation profile can be input.

A beam-shaping device is provided, which shapes a beam profile of the laser beam such that, at least near the surface of the body, the beam profile does not decrease below a predetermined minimum intensity or minimum fluence over the entire cross-section.

Data are acquired which indicate the water content or from which the water content can be determined.

On the whole, the invention may advantageously be employed also for ablation of a desired ablation profile from work-pieces, in particular spectacle lenses, contact lenses and lens implants, and preferably for laser surgical treatment of a visual defect in the human eye.

DESCRIPTION OF THE FIGURES

The invention will be explained in more detail below, by way of example and with reference to the drawings, wherein.

DETAILED DESCRIPTION OF THE PREFERRED EMBODIMENTS

Figure 1:
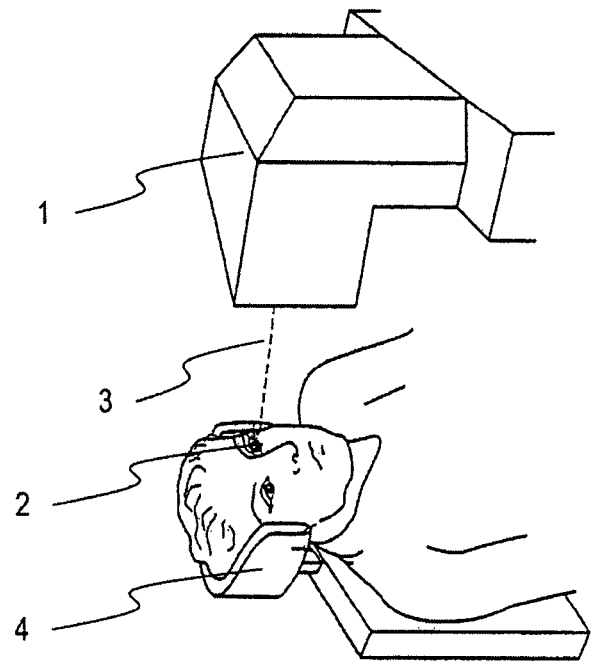
FIG. 1 shows a schematic perspective view of a patient during treatment with a laser surgical instrument comprising an ablation device of a preferred embodiment according to a first aspect of the invention.

FIG. 1 shows a laser surgical instrument 1 for treatment of a patient's eye 2, which instrument serves to carry out a refractive correction of the eye. For this purpose, the instrument 1 emits a pulsed laser beam 3 onto the eye 1 of the patient whose head is fixed by a head support 4 that is securely connected to the instrument 1.

Figure 2:
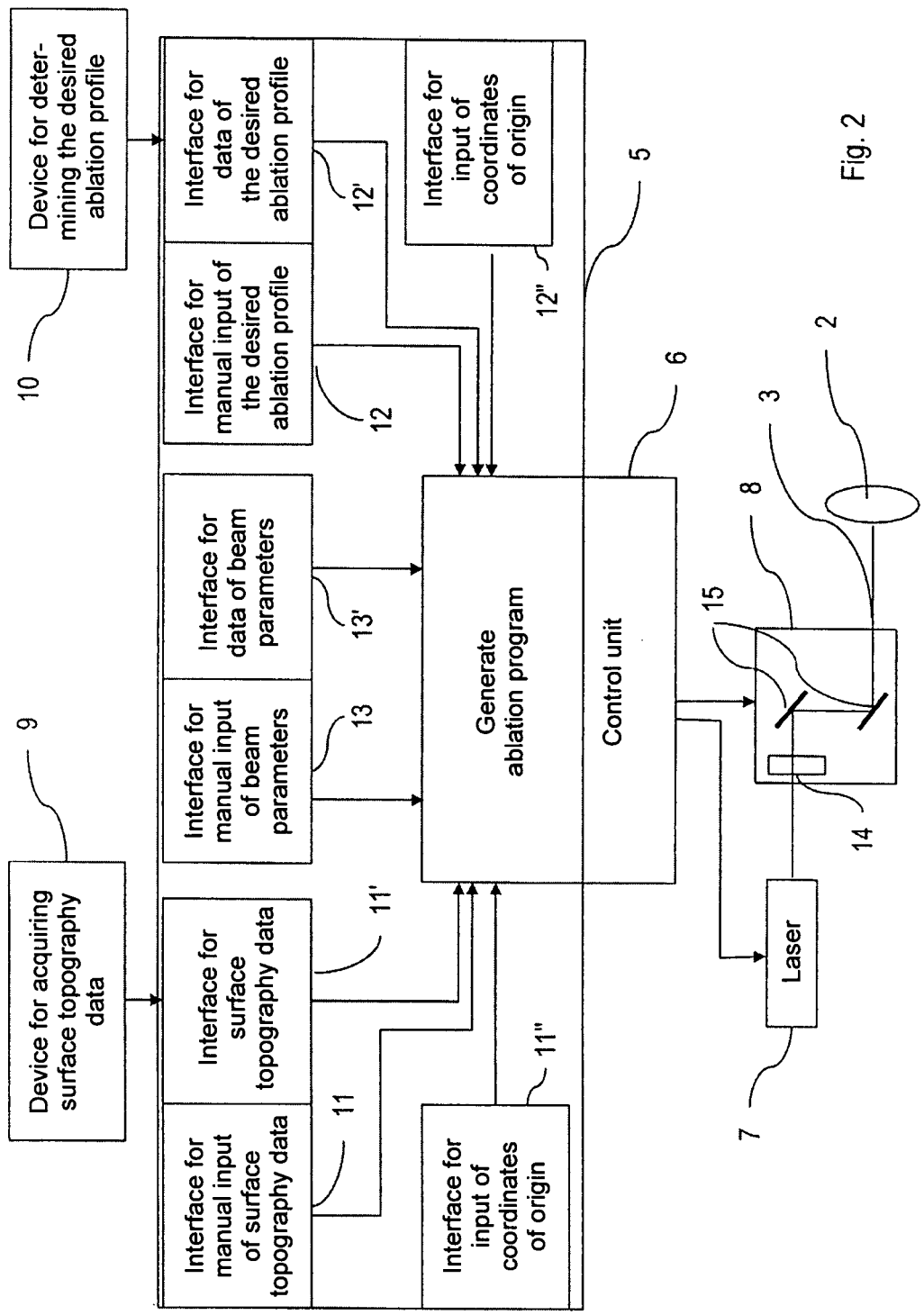
FIG. 2 shows a schematic block diagram of the ablation device of FIG. 1.

FIG. 2 shows more detail of the structure of the instrument which is an ablation device according to the first preferred embodiment of the invention's first aspect. The instrument comprises a data processing device 5 with an integrated control unit 6, a laser 7 controlled by the control unit 6 and a deflecting device 8, which is also controlled by the control unit and by means of which the pulsed laser beam 3 emitted by the laser 7 can be directed and focused on target locations on the cornea of the eye 2 according to a given ablation program.

The instrument further comprises a device 9 for acquiring topographical data of the surface of a region to be treated in the eye 2 and a device 10 for determining a desired ablation profile. Both devices are coupled to the data processing device 5. The data processing device 5, the control unit 6, the device 9 for acquiring the surface topography and the device 10 for determining the desired ablation profile constitute a device for generating an ablation program according to a first preferred embodiment of the invention's first aspect.

The data processing device 5 with integrated control unit 6 serves to generate an ablation program by the use of data representing the surface topography of the region to be treated, data relating to the properties of the laser beam 3 and data relating to the desired ablation profile to be ablated. For this purpose, the data processing device 5 comprises a processor and a memory for storing data, in which, in particular, also a computer program including program code is stored, by means of which the ablation program is generated, when executing the program on the processor, and the actual ablation is effected using the integrated control unit 6. The memory and the processor are partially illustrated in the block diagram by the block "generate ablation program".

To this end, the data processing device 5 possesses interfaces for data input, namely an interface 11 for manual input of the surface topography, an interface 11' reading in surface topography data from the device for acquiring surface topography data, and an input interface 11" for input of coordinates of a reference point of the coordinate system in which the surface topography data are indicated, which coordinates, in the present example, are the coordinates of the coordinate system's origin, an interface 12 for manual input of the desired ablation profile, an interface 12' for reading in data with respect to the desired ablation profile from the device 10 for determining the desired ablation profile, and an interface 12" for input of the coordinates of a reference point of the coordinate system in which the desired ablation profile is given, which coordinates, in the present example, are those of the coordinate system's origin. Moreover, an interface 13 for manual input of beam parameters and an interface 13' for reading in data relating to the beam parameter of the laser beam 3 from a data source are provided. At least one of the beam parameters can serve to describe the shape of the beam profile.

The interfaces for manual input and in particular also the interfaces for input of the coordinates of reference points may be one single interface in physical terms, said interface having connected to it, in a manner not shown in the Figures, a keyboard and a screen on which an input prompt can be displayed when corresponding data are to be read in. The interfaces further comprise corresponding modules of the computer program for reading in data from the keyboard.

The other interfaces 11', 12' and 13' are conventional interfaces for data flows which, in addition to corresponding electronic modules, also comprise software modules.

The control unit 6 is integrated into the data processing device 5 and further comprises interfaces, not shown in the Figures, for control of the laser 7 and of the deflecting device 8. Such control units are known, in principle, and therefore need not be explained in more detail.

The laser 7 is connected to the control unit 6 and emits a pulsed laser beam with predetermined pulse energies as a function of the ablation program. For example, an excimer laser having a wavelength in the wavelength range of 193 nm can be used. The laser beam 3 emitted by the laser 7 has a beam profile which is shown in broken lines in FIG. 12 and has a Gaussian shape.

The deflecting device 8 is also connected to the control unit 6 via a data link and, in accordance with control signals from the control unit 6, directs the pulsed laser beam 3 emitted by the laser 7 onto predetermined target locations on the surface of the eye 2 according to the ablation program to be executed. For this purpose, the deflecting device 8 comprises a focusing device 14 for focusing the laser beam along its direction of propagation and for deflection transverse to the laser beam via two mirrors 15, which are rotatable or tiltable about two mutually orthogonal axes and are arranged in the beam path following the focusing device 14.

Both the laser 7 and the deflecting device 8 may be conventional, known devices of a laser surgical instrument.

Figure 3:
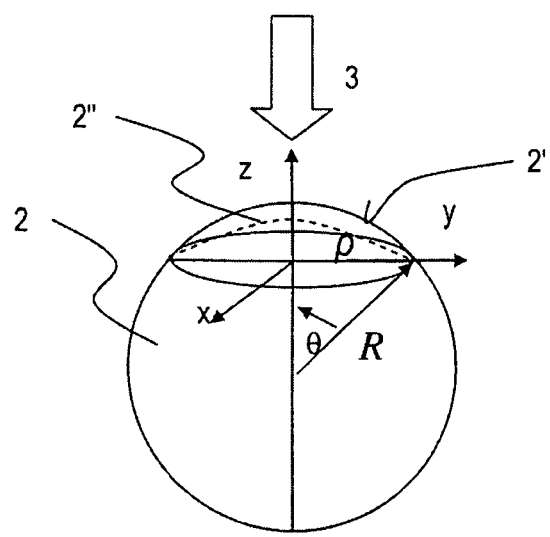
FIG. 3 shows a schematic representation of a spherical body to be processed.

The surface topography is represented using two mutually parallel Cartesian coordinate systems whose x-y planes coincide. If possible, the z axis is aligned parallel to the optical axis of the eye with good approximation. This is shown in FIG. 3 for a spherical body or a sphere with a surface 2' as a simplified model of the eye 2, in which, for the sake of clarity, the z axis representing the desired ablation profile is not shown. The z axes are defined during alignment of the eye 2 relative to the instrument 1.

In the example, the device 9 for acquiring surface topography data comprises an optical coherence tomograph which is arranged in the instrument 1 so as to allow acquisition of the surface topography of the eye 2 in the region to be treated. The optical coherence tomograph acquires surface topography data in the form of heights in the direction of z at grid points in the x-y plane, which is fixed with respect to the instrument 1 and approximately orthogonal to the laser beam 3. The data are read into the data processing device 5 via the interface 11'.

In the present example, the device 10 for determining the desired ablation profile comprises a wavefront analyzer of the Hartmann-Shack type as well as, where appropriate, devices for determining the refractive power of the eye 2, by which analyzer or devices, respectively, a desired ablation profile $D_{Soll}$ for the region to be treated in the eye 2 can be determined according to known methods. In doing so, the desired ablation profile is determined such that correction of imaging errors in the eye 2 can be achieved as far as possible by the ablation to be carried out. An example of the desired ablation profile is evident from FIG. 3. It is given by the distances, in the direction of z, between the initial surface, the calotte 2', and a desired surface 2" indicated by a broken line, as a function of the location in the x-y plane.

In order to determine the desired ablation profile, the device 10 may comprise a suitable processor which evaluates data relating to the refractive power of the eye 2 and the wavefront data in order to determine the desired ablation profile again, in the present example, in the form of the desired ablation depths for points of a point grid in the x-y plane of the corresponding coordinate system which coincides with the x-y plane of the coordinate system for indicating the ablation profile. As far as the coordinate origins are not identical, the position of one of the reference points or coordinate origins in the respective other coordinate system can be given so that the data can be transformed by simple shifting into an identical coordinate system during a later process stage. This may turn out to be favorable if the center of the desired ablation profile, i.e. a point relative to which the desired ablation profile is approximately symmetrical, deviates from the center of the surface of the eye 2, i.e. from a point relative to which the surface of the eye is approximately symmetrical. Such a method for generating a desired ablation profile is described, for example, in WO 01/08075 A1, the respective contents of which are hereby incorporated in the description by reference.

The method for generating an ablation program according to the first exemplary embodiment is based on the following considerations.

In order to ablate the desired ablation profile $D_{Soll}$ from the eye 2, laser pulses having a predetermined pulse energy are emitted onto predetermined target locations according to a generated ablation program, each of said laser pulses individually leading to a removal of material. The depth of removal can be described by various models. In the present example, the so-called "blow-off" model is used, as described, for example, in "Refraktive Chirurgie der Hornhaut", Theo Seiler (Ed.), 1st edition, ENKE Georg Thieme Verlag, Stuttgart/N.Y., 2000 (ISBN 3-13-118071-4), Chapter 6.1, p. 150, or in R. Srinivasan: "Ablation of Polymers and Biological Tissue by Ultraviolet Lasers", Science vol. 234, p. 559-565, 31 Oct. 1986. Following this, material is removed to a depth $D_{1st}$ at a location having the coordinates (x, y), by laser radiation impinging at this location and having an effective fluence F(x, y), i.e. energy per surface area, according to the following formula:

$$D_{1st}(x, y) = \begin{cases} \mu \cdot \ln \frac{F(x, y)}{F_{thr}}, & \text{if } F(x, y) > F_{thr} \\ 0, & \text{otherwise.} \end{cases}$$

In this formula, $\mu$ designates a material-dependent ablation coefficient and $F_{thr}$ relates to a likewise material-dependent ablation threshold fluence value, below which value laser radiation no longer results in material removal from the eye 2.

In the simple generating method for an ablation program used below, it is assumed that the desired ablation profile can be split into single-pulse ablation volumes which each form upon impingement of one pulse. In this case, generating the ablation program includes determining the target locations (x, y) onto which the pulses of a predetermined pulse energy have to be directed.

In generating an ablation program, it is assumed that a laser pulse removes a single-pulse ablation volume or spot ablation volume $V_{pulse}$ which is obtained as an integral of the ablation depth $D_{1st}$ over the entire pulse area:

$$V_{pulse} = \iint_{Spot} D_{1st}(x, y) dx dy = \mu \iint_{Spot} \ln \frac{F(x, y)}{F_{thr}} dx dy.$$

The integral extends over the area designated as "Spot", in which $D_{1st} > 0$ holds.

Whereas conventional methods assume the effective fluence F(x, y) to be constant over the area of the pulse or of the spot, respectively, the invention takes two influences into consideration at the same time. On the one hand, it is considered that the inclination of the surface to be processed reduces the effective fluence according to said inclination relative to the fluence of the laser beam 3. If the surface to be processed is described by a height function f(x, y), which indicates the level of the surface above the x-y plane, the angle of inclination θ of the surface can be determined relative to the z axis and, thus, in approximation to the laser beam 3 incident on the surface 2', according to the formula θ(x,y)=arctan(|grad f(x,y)|)

Thus, the fluence F(x, y) effective during ablation on the surface is obtained as F(x,y)=$F_P$(x,y)·cos θ(x,y), wherein $F_P$(x,y) designates the fluence for vertical incidence of the laser beam 3 on the surface, i.e. at an angle θ=0. Therefore, $F_P$ corresponds to the fluence or the beam profile of the laser beam 3.

The second effect taken into consideration is that the effective fluence varies in accordance with the intensity or energy profile of the pulses in a plane orthogonal to the direction of the laser beam 3 and that it may thereby, in particular, also be below the threshold value $F_{thr}$.

Thus, the actual single-pulse ablation volume results from the following formula:

$$V_{pulse} = \iint_{Spot} D_{1st}(x, y) dx dy$$

$$= \mu \iint_{Spot} \ln \frac{F(x, y)}{F_{thr}} dx dy$$

$$= \iint_{Spot} \ln \frac{F_P(x, y)\cos\theta(x, y)}{F_{thr}} dx dy.$$

Therefore, the single-pulse ablation volume non-linearly depends on the angle of inclination of the surface and on the fluence profile $F_P$(x,y).

In the case of known single-pulse ablation volumes, an ablation program can be generated by known simple generating methods, as described, for example, in DE 19727573 C1 or EP 1060710 A2, according to which ablation program the mean ablation depth $D_M$ results, in a uniformly or slowly varying manner, for a distance a of laser beam pulses directed onto the surface according to:

$$D_M = c \frac{V_{pulse}}{a^2}$$

In this case, c is a proportionality factor resulting from the pattern of the points of incidence of the laser beam's pulses. For example, an approximately square pattern yields c=1, whereas an approximately hexagonal pattern yields c=2/√3.

In the following, it will be assumed that the ablation profile slowly changes spatially with respect to the length of the distance a, or that the inclination slowly changes with respect to the diameter of the laser beam 3 on the surface. In order to describe the spatial dependence of these spatially slowly varying parameters, coordinates u and v will be used in the following, which are given in a u-v coordinate system that coincides with the x-y coordinate system. Thus, the single-pulse ablation volume and, likewise, the mean depth $D_M$ resulting from the pulses placed next to each other are to be understood as a function of u and v.

This allows to calculate a modification function K, which depends on u and v and results as $$K(u, v) = \frac{V_{pulse,1st}(u, v)\cos\theta(u, v)}{V_{pulse,E}(u, v)},$$

wherein the index "E" designates quantities which are determined when using a simple generating method, i.e. one that does not take the inclination and the shape of the beam profile into consideration. The factor cos(θ(u, v)) results from the fact that the distance a in the x-y plane increases by 1/cos(θ(u,v)) in one direction due to the inclination of the surface. $V_{pulse,1st}$(U, v) itself may depend on cos(θ(u, v)). K depends on the shape of the beam profile via $V_{pulse,1st}$.

If an ablation program were determined by any of the aforementioned simple generating methods on the basis of the desired ablation profile $D_{Soll}$, this would yield an actual ablation profile reduced with respect to the desired ablation profile according to the modification function K:

$$D_{1st}(u,v) = K(u,v) \cdot D_{Soll}.$$

Therefore, in order to compensate this error in advance, the desired ablation profile $D_{Soll}$ that is to be ablated is divided by the modification function K, thus yielding a modified and pre-compensated desired ablation profile $D_{Mod}$:

$$D_{Mod}(u,v) = \frac{D_{Soll}(u,v)}{K(u,v)}.$$

Using the simple generating method, this leads to an ablation program which, when being executed, yields the desired ablation profile $D_{Soll}$. If the pre-compensated or modified desired ablation profile is used to determine an ablation program by the conventional simple generating methods, the desired ablation profile is obtained with very good approximation during ablation even in the case of surfaces inclined with respect to the laser beam and a non-constant beam profile.

In order to determine the locations onto which the laser pulses are to be emitted, various known methods can be used, e.g. the methods described in DE 19727573 C1 and EP 1060710 A2. In DE 19727573 C1, ablation is effected in layers, i.e. locations of impingement are determined in a layer-wise fashion for pulses, with the desired profile then resulting from superposition of these layers. According to the method in EP 1060710 A2, the spot distance is varied in a quasi-continuous manner in order to achieve the desired ablation depth.

The calculation of the modification function is explained using as an example the ablation of a spherical surface by a laser beam having a Gauss-shaped beam profile (cf. FIG. 3).

The beam profile or fluence is described by the formula $$F_P(r) = F_0 e^{-\frac{r^2}{w^2}},$$

wherein $F_0$ is the peak fluence value, r is the radial distance from the center of the beam profile, and w is the distance after the profile has dropped to 1/e relative to the value at the center.

For the actual ablation profile of a laser pulse impinging orthogonally on a planar surface, this yields:

$$D_{1st}(r) = \mu \ln \frac{F_0}{F_{thr}} - \mu \frac{r^2}{w^2},$$

so that the single-pulse ablation volume for this pulse is calculated as $$V_{pulse,E} = \frac{\pi}{2} \mu w^2 \left[ \ln \frac{F_0}{F_{thr}} \right]^2.$$

As the mean depth of the desired profile for a square pattern of the points of impingement of the pulses, or spot pattern, having an edge length a, a mean depth of ablation according to $$D_E(r) = \frac{V_{s,E}}{a^2} = \frac{\pi}{2} \mu \frac{w^2}{a^2} \left[ \ln \frac{F_0}{F_{thr}} \right]^2$$

can be expected. If $D_E$ were assumed to be equal to $D_{Soll}$, a could be determined as a function of the location. However, the spherical surface is actually inclined, except at the center, with respect to the laser beam 3 that is assumed to impinge parallel to the z-axis with sufficiently good approximation. As is evident from FIG. 3, the angle of inclination can be calculated in the following manner as a function of the distance ρ of a location on the surface of the eye 2:

$$\theta(\rho) = \arcsin\left(\frac{-\rho}{R}\right) = \arctan\left(\frac{-\rho}{\sqrt{R^2 - \rho^2}}\right).$$

The inclination of the surface at the location ρ then has the effect that both the spot distance in the direction of inclination and the spot width w in the direction of inclination are increased by the factor $1/\cos(\theta(\rho))$. Therefore, the ratio w/a in the equation for D does not change with the inclination. However, the fluence does change in this equation. Therefore, the following result is obtained for the depth profile to be expected on the spherical surface:

$$D_{1st}(\rho) = \frac{V_{pulse,1st}(\rho)\cos\theta(\rho)}{a^2} = \frac{\pi}{2} \mu \frac{w^2}{a^2} \left[ \ln \frac{F_0 \cdot \cos\theta(\rho)}{F_{thr}} \right]^2$$

The modification function $K(\rho)$ is then calculated as $$K(\rho) = \frac{V_{pulse,1st}(\rho)\cos\theta(\rho)}{V_{pulse,E}} = \left( 1 + \frac{\ln\cos\theta(\rho)}{\ln \frac{F_0}{F_{thr}}} \right)^2$$

This result may be systematically obtained also by assuming $\cos(\theta)$ to be constant over the spot area in the formula for the single-pulse ablation volume.

Figure 4:
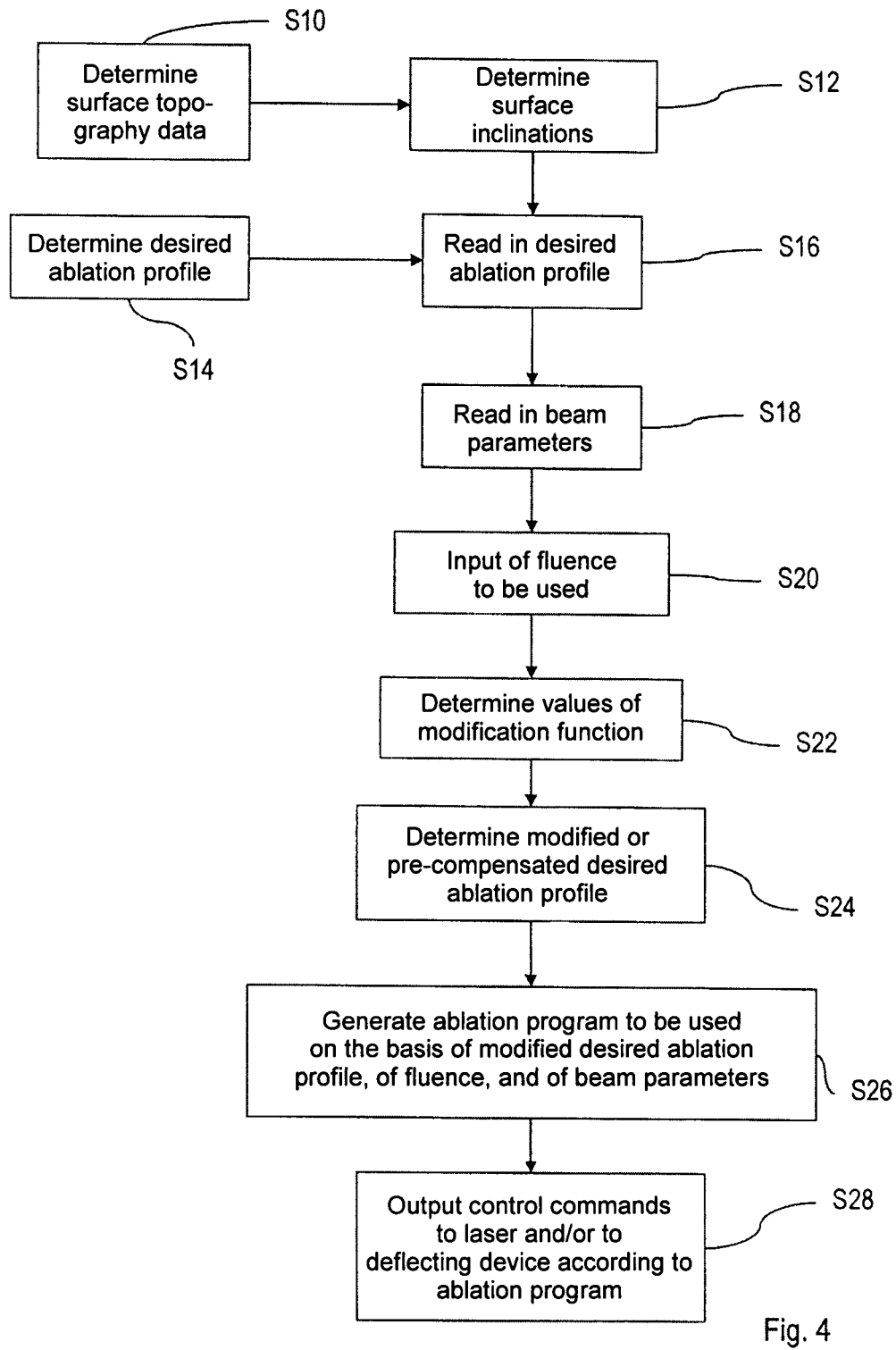
FIG. 4 shows a flow scheme of a method for generating an ablation program for the instrument of FIG. 2 according to a first preferred embodiment of the first aspect of the invention.

The method steps schematically shown in the flow scheme of FIG. 4 are used to determine the ablation program.

At first, the surface topography of the region to be treated is determined in step S10 by the device 9 for acquiring the surface topography data. For example, the corresponding data may comprise heights of the surface with respect to the x-y plane, said heights being detected above a grid of points in the x-y plane.

In step S12, these data are then read into the data processing device 5 via the interface 11' for the surface topography data. Surface inclinations are then determined from the height data by numerical determinations of gradients, as well as determining the above-indicated formula for the angle of inclination. The corresponding data are then stored in the memory of the data processing device 5.

In the example, the desired ablation profile $D_{Soll}$ is determined in step S14, after steps S10 and S12, using the device 10 for determining the desired ablation profile. In other exemplary embodiments, this can also be effected prior to said steps. For this purpose, imaging errors are determined from wavefront data. Known methods are used to calculate at which locations of the eye's surface material is to be ablated to what depth. In the present example, the desired ablation profile $D_{Soll}$ is given by specifying the desired ablation depth as a function of the location on a grid in the x-y plane.

In step S16, these data are then read via the interface 12' into the data processing device 5 and stored there in its memory.

In step S18, beam parameters of the laser beam 3 to be used are then read in via the interface 13. For this purpose, only the diameter or the half-width of a Gaussian beam profile of the laser beam is input in this exemplary embodiment. The Gaussian shape of the laser beam 3 is assumed as fixed and is taken into consideration in the form of corresponding formulae in the program being executed on the processor of the data processing device 5.

In step S20 the pulse energy to be used per surface area or the fluence to be used is then input and stored. More precisely, the peak value $F_0$ of the fluence for the Gaussian profile is input.

In step S22 values of the modification function K are then determined for the entire desired ablation profile, optionally determining, by interpolation, values of the angle of inclination on the grid used to specify the desired ablation profile. The above-specified formula for the function K is used for this purpose. The corresponding values are then stored again.

Following this, step S24 determines a modified or pre-compensated desired ablation profile $D_{Mod}$ by dividing the desired ablation depths, which are given for the respective grid points due to the desired ablation profile read in, by the value of the modification function K determined for each respective grid point. The modified desired ablation profile is then stored.

In the next step S26, an ablation program is generated on the basis of the modified desired ablation profile $D_{Mod}$, the fluence read in, and the beam parameter, for which purpose a method is used that does not simultaneously take the surface inclination and the shape of the beam profile into consideration. For example, the method described in DE 19727573 C1 can be used. The ablation program thus generated comprises a sequence of target locations in the x-y plane, i.e. corresponding coordinates onto which the laser pulses have to be directed with the pulse energy determined by the fluence read in, in order to achieve the desired ablation profile to be achieved. The ablation program is stored in the data processing device 5. This step completes the actual generation of the ablation program.

In the next step S28, control commands are output to the laser 7 and to the deflecting device 8 by the data processing device 5 using the integrated control unit 6 so as to remove material from the eye 2 according to the generated ablation program.

The ablation method is suitable for both photo-refractive keratectomy and LASIK. Since these methods involve the removal of material in different layers of the eye, the use of different desired ablation profiles may be accordingly required in some cases.

According to a further variant of the method just described, the required memory space can be reduced by combining steps S22 and S24 and by calculating the modification function for each point of support of the desired ablation profile without being stored after the corresponding modified desired ablation profile value has been determined.

Figure 5:
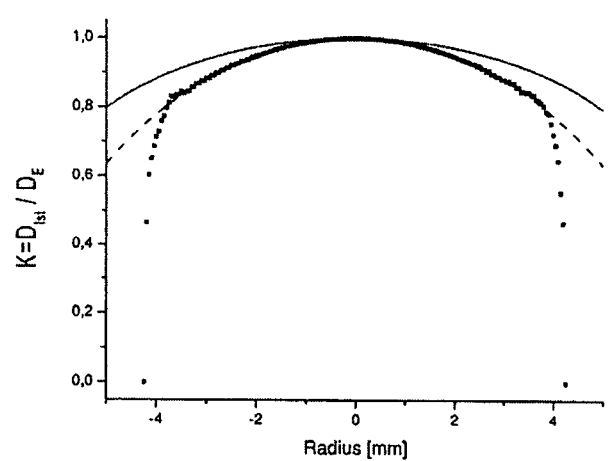
FIG. 5 shows a representation of a modification function depending on the location in the rotation-symmetrical beam profile of a laser beam for three different generating methods.

FIG. 5 shows the modification factor as a function of the radius ρ with reference to a convex-spherical ablation profile on a circular region having a diameter of 8 mm, said region having been formed by ablation on a surface with a radius of curvature of 7.86 mm. The solid line shows a correction factor which is obtained by the method disclosed in WO 01/85075 A1, i.e. particularly without taking the shape of the beam profile into consideration. The broken line represents the result achieved by the method just described. It is easy to see that as the radial distance from the center of the calotte increases and, thus, as the inclination increases, the corrections by the present methods gain importance and differ considerably from those of the prior art.

Figure 6:
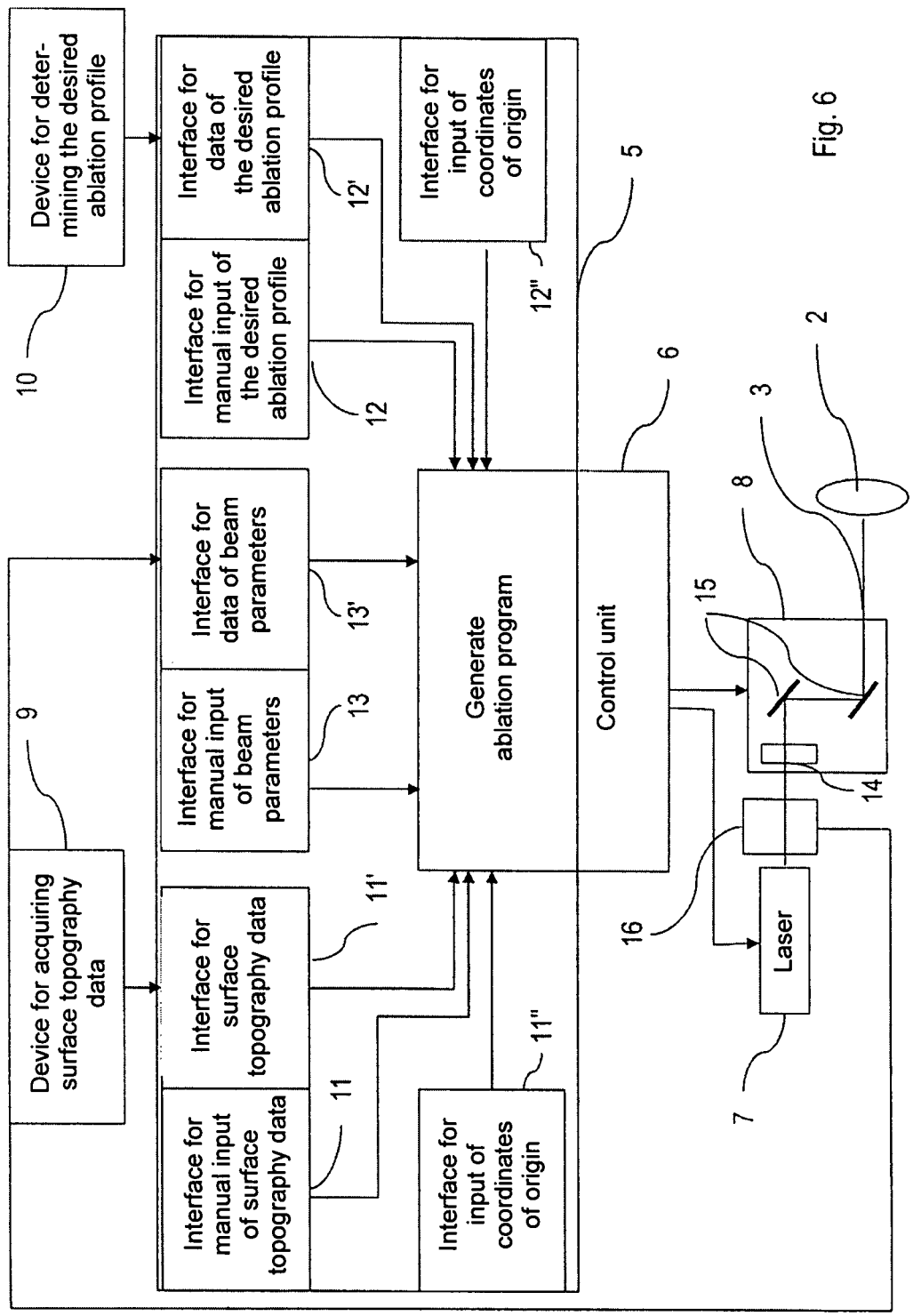
FIG. 6 shows a block diagram of an ablation device according to a second preferred embodiment of the first aspect of the invention for a laser surgical instrument.

FIG. 6 shows an instrument according to a further preferred embodiment of the first aspect of the invention, which instrument differs from that of the first exemplary embodiment in that a device 16 for determining the beam profile of the laser beam 3 is arranged in the beam path of the laser beam 3 between the laser 7 and the deflecting device 8 here, by means of which device 16 the beam profile of the laser beam 3 can be determined and supplied to the data processing device 5 through a suitable data link via the interface 13' for the beam parameters, the data processing device 5 being programmed to execute the variant of the generating method described below.

Figure 7:
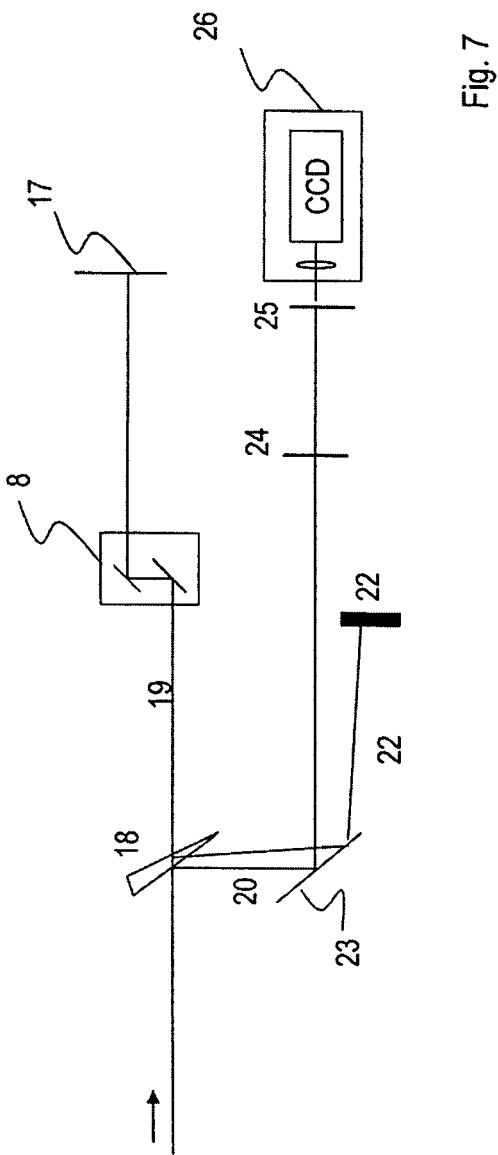
FIG. 7 shows a schematic representation of a device for detecting a shape of a beam profile of a laser beam emitted by the laser of the ablation device of FIG. 6.

The device 16 for determining the beam profile is represented in more detail in FIG. 7. Before reaching the work plane 17, i.e. the plane in which ablation takes place, the laser beam 3 is split into a processing beam 19 and a measurement beam 20 with the help of a beam splitter 18 in the form of a wedge plate. By reflection at its second surface, the wedge plate 18 generates a further beam 21, which is absorbed by a stop 22.

The measurement beam 20 is deflected by a mirror 23, impinges on an optional attenuator 24 and is then incident on a ground glass screen or, when UV light is used, a fluorescent screen 25. The mirror 23 and the frosted glass screen 25 are arranged such that the measurement beam 20 travels approximately the same path length as the processing beam 19 on its way from the beam splitter 18 to the work plane 17.

Using a video camera 26 as space-resolving detector, e.g. a CCD camera, the image of the scattered light from the ground glass screen or of the fluorescent light is recorded in a space-resolved manner and is evaluated electronically. The video camera 26 is selected such that its recording rate is greater than the repetition rate used for the laser, thus allowing the beam profile to be measured even during the ablation operation. In the case of slow changes of the beam profile, a slow analysis of the beam profile may also be effected prior to performing the ablation operation.

A corresponding method for generating an ablation program differs from the corresponding method of the first exemplary embodiment in that step S18 does not involve reading in the width of the Gaussian beam but the beam profile determined by the device 16.

Moreover, step S22 involves determining the values of the modification function by numeric integration according to the following formula $$K(u, v) = \frac{V_{pulse,Ist}(u, v)\cos\theta(u, v)}{V_{pulse,E}(u, v)}$$
$$= \frac{\int_{Spot} r\ln\frac{F_P(r)\cos\theta(u, v)}{F_{thr}}dr}{\int_{Spot} r\ln\frac{F_0}{F_{thr}}dr}\cos\theta(u, v),$$

wherein the beam profile is assumed to have rotation symmetry and r designates the radius transverse to the propagation direction of the laser beam.

Figure 8:
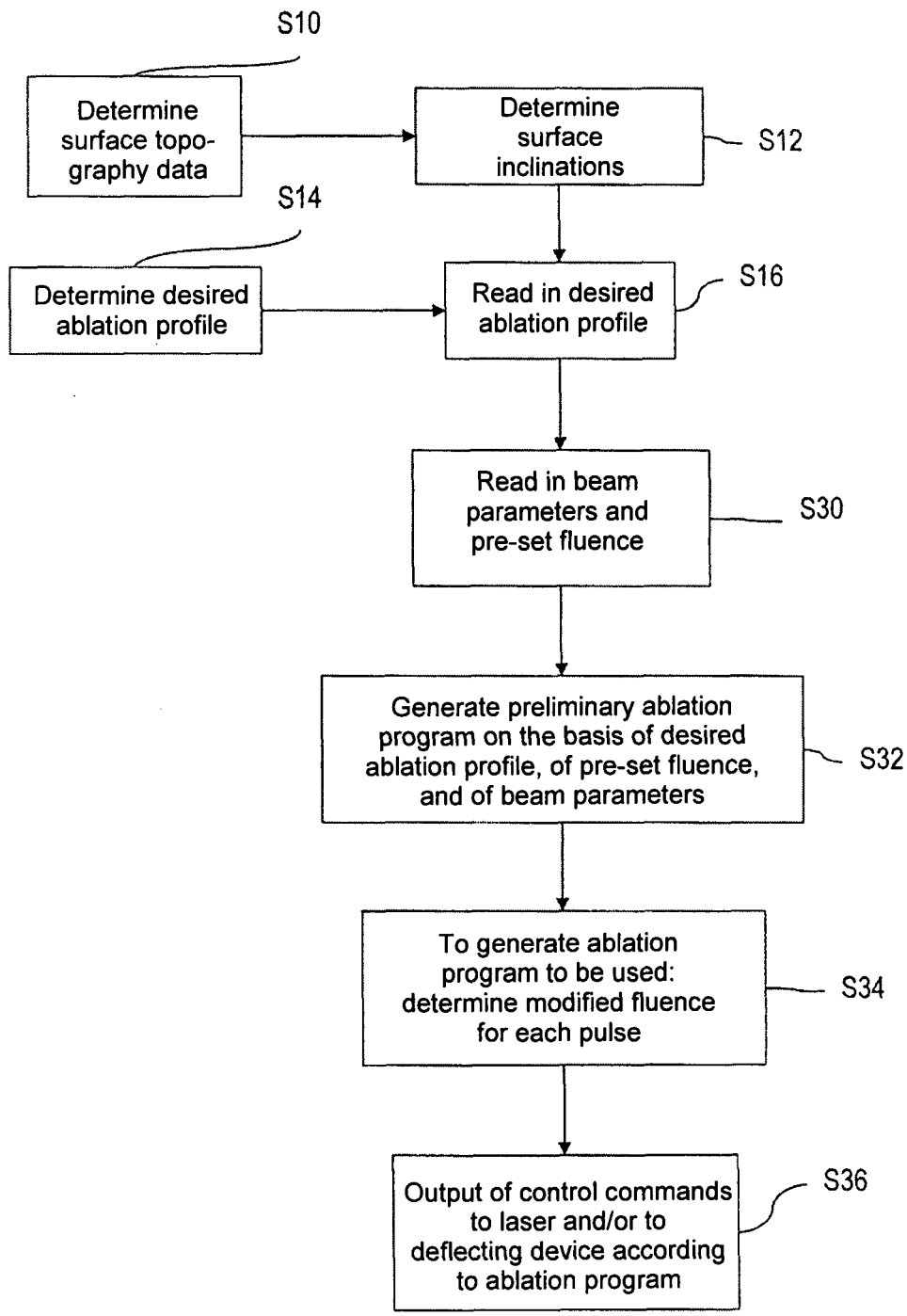
FIG. 8 shows a flow scheme of a method for generating an ablation program according to a third preferred embodiment of the first aspect of the invention.

A third exemplary embodiment of a method for generating an ablation program is illustrated in FIG. 8. A corresponding instrument differs from the instrument of the first exemplary embodiment by programming the data processing device 5 such that it can carry out the ablation method described below.

The ablation method which encompasses the method for generating an ablation program comprises several steps which correspond to those of the method described in FIG. 4. Therefore, these will be referred to below by the same reference numerals and will not be described in detail again.

Thus, data relating to the surface inclination are determined and stored in steps S10 and S12, and data relating to the desired ablation profile are determined and stored in steps S14 and S16.

In step S30, which follows then, the width of a given Gaussian beam profile and a pre-set initial fluence value, i.e. a pre-set initial peak value, are read in.

In step S32, which follows, a preliminary ablation program is then generated on the basis of the input desired ablation profile, the pre-set fluence read in, and the beam parameters, wherein the simple generating method used for this purpose does not take the shape of the beam profile into consideration simultaneously with the inclination. In particular, the above-mentioned method of DE 197 27 573 C1 can be used. The preliminary ablation program which in turn comprises a series of coordinates for locations on the surface of the eye 2, onto which the pulses are to be directed, is then stored.

Next, in order to generate the ablation program to be finally used, fluence values or pulse energies which are modified with respect to the pre-set fluence peak value are determined for each pulse in step S34. If the simplified method used to generate the preliminary ablation program is based on a single-pulse ablation volume $V_{S,E}$, the following relationship between the actual single-pulse ablation volume $V_{S,1st}$ for one pulse and the single-pulse ablation volume $V_{S,E}$ used to generate the preliminary ablation program results as already described above:

$$K(u,v) = \frac{V_{pulse,1st}(u,v)\cos(\theta(u,v))}{V_{pulse,E}(u,v)},$$

wherein $V_{pulse,1st}$ and $V_{pulse,E}$ are functions of the dimensionless ratio $F_0/F_{THR}$. In addition, $V_{pulse,1st}$ also depends directly on the inclination or the angle $\theta$ at the corresponding location.

The inclination is known for each pulse and, thus, for a corresponding location on the surface, so that this relationship can be regarded as an equation for determining a fluence to be used for the pulse or a peak value $F_0$ or a corresponding pulse energy, on which the single-pulse ablation volumes or the modification function K, respectively, depend. This equation is then numerically calculated for each pulse, e.g. using a Newton method which is known to the person skilled in the art, for the relationship $F_0/F_{THR}$ and stored. This yields a usable ablation program, which includes a series of target locations, onto which the pulses of the laser beam 3 are to be directed, according to the preliminary ablation program, and includes a corresponding position- or coordinate-dependent fluence peak value $F_0$ or a corresponding pulse energy for each of the target locations.

By suitable control of a high-voltage supply of the excimer laser 7 and, thus, of the charging of capacitors in which the energy for one pulse is respectively stored, according to the ablation program and by simultaneously controlling the deflecting device 8, ablation can be effected in step S36, using laser pulses with a position- or coordinate-dependent pulse energy and, thus, fluence.

According to a further exemplary embodiment, the determination of the peak value of fluence may optionally be effected also during the actual ablation.

Figure 9:
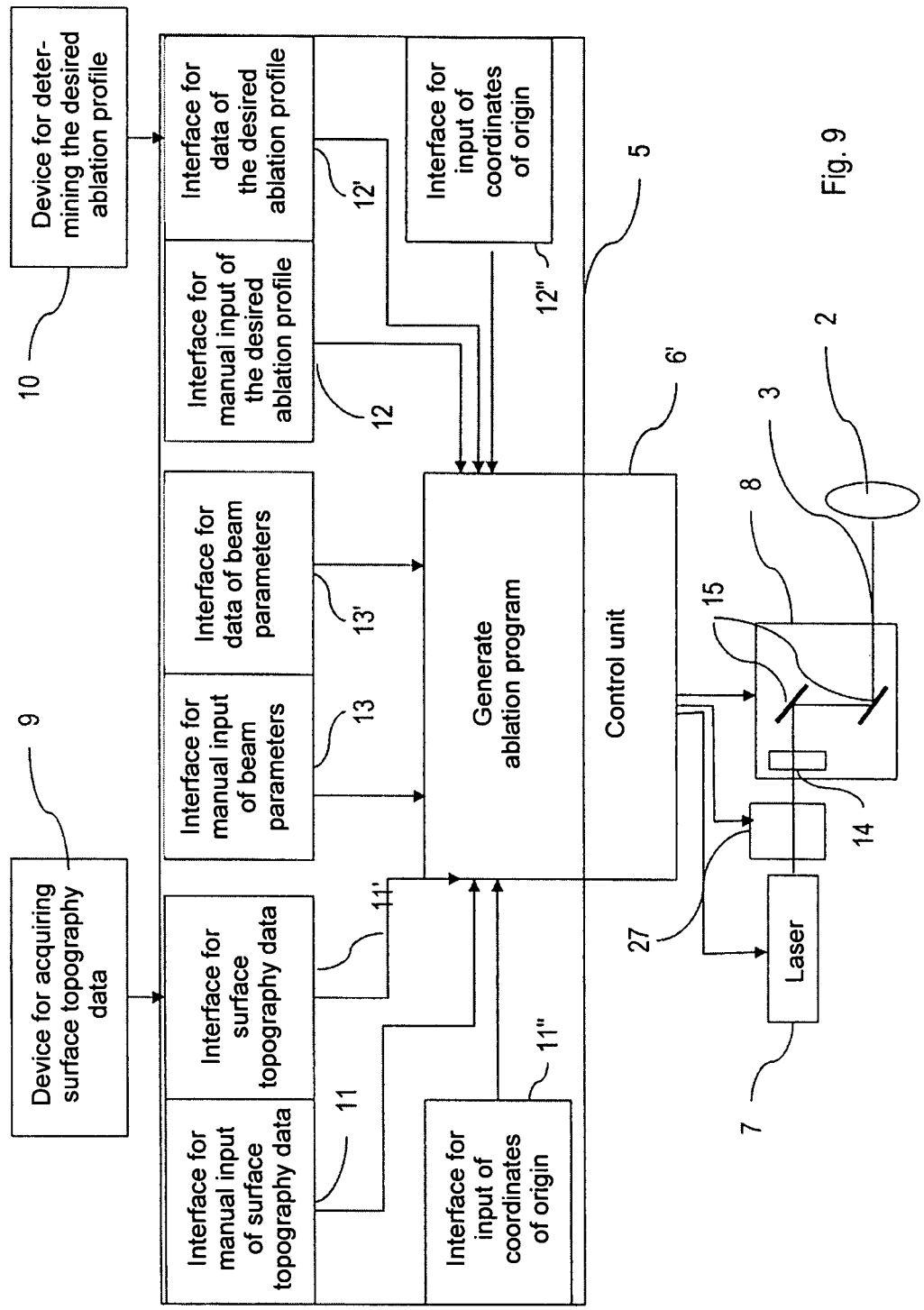
FIG. 9 shows a block diagram of a laser surgical instrument comprising an ablation device which includes a device for generating an ablation program according to a further preferred embodiment of the first aspect of the invention.

A variant of this exemplary embodiment is shown in FIG. 9. The instrument schematically shown here differs from the instrument of the previous exemplary embodiment in that the beam path of the laser beam 3 between the laser 7 and the deflecting device 8 includes a modulator 27, which is a liquid crystal element, in the present example, whose transmission can be controlled by the control unit 6'. Moreover, the control unit 6', compared to the control unit 6, comprises an output for control of the modulator 27, and the computer program executed in the data processing device 5 is provided to control fluence, not by controlling the laser 7, but by changing the transmission of the modulator 27.

The fluence of the laser 7 is then set such that the maximum fluence required for ablation according to the ablation program is achieved by maximum transmission of the modulator 27. During ablation in accordance with the ablation program, the modulator 27 is controlled such that the pulses impinging on the surface have the desired energy or fluence.

Figure 10:
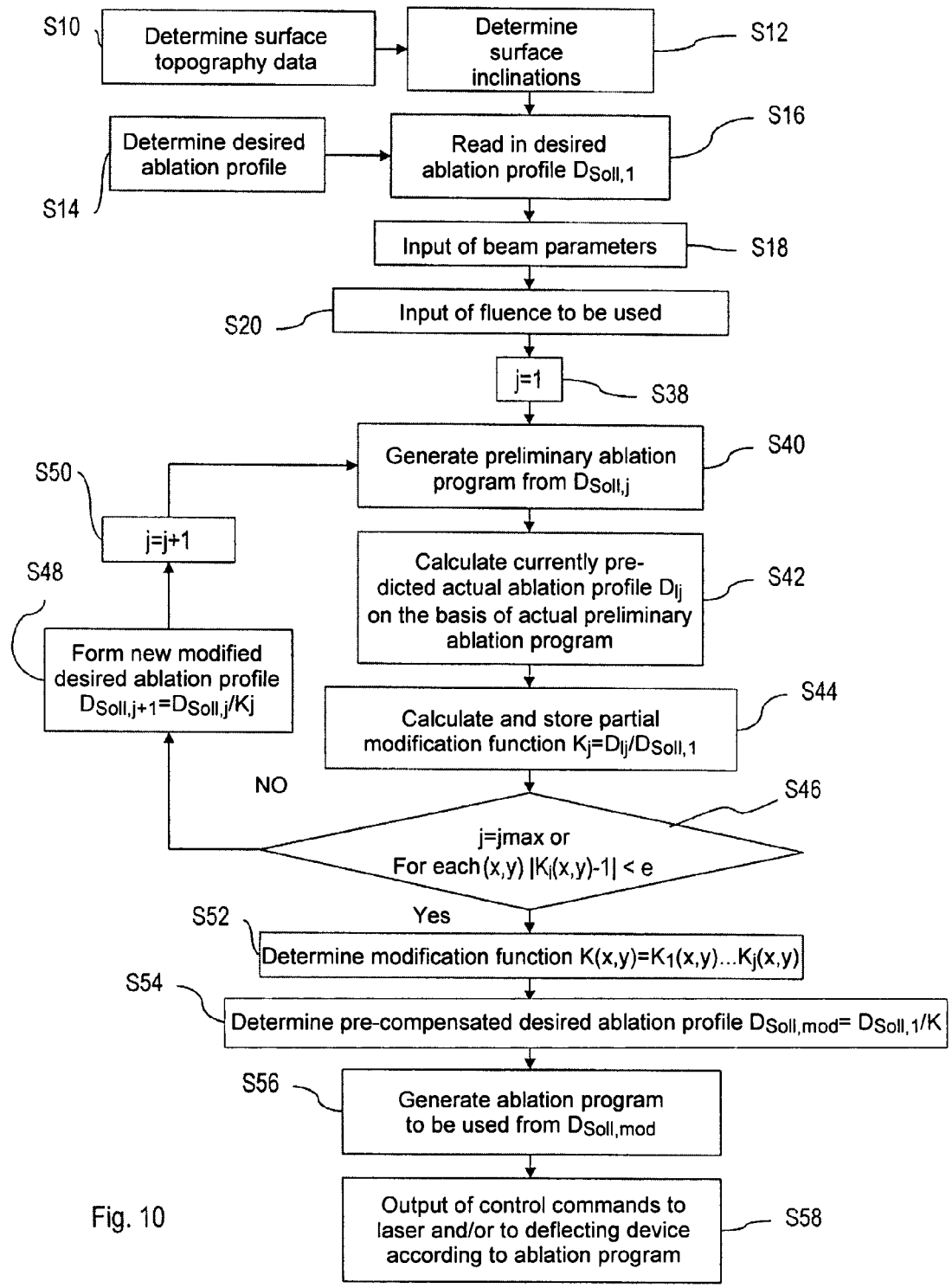
FIG. 10 shows a flow scheme of a method for generating an ablation program according to a further preferred embodiment of the first aspect of the invention.

FIG. 10 shows a further exemplary embodiment of a method for generating an ablation program which can be executed by an instrument that differs from the instrument 1 only by the way in which the data processing device 5 is programmed.

The method is identical with the method of the first exemplary embodiment in steps S10 to S20, so that the same reference numerals are used for these steps and the explanations apply accordingly. In this case, however, the ablation program is generated in an iterative manner, taking into consideration the shape of the beam profile with a spatial resolution of greater than the beam cross-section.

Starting out with a preliminary ablation program generated on the basis of the desired ablation profile, a predicted actual ablation profile $D_i$ is predicted with high spatial resolution. The N single-pulse coordinates are described by the coordinates $(x_{Pi}, y_{Pi})$, $i=1 \ldots N$. On a fine point grid of M×M points $(x_m, y_m)$, $m=1, \ldots, M$, for which $x_m-x_{m-1} \ll w$ and also $y_m-y_{m-1} \ll w$ hold true, the contribution of each of said N single pulses to the ablation depth is calculated with a spatial resolution that is better than the beam profile diameter:

$$D_I(x_m, y_m) = \sum_{\substack{i=1 \\ D_j>0}}^{N} D_i(x_m, y_m)$$

$$= \sum_{\substack{i=1 \\ D_j>0}}^{N} \left( \mu \ln \frac{F_0 \cos\theta(x_m, y_m)}{F_{thr}} - \mu \frac{(x_{Pi}-x_m)^2 + (y_{Pi}-y_m)^2}{w^2} \right)$$

Thus, the correct local angle of inclination $\theta$ is taken into consideration at each location of the ablation profile, and the fluence is reduced by $\cos\theta$. At the same time, the shape of the beam profile is taken into consideration. This predicted ablation profile is used after further steps for generating a further preliminary ablation program. More precisely, the following steps are carried out.

In step S38 a loop counter j is first set to the value 1 for the first iteration step.

In step S40, a preliminary ablation program is then generated in the first iteration loop j=1, from the desired ablation profile $D_{Soll}$, and in the subsequent iteration loops j=2, 3, ... from modified desired ablation profiles $D_{Soll,j}$ from the preceding iteration loop by means of a simple generating method in the current iteration loop j, wherein the shape of the beam profile and the inclination of the surface are not taken into consideration simultaneously when generating the ablation program. For this purpose, the above-mentioned method of DE 19727573 C1 can be used, for example.

In step S42, an actual ablation profile $D_{ij}$ is predicted, using the "blow-off" model, on the basis of the preliminary ablation program, as previously described. For this purpose, a grid of points of support in the x-y plane is used, which is considerably finer than the extent of the laser beam, thus allowing the shape of the beam to be resolved. For each pulse, an ablation depth is calculated at each corresponding point of support according to the "blow-off" model and according to the fluence actually effective there, i.e. the fluence of the laser beam corrected by the surface inclination, and if components of several pulses are incident on the same location, these ablation depths are summed up.

In the next step S44, values of a partial modification function $K_j = D_{ij}/D_{Soll,1}$ are then determined at the points of support, which function indicates how much the predicted actual ablation profile $D_{ij}$ deviates from the predetermined desired ablation profile $D_{Soll,1}$. The values are then temporarily stored. The function given by the values is computationally smoothened again by the use of a low-pass filter after the first computation.

In the next step S46 it is then verified whether the values of the modification function determined in step S44 and, thus, the ratio of the ablation profiles for all of the locations or points of support (x,y) under consideration, deviates from 1 by less than a predetermined error e, e.g. 0.05.

If such a deviation occurs, a further iteration loop is passed through by first forming a new, modified desired ablation profile $D_{Soll,j+1} = D_{Soll}/K_j$ in a step S48. Said profile then provides the basis for generating a new preliminary ablation program in the next step S40.

In step S50, the loop counter j is increased by 1. Following this, the next iteration loop is started in step S40.

On the other hand, if the partial modification function $K_j$ equals 1 sufficiently, step S46 of the method is followed by step S52, in which the value of a modification function $K(x,y) = K_1(x,y) \ldots K_j(x,y)$ is determined for each location or for each point (x,y) from all values determined for the partial modification functions $K_j$ in the iteration loops.

In step S54, a pre-compensated desired ablation profile $D_{Soll,mod}$ is determined from the predetermined desired ablation profile $D_{Soll,1}$ in that the desired ablation depth defined by $D_{Soll,1}$ for all points (x,y) is divided by the corresponding value of the modification function K for the location.

As in step S26 of the first exemplary embodiment, the ablation program to be used is generated in step S26 on the basis of the pre-compensated desired ablation profile $D_{Soll,mod}$. By said pre-compensation, i.e. modification using the modification function K, the predetermined desired ablation profile is modified such that any errors that would occur when using the simple generating method to generate an ablation program directly from the predetermined desired ablation profile by not considering the influences of the beam profile shape and of the surface inclination are compensated for already prior to said generation, i.e. the generated ablation program intended for use leads to the desired ablation profile to be achieved with very good approximation in the case of an ablation according to the program.

In step S 58, suitable control commands can then be output to the laser 7 and/or the deflecting device 8 according to the ablation program in order to ablate the desired ablation profile to be achieved from the surface.

Figure 11A:
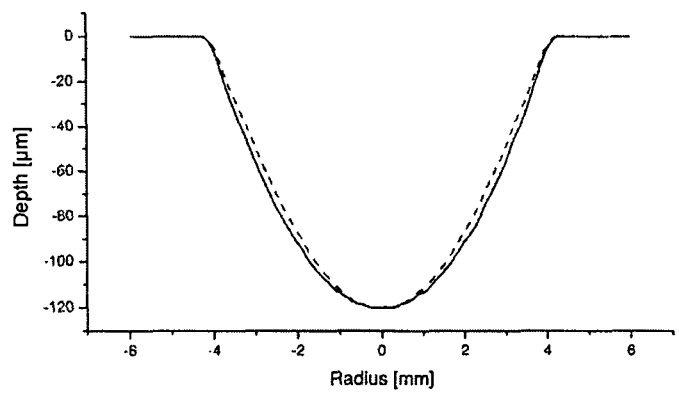
FIGS. 11a and b show diagrams for comparison of ablation depths achieved by ablation using the method according to FIG. 10 and using a known method.
Figure 11B:
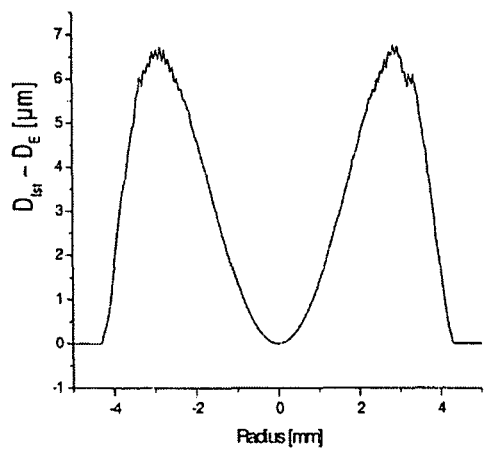

FIG. 11a shows a horizontal curve of intersection through the center of the spherical ablation profile over a region having a diameter of 8 mm to be ablated from a sphere having a radius of 7.86 mm. The solid line indicates the predicted actual profile $D_E$ that would result in case of a surface not inclined relative to the laser beam 3, whereas the broken line indicates the actual ablation profile $D_{I,1}$ taking the inclination and the beam profile shape into consideration. FIG. 11b shows the difference between these two curves.

FIG. 5 compares the result of the method according to the last exemplary embodiment with the results of the two previously described methods. In this case, the modification after a complete cycle of a first iteration is indicated by black squares. As can be seen, the deviations from the modification factor that does not take the shape of the beam profile into consideration are again considerably greater at a greater distance from the center of the calotte, i.e. at greater angles of inclination, so that this method is expected to yield improved ablation results.

It has been shown that a sufficiently good pre-compensation of errors is already achieved if only one iteration is carried out, i.e. by setting j=1. Therefore, a modified embodiment omits steps S38 and S46 to S52, with step S44 directly determining the values of the modification function K which then corresponds to the first partial modification function. The ablation program is then generated particularly quickly. The data processing device 5 and, thus, the generating device is programmed accordingly to carry out the method.

In the preceding exemplary embodiments, it was assumed that the data of inclination and the data for the desired ablation profile are given in the same coordinate system. However, this is not necessary. Rather, a modified method allows to input data at the start which indicate the relative position of the origins of the corresponding coordinate systems, so that after the corresponding data have been read in, the inclination data and the desired ablation profile can be easily transferred to a common coordinate system by simple shifting.

Figure 12:
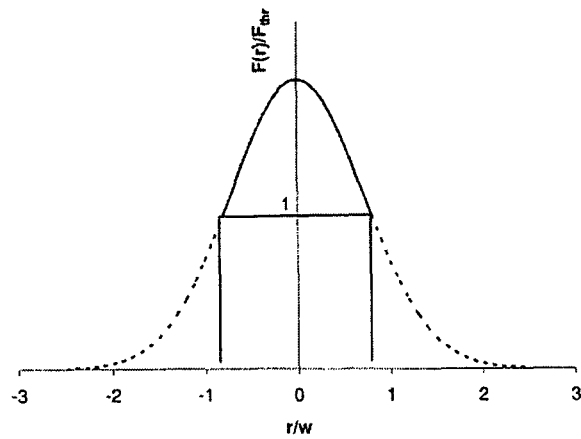
FIG. 12 shows a diagram in which a ratio of a fluence and a threshold value for said fluence is shown as a function of the radius in the laser beam for a Gaussian beam profile and a truncated Gaussian beam profile.

In a further embodiment of the method according to the invention, use is made of a beam having a particularly favorable beam profile shape at the surface to be ablated. The beam profile is shaped such that all regions of the two-dimensional fluence distribution or energy distribution are located above the threshold value $F_{thr}$ for ablation. An example of such beam profile is shown in FIG. 12. The beam profile results from a Gaussian profile in which the edges have been cut off according to the aforementioned criterion.

If such beam profile is used, the entire beam cross-section has an ablating effect at the surface so that a thermal load on adjacent regions can be minimized.

The shape of such beam profile can be caused by a stop which cuts off the desired parts of an output beam profile. In such case, the part of the laser energy incident on the stop is not used, which is a disadvantage in energy-critical applications. However, the effect of the reduced thermal load on the surface to be processed is present here as well.

For shaping the beam profile, use is preferably made of a micro-optical element which generates the desired intensity distribution directly in a diffractive or refractive manner. WO99/20429 A1 and DE 19623749 A1 describe corresponding micro-optical elements for generating a Gaussian intensity distribution. For example, a static refractive microlens array can be used wherein a predetermined angle distribution of the radiation is defined by the size distribution of the microlenses. The microoptical element re-arranges the incident laser beam with great efficiency such that the resulting re-shaped beam profile corresponds to the desired intensity distribution, but without losing any energy or power components.

This allows not only to reduce the thermal load on the surface to be processed, but also considerable energy savings, which is particularly advantageous in applications where the radiation energy of the laser is critical. In case of a cut-off ("truncated") Gaussian profile whose peak fluence amounts to four times the threshold fluence and whose fluence components below the threshold fluence are discarded, approximately 25% of energy can be saved as compared to the complete Gaussian profile with the same ablation effect. This also means that thermal heating of the surface to be processed, or of tissue in the case of treatment of an eye, is not translated to heat, which may be a great advantage especially in the field of corneal surgery. Such beam profiles can be employed in any spot scanning ablation method and, in particular, also in the ablation methods according to the invention.

A laser surgical instrument 101 for treatment of a patient's eye 2 according to a first preferred embodiment of the invention's second aspect is applied in a similar manner as the instrument 1 for carrying out a refractive correction in the eye and insofar replaces the instrument 1 of FIG. 1. Accordingly, as in FIG. 1, the instrument 101 emits a pulsed laser beam 3 onto the eye 1 of the patient whose head is fixed by a head support 4 that is securely connected to the instrument 101.

Figure 13:
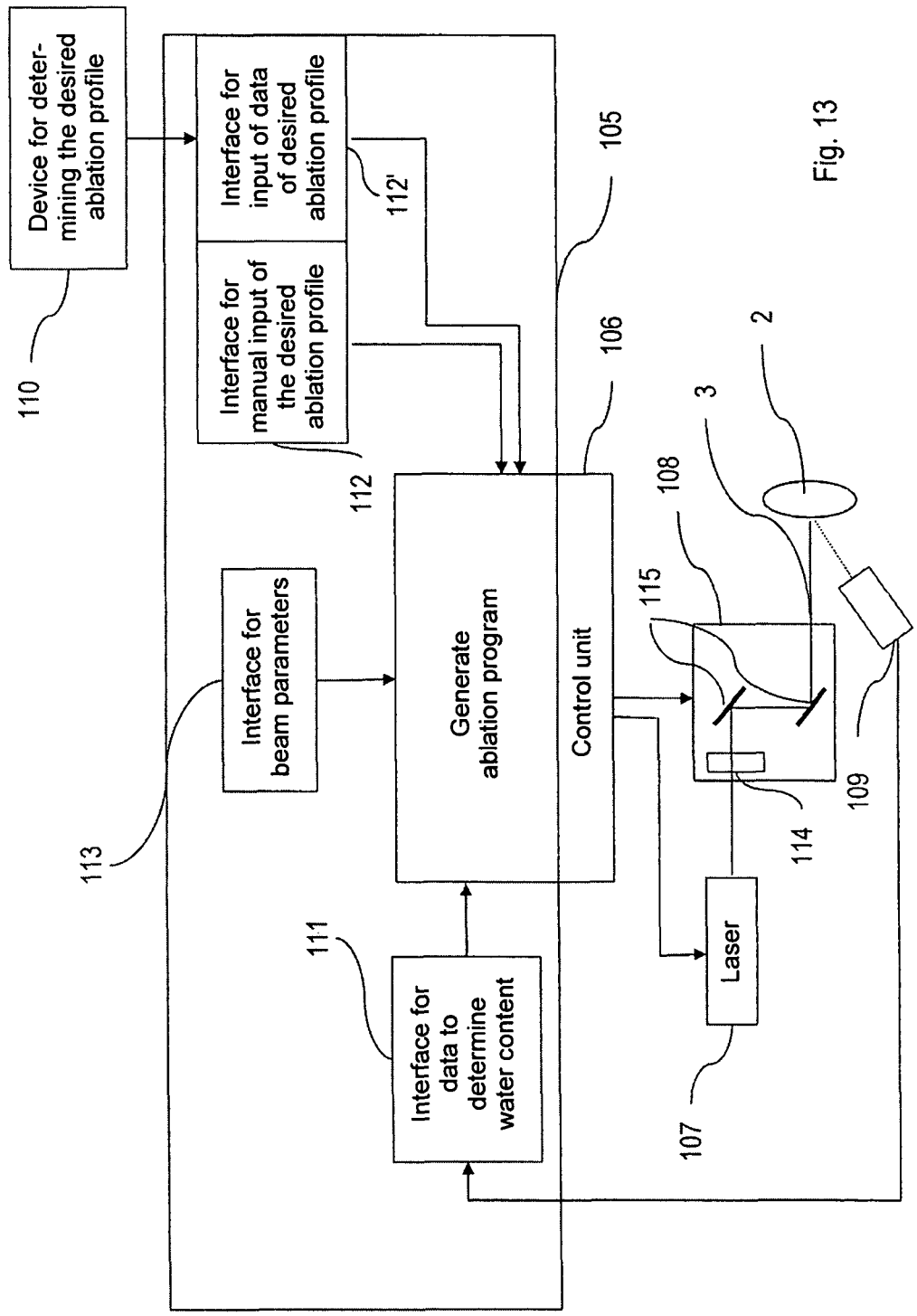
FIG. 13 shows a schematic block diagram of the laser ablation device comprising a signal-generating device according to a first preferred embodiment of a second aspect of the invention.

FIG. 13 schematically shows in more detail the design of the instrument which is a laser ablation device. The instrument comprises a data processing device 105 with an integrated control unit 106, a laser 107 controlled by the control unit 106 and a deflecting device 108, which is also controlled by the control unit and by means of which the pulsed laser beam 103 emitted by the laser 107 can be directed and focused on target locations on the cornea of the eye 2 according to a given ablation program.

The instrument further comprises a device 109 for acquiring water content measurement data, from which the water content of a region to be treated in the eye 2, more specifically the cornea, can be determined, and a device 110 for determining a desired ablation profile. Both devices are coupled to the data processing device 105. The data processing device 105, the control unit 106, the device 109 for acquiring water content measurement data and the device 110 for determining the desired ablation profile form a device for generating an ablation program according to a first preferred embodiment of the invention's second aspect.

The data processing device 105 with integrated control unit 106 serves to generate an ablation program by the use of data from which the water content in the material of the region to be treated can be determined, data relating to the properties of the laser beam 3, and data relating to the desired ablation profile to be ablated. For this purpose, the data processing device 105 comprises a processor and a memory for storing data in which, in particular, a computer program including program code is also stored, which code, when the program is executed on the processor, allows to generate the ablation program and to generate control signals using the integrated control unit 106 to control the laser 107 and/or the deflecting device 108, which signals are output to the laser 107 or to the deflecting device 108 so as to carry out the actual ablation. The memory and the processor are partially illustrated in the block diagram by the block "generate ablation program".

For this purpose, the data processing device 105 comprises interfaces for data input, namely an interface 111 for input of water content measurement data from the device 109 for acquiring water content measurement data, an interface 112 for manual input of the desired ablation profile, and an interface 112' for reading in data relating to the desired ablation profile from the device 110 for determining the desired ablation profile. Moreover, an interface 113 for input of beam parameters for the laser beam 3 is provided. In this exemplary embodiment, the interface 113 is provided as an interface for manual input.

In physical terms, the interfaces for manual input may be one single interface to which, although not shown in the Figures, a keyboard and a screen, on which an input prompt can be displayed when corresponding data are to be read in, are connected. The interfaces further comprise corresponding modules of the computer program for reading in data from the keyboard.

The other interfaces 111' and 112' are conventional interfaces for data streams which, in addition to corresponding electronic modules, also comprise software modules.

The control unit 106 is integrated into the data processing device 105 and further comprises interfaces, not shown in the Figures, for output of control signals to control the laser 107 and the deflecting device 108. Such control units are basically known and therefore need not be explained in more detail.

The laser 107 is connected to the control unit 106 and emits a pulsed laser beam with predetermined pulse energies as a function of the ablation program. For example, an excimer laser having a wavelength in the wavelength range of 193 nm can be used.

The deflecting device 108 is also connected to the control unit 106 via a data link and, in accordance with control signals from the control unit 106, directs the pulsed laser beam 3 emitted by the laser 107 onto predetermined target locations on the surface of the eye 2 according to the ablation program to be executed. For this purpose, the deflecting device 108 comprises a focusing device 114 for focusing the laser beam along its direction of propagation and for deflection transverse to the laser beam via two mirrors 115, which are rotatable or tiltable about two mutually orthogonal axes and are arranged in the beam path following the focusing device 114.

Both the laser 107 and the deflecting device 108 may be conventional, known devices of a laser surgical instrument.

In order to indicate the water content and the desired ablation profile, two parallel Cartesian coordinate systems are used whose x-y planes coincide. If possible, the z axis is aligned parallel to the optical axis of the eye with good approximation. In the example, it is assumed for the sake of easier illustration that the origins of the coordinate systems coincide so that the coordinate systems coincide and are not distinguished any more in the following. If the coordinate origins do not coincide, the relative position can be manually input after reading in the data relating to the water content or the desired ablation profile, following which the data can be transferred to a common coordinate system. A corresponding interface for input of the relative position may then be provided. FIG. 3 shows the position of the coordinate system for a spherical body or a sphere having a surface 2' as a simplified model of the eye 2. The z-axes are defined during alignment of the eye 2 relative to the instrument 101, for which purpose a fixating light not shown in the Figures may be used, for example.

In the example, the device 109 for acquiring water content measurement data comprises a device for confocal Raman spectroscopy of the cornea of the eye as described, for example, in "Assessment of Transient Changes in Corneal Hydration Using Confocal Raman Spectroscopy", Brian T. Fischer et al., Cornea 22 (4), pages 363-370, 2003. The region of the cornea of the eye 2 intended for processing is scanned with a suitable laser beam that is focused both in depth and also laterally of the laser beam. Raman radiation coming from the eye 2 is then confocally detected so that the intensity of the Raman radiation can be detected for different locations in the volume to be ablated. The data indicating intensity, i.e. the water content measurement data, are input for each measured location to the data processing device 105 via the interface 111. The computer program in the data processing device 105 comprises program code by means of which the data can be converted to data describing the water content at the respective location.

In the present example, the device 110 for determining the desired ablation profile comprises a wavefront analyzer of the Hartmann-Shack type as well as, where appropriate, devices for determining the refractive power of the eye 2, by which analyzer or devices, respectively, a desired ablation profile $D_{Soll}$ for the region to be treated in the eye 2 can be determined according to known methods. In doing so, the desired ablation profile is determined such that correction of imaging errors in the eye 2 can be achieved as far as possible by the ablation to be carried out. An example of the desired ablation profile is evident from FIG. 3. It is given by the distances, in the direction of z, between the initial surface, the calotte 2', and a desired surface 2" indicated by a broken line, as a function of the location in the x-y plane. A region to be ablated is formed by the volume between the surface 2' before ablation and the desired surface 2", the latter being formed by the desired ablation profile.

In order to determine the desired ablation profile, the device 110 may comprise a suitable processor which evaluates data relating to the refractive power of the eye 2 and the wavefront data in order to determine the desired ablation profile again, in the present example, in the form of the desired ablation depths for locations of support in the form of points of a point grid in the x-y plane of the corresponding coordinate system which coincides with the x-y plane of the coordinate system for indicating the ablation profile. As far as the coordinate origins are not identical, the position of one of the reference points or coordinate origins in the respective other coordinate system can be given so that the data can be transformed by simple shifting into an identical coordinate system during a later process stage. This may turn out to be favorable if the center of the desired ablation profile, i.e. a point relative to which the desired ablation profile is approximately symmetrical, deviates from the center of the surface of the eye 2, i.e. from a point relative to which the surface of the eye is approximately symmetrical. Such a method for generating a desired ablation profile is described, for example, in WO 01/08075 A1, the respective contents of which are hereby incorporated in the description by reference.

The method for generating an ablation program according to the first exemplary embodiment of the invention's second aspect is based on the following considerations.

In order to ablate the desired ablation profile $D_{Soll}$ from the eye 2, laser pulses having a predetermined pulse energy are emitted onto predetermined target locations according to a generated ablation program, each of said laser pulses individually leading to a removal of material. The depth of removal by a pulse can be described by various models. In the present example, the so-called "blow-off" model is used, as described, for example, in "Refraktive Chirurgie der Hornhaut", Theo Seiler (Ed.), 1st edition, ENKE Georg Thieme Verlag, Stuttgart/N.Y., 2000 (ISBN 3-13-118071-4), Chapter 6.1, p. 150, or in R. Srinivasan: "Ablation of Polymers and Biological Tissue by Ultraviolet Lasers", Science vol. 234, p. 559-565, 31 Oct. 1986.

Following this, material is removed to a depth $D_p$ at a location having the coordinates (x, y), by laser radiation impinging at this location and having an effective fluence F(x,y), i.e. energy per surface area, according to the following formula:

$$D_P(x, y) = \begin{cases} \mu \cdot \ln\frac{F(x, y)}{F_{thr}}, & \text{if } F(x, y) > F_{thr} \\ 0, & \text{otherwise.} \end{cases} \quad (1)$$

In this formula, $\mu$ designates a material-dependent ablation coefficient and $F_{thr}$ designates a likewise material-dependent ablation threshold fluence value, below which value laser radiation no longer results in material removal from the eye 2.

In the simple generating method for an ablation program used below, it is assumed that the desired ablation profile can be split into single-pulse ablation volumes which form upon impingement of a pulse. In this case, generating the ablation program includes determining the target locations (x,y) onto which the pulses of a predetermined pulse energy have to be directed.

In generating an ablation program, it is assumed that a laser pulse removes a single-pulse or spot ablation volume $V_{pulse}$ which is obtained as an integral of the ablation depth $D_p$ over the entire pulse area:

$$V_{pulse} = \iint_{Spot} D_P(x, y) dx dy = \mu \iint_{Spot} \ln\frac{F(x, y)}{F_{thr}} dx dy. \quad (2)$$

The integral extends over the area designated as "Spot", in which $D_p > 0$ holds.

In the following, the surface area in which $D_p > 0$ applies is assumed to be constant and to have an area $d^2$, in which case $V_{pulse} = d^2 D_p$.

In simple generating methods in which the water content of the material to be ablated and, in particular, variations in the water content of the material to be ablated are not taken into consideration, the ablation depth $D_{P,0}$ of a pulse without taking the water content into consideration results as follows:

$$D_{P,0} = \mu_0 \cdot \ln\left(\frac{F_0}{F_{thr}}\right). \quad (3)$$

$\mu_0$ designates an empirically determined ablation rate which is assumed to be constant. In this case, the empirical determination can be effected by testing ablation on a larger number of different eyes, i.e. on their cornea.

Figure 14:
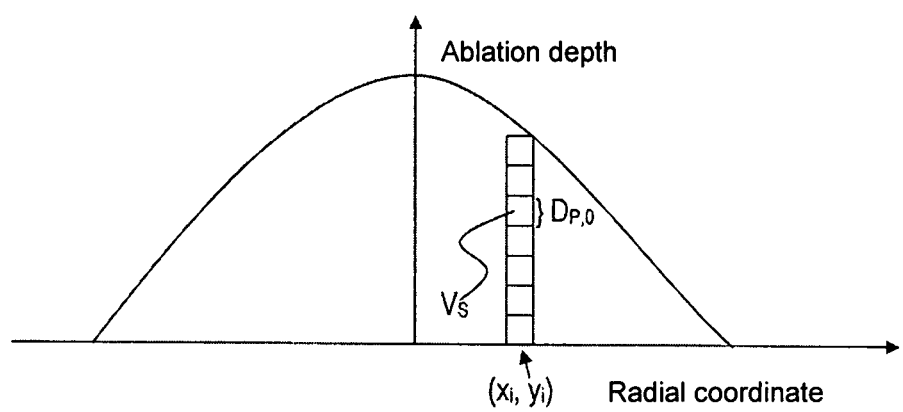
FIG. 14 shows a schematic representation of a sectional view of a desired ablation profile taken along a diameter through the body in FIG. 3 and of single pulse ablation volumes.

When using a simple method to generate an ablation program, it is assumed that each pulse emitted onto the same location ablates the same single-pulse volume or the same single-pulse ablation depth $D_{P,0}$, said volumes adding up. This is illustrated in FIG. 14a. This Figure schematically shows, by way of example, a desired ablation profile along a diameter through the eye 2, approximately along the x-axis. The single-pulse ablation volumes $V_S$ are successively ablated and result in the desired ablation depth, with each single-pulse ablation volume $V_S$ corresponding to a single-pulse ablation depth $D_{P,0}$. If the coordinates of the target locations considered are designated by $(x_i, y_i)$, i=1, ..., G, G being a natural number, the number $N_{i,0}$ of pulses to be emitted to a target location $(x_i, y_i)$ is obtained as:

$$N_{i,0} = \frac{D_{ideal}(x_i, y_i)}{D_{P,0}}. \tag{4}$$

However, the ablation rate μ actually depends on the water content H in the material to be ablated. In the example, a model based on the blow-off model yields the single-pulse ablation depth $D_{P,W}$ of a pulse—taking the water content of the material into consideration—as $$D_{P,W} = \mu(H) \cdot \ln\left(\frac{F_0}{F_{thr}}\right), \tag{5}$$

wherein the ablation rate μ(H) depending on the water content H may be assumed, for example, to be proportional to the water content H with a proportionality constant k:

$$\mu(H) = k \cdot H. \tag{6}$$

The value of the proportionality constant k is selected such that, for a mean water content $H_m$ of the cornea determined in the above surveys, $k \cdot H_m = \mu_0$ holds true.

However, the water content of the material or tissue to be ablated from the cornea may, in fact, change as a function of ambient conditions, such as air humidity, air stream above the eye, air temperature, and of the ablation conditions, e.g. the ablation rate, the number of pulses being emitted onto a target location $(x_i, y_i)$ or already emitted in its vicinity, and the fluence of the pulses. In this exemplary embodiment, the following model for the water content H of material to be ablated above a target location $(x_i, y_i)$, onto which $n(x_i, y_i)$ pulses have already been emitted, will be assumed:

$$H(x_i, y_i; n(x_i, y_i)) = a(x_i, y_i) + b \cdot \log(n(x_i, y_i)). \tag{7}$$

The parameter a describes the water content at the target location $(x_i, y_i)$ prior to the start of ablation. This water content may depend, for instance, on the type of treatment, e.g. photo-refractive keratectomy, LASIK, LASIK with photo-disruptive generation of a foldable cornea cover, or LASEK, the properties of the individual eye and the ambient conditions of ablation. The parameter b, which is assumed to be constant in this exemplary embodiment, describes the change in water content effected by emitting pulses onto the location $(x_i, y_i)$. In particular, the parameter b may be obtained empirically by survey experiments.

When $N_{W,i}$ pulses are emitted onto the same target location $(x_i, y_i)$, the single-pulse ablation depths, which are now no longer constant due to their dependence on the water content H, add up to a total depth. The number of $N_{W,i}$ can be determined such that particularly the desired ablation depth $D_{Soll}(x_i, y_i)$ is achieved at the location $(x_i, y_i)$:

$$D_{ideal}(x_i, y_i) = \sum_1^{N_{W,i}} D_{P,W} \approx \int_0^{N_{W,i}} D_{P,W}(u) du. \tag{8}$$

As shown in equation (8), when a large number of pulses are emitted onto the same location, the sum may be replaced with an integral by approximation so as to enable approximate, but quicker computation of the sum.

Since the ablation rate increases as the number of pulses increases, the ablation depth actually achieved by emitting $N_{W,i}$ pulses onto the location $(x_i, y_i)$ changes with each pulse and differs from $N_{i,0}$-times the single-pulse ablation depth $D_{P,0}$ in the simple model in which the water content is not considered.

Therefore, in order to enable the use of a simple, e.g. known, method which does not take the water content into consideration, for generating the ablation program, a modification function M is defined which serves to compute a pre-compensated or modified desired ablation profile $D_{Mod}$ from the predetermined desired ablation profile $D_{Soll}$:

$$D_{Mod}(x_i, y_i) = M(D_{Soll}(x_i, y_i)) D_{Soll}(x_i, y_i) \tag{9}$$

with $$M(D_{Soll}(x_i, y_i)) = \frac{N_{W,i}}{N_{i,0}} = \frac{N_{W,i} D_{P,0}}{D_{Soll}(x_i, y_i)}. \tag{10}$$

As expressed in formulae (9) and (10), the modification function depends on the desired ablation depth $D_{Soll}(x_i, y_i)$, on the parameter a and, thus, on the water content of the material prior to ablation, as well as on the parameter b and, thus, on the change in water content by said ablation. Moreover, there is a dependence on the model for $D_{P,0}$ used in the simple generating method.

In particular, the ablation effect of a single pulse may increase as the number of pulses emitted onto the same location increases, so that for a great desired ablation depth which requires a larger number of single pulses at the same location, fewer single pulses are to be used than would be expected according to the formula (4).

Now, if a simpler generating method is used to generate the ablation program from the pre-compensated desired ablation profile $D_{Mod}$, the factor M contained in $D_{Mod}$ compensates precisely those errors which result from not taking the water content into consideration in formula (3), so that when effecting ablation by an ablation program generated from the pre-compensated desired ablation profile by means of the simple generating method, the predetermined desired ablation profile is achieved with good approximation.

In order to determine the locations onto which the laser pulses are to be emitted, various known simple generating methods can be used, e.g. the methods described in DE 19727573 C1 and EP 1060710 A2. In DE 19727573 C1, ablation is effected in layers, i.e. locations of impingement are determined in a layer-wise fashion for pulses, with the desired profile then resulting from superposition of these layers. According to the method in EP 1060710 A2, the spot distance is varied in a quasi-continuous manner in order to achieve the desired ablation depth.

Figure 15:
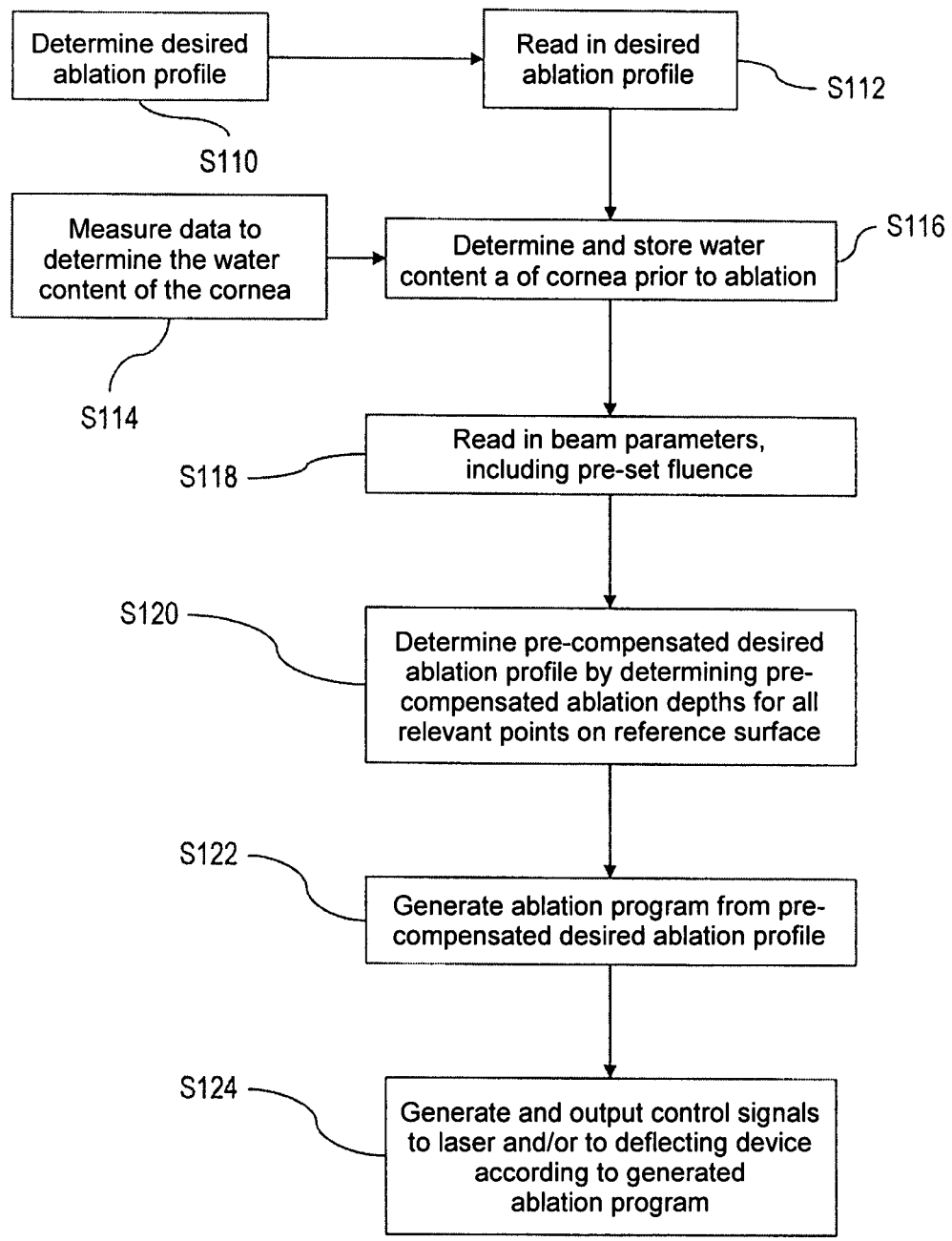
FIG. 15 shows a flow scheme of a method for forming control signals according to a first ablation program generated by said method for the instrument in FIG. 13 according to a first preferred embodiment of the second aspect of the invention.

In order to determine the ablation program, the method steps schematically shown in the flow scheme of FIG. 15 are carried out, for which purpose the computer program executed in the data processing device comprises suitable program code.

First of all, the desired ablation profile $D_{Soll}$ is determined in step S110 using the means 110 for determining the desired ablation profile. This determination is activated here by a user. In another exemplary embodiment, the data processing device 105 outputs a corresponding control signal to the means 110 for determining the desired ablation profile, via a control interface not shown in the Figures, to automatically start said determination. For said determination, imaging errors are determined from wavefront data. Known methods are used to calculate at which locations on surface of the eye material is to be ablated to what depth. In the present example, the desired ablation profile $D_{Soll}$ is given by specifying the desired ablation depth as a function of the location on a grid in the x-y plane.

In step S112, these data are then read, via the interface 112', into the data processing device 105 and stored there in its memory.

In step S114, i.e. after steps S110 and S112 in the example, but also prior to these steps in other embodiments, intensities of Raman radiation are detected in a space-resolved manner by means of confocal Raman spectroscopy as water content measurement data, and data indicating these intensities are transmitted to the data processing device 105 together with corresponding position coordinates. This determination is activated here by a user. In another exemplary embodiment, the interface 110 is also provided as a control interface, and the data processing device 105 outputs a corresponding control signal to the device 109 via said control interface 110 so as to automatically start said determination.

In step S116, the water content measurement data are read in via the interface 110 and temporarily stored in the memory of the data processing device 105. Water content values a are then determined from the intensities for all locations for which water content measurement data have been acquired and these values are stored in a form assigned to the locations.

In step S118, beam parameters of the laser beam 3 to be used are then read in via the interface 113. In this exemplary embodiment, the diameter of the beam profile of the laser beam 3 is input for this purpose. The shape of the laser beam 3 is assumed to be constant over the beam cross-section and fixed and is taken into consideration in the form of corresponding formulae in the program being executed on the processor of the data processing device 105. Further, the pulse energy to be used per surface area, or the fluence $F_0$ to be used, is input and stored.

In step S120, a pre-compensated desired ablation profile $D_{Mod}$ is then determined from the predetermined desired ablation profile $D_{Soll}$. For this purpose, the following two partial steps are carried out for all supporting locations at which the desired ablation profile is given: The values for the proportionality constant k and the threshold value for the fluence $F_{thr}$ are stored in the program code. If ($x_i$, $y_i$) designates the location, the equation given by formula (8) is resolved for the pulse number $N_{W,i}$ using the desired ablation depth $D_{Soll}$ ($x_i$, $y_i$) given by the desired ablation profile and using the values $a(x_i, y_i)$, b, k and $F_0/F_{thr}$, for example by means of a Newton method for resolving non-linear equations. If a is not present at the location ($x_i$, $y_i$), a corresponding value can be obtained by interpolation. The value $M(D_{Soll}(x_i, y_i))$ of the modification function M is then determined according to formula (10).

In the subsequent partial step, in order to obtain a pre-compensated desired ablation depth $D_{Mod}$ at the location ($x_i$, $y_i$), the predetermined desired ablation depth $D_{Soll}(x_i, y_i)$ is multiplied by the value $M(D_{Soll}(x_i, y_i))$ of the modification function and stored as $D_{Mod}(x_i, y_i)$, assigned to the location ($x_i$, $y_i$).

The pre-compensated desired ablation profile $D_{Mod}$ is then given by the locations ($x_i$, $y_i$) and the pre-compensated desired ablation depths $D_{Mod}(x_i, y_i)$ assigned to them.

In the next step S122 an ablation program is generated on the basis of the modified desired ablation profile $D_{Mod}$, the input fluence and the other beam parameter as well as formula (3), for which purpose a method is used that, therefore, does not take the water content of the tissue or the change in the water content of the tissue into consideration during ablation. For example, the method described in DE 19727573 C1 can be used. The ablation program thus generated comprises a sequence of target locations in the x-y plane, i.e. corresponding coordinates onto which the laser pulses have to be directed with the pulse energy determined by the fluence read in, in order to achieve the desired ablation profile to be achieved. The ablation program is stored in the data processing device 105. This step completes the actual generation of the ablation program.

In the next step S126, control commands are output to the laser 107 and to the deflecting device 108 by the data processing device 105 with the integrated control unit 106 in order to remove material from the eye 2 according to the generated ablation program.

The ablation method is suitable for both photorefractive keratectomy and LASIK. Since these methods involve the removal of material in different layers of the eye, the use of different desired ablation profiles may be accordingly required in some cases.

Figure 16:
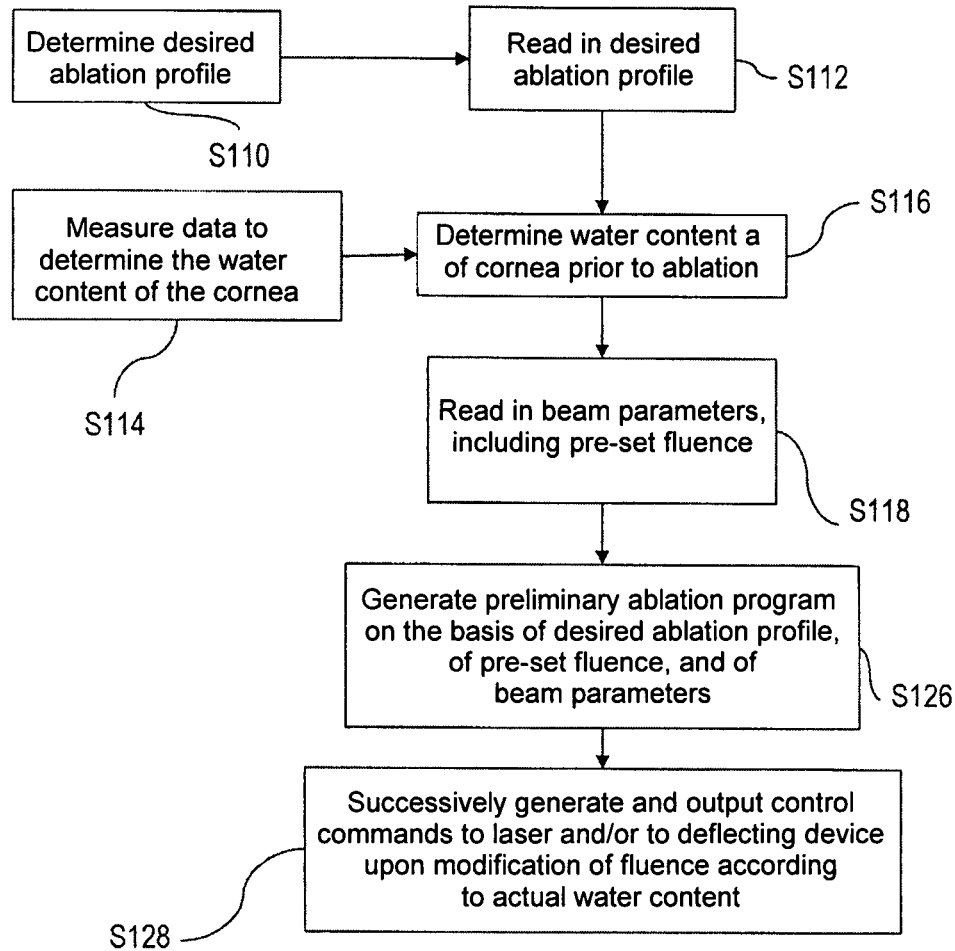
FIG. 16 shows a flow scheme of a method for forming and emitting control signals according to an ablation program generated by said method according to a further preferred embodiment of the second aspect of the invention.
Figure 17:
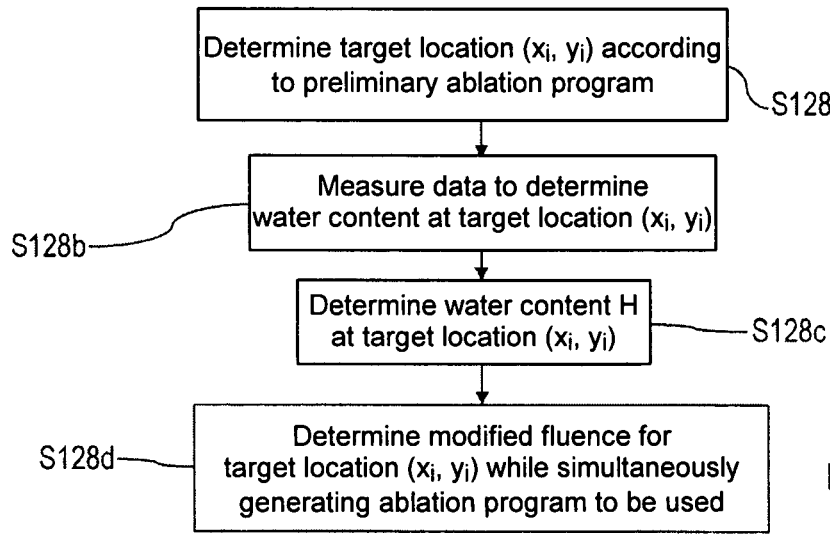
FIG. 17 shows a flow scheme comprising partial steps of step S128 according to the flow scheme of FIG. 16.

A second exemplary embodiment of a method for forming and emitting control signals for ablation according to an ablation program generated by said method is shown in FIGS. 16 and 17. A corresponding signal-forming device differs from the signal-forming device according to the first exemplary embodiment of the invention's second aspect only in the programming of the data processing device 105 and, in that respect, only in that the latter can perform the method described below for forming control signals or for generating an ablation program, respectively. The method differs from the first method substantially in that the fluence of pulses of the pulsed laser beam is now changed according to the water content. Moreover, this is done during emission of the control signals and, thus, during ablation.

The method for forming and emitting control signals, which encompasses the method for generating an ablation program, comprises several steps which correspond to those of the signal-forming or generating method shown in FIG. 15. Therefore, these will be referred to below by the same reference numerals and will not be described in detail again.

Thus, in steps S110 and S112 or S114 and S116, respectively, data relating to the desired ablation profile or to the water content of the corneal tissue, respectively, are determined and stored prior to ablation.

In step S118, which follows then, a beam cross-section and a pre-set initial fluence value $F_0$ are input.

In the next step S126, a preliminary ablation program is then generated on the basis of the read-in desired ablation profile, the input pre-set fluence and the beam parameter, the simple generating method used for this purpose not taking the water content of the cornea or variations in said water content into consideration. In particular, the above-mentioned method of DE 19727573 C1 can be used. The preliminary ablation program which in turn comprises a series of coordinates for locations on the surface of the eye 2, onto which the pulses are to be directed, is then stored.

Following this, modified fluence values are determined for the corresponding pulses in step S128 from the series of target locations according to the preliminary ablation program, which values are assigned to the target locations while generating the ablation program to be used. After forming a modified fluence value, a control signal is formed directly and output to the laser 107 or the deflecting device 108, respectively. By suitable control of a high-voltage supply of the excimer laser 107 and, thus, of the charging of capacitors in which the energy for one pulse is respectively stored, according to the ablation program and by simultaneously controlling the deflecting device 108, ablation can be effected using a laser pulse with a position- or coordinate-dependent pulse energy and, thus, fluence.

This involves successive processing of the series of target locations. The corresponding partial steps for determining a modified fluence of a pulse to be emitted onto a target location $(x_j, y_j)$ are shown in FIG. 17.

In partial step S128a, the first target location is initially read out in the first pass; in subsequent passes, the next target location is read out according to the preliminary ablation program. The latter location has the coordinates $(x_j, y_j)$ with j being the ordinal number of the target location in the series.

In partial step S128b an acquisition of suitable data for the target location $(x_j, y_j)$ is then effected by controlling the device 109 for acquisition of water content measurement data through the data processing device 105 via a control interface which is not shown.

The data are input via the interface 111 and are converted in partial step S128c to a water content $H(x_j, y_j)$ at the target location $(x_j, y_j)$ by means of the data processing device.

In partial step S128d, a modified fluence value is then determined for the pulse to be emitted onto the target location $(x_j, y_j)$, which value is assigned to said target location. The modified fluence value together with the target location $(x_j, y_j)$ forms an element of the ablation program to be eventually used.

The fluence value is then modified such that ablation with the modified fluence achieves the single-pulse ablation depths that had been assumed as the ablation depth for a single pulse without taking the water content into consideration while generating the preliminary ablation program. Thus, based on above equations (1), (3) and (4), the equation $D_{P,W}(F)=D_{P,0}(F_0)$ has to be resolved with respect to F, wherein $D_{P,W}$ depends on the water content H at the target location via $\mu(H)$. Using the models according to equations (1), (3) and (4), the following equation is obtained for the modified fluence:

$$\frac{F}{F_{thr}} = \frac{F_0}{F_{thr}} e^{\frac{\mu_0}{\mu(H)}}. \tag{11}$$

This calculation can be carried out very quickly, so that partial step S28d can be passed through very quickly.

Suitable control signals for the laser 107 and the deflecting device 108 can be formed and output to the laser 107, i.e. the high-voltage supply of the laser 107, or to the deflecting device 108. The method is then resumed in partial step S128a for the next element of the preliminary ablation program. Like steps S110 to S122 above, steps S110 to S128d without the formation and emission of the control signals provide an exemplary embodiment of a generating method of the invention according to the invention's second aspect.

Thus, apart from the model for the ablation depth, no assumptions need to be made with respect to the water content of the cornea. In particular, unforeseen changes in water content can be fully taken into consideration during formation and emission of the control signals and, thus, during ablation.

Figure 18:
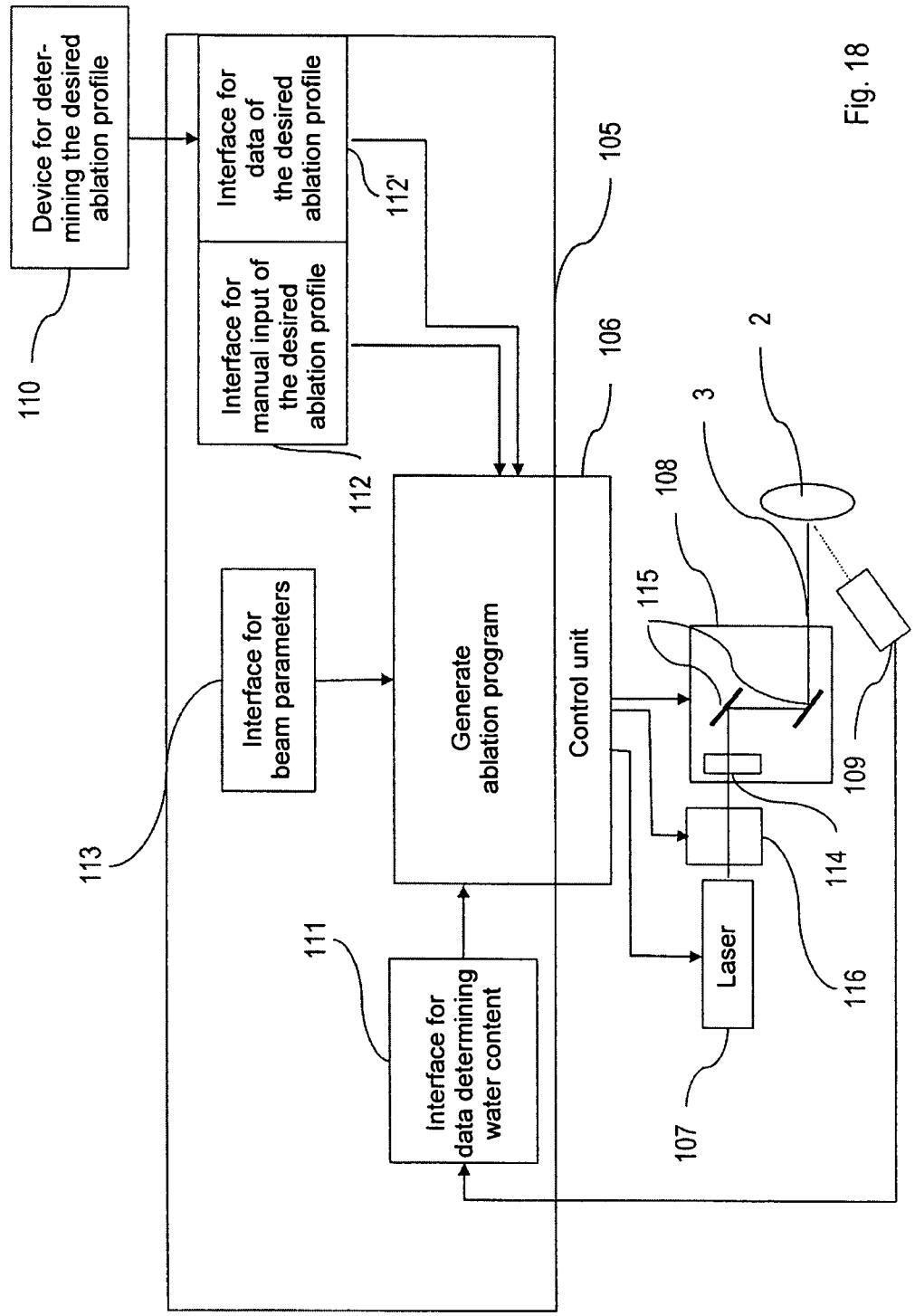
FIG. 18 shows a block diagram of an ablation device comprising a signal-forming device according to a third preferred embodiment of the second aspect of the invention for a laser surgical instrument.

A third embodiment which represents a variant of the above-described exemplary embodiment is shown in FIG. 18. The instrument schematically shown here differs from the instrument of the previous exemplary embodiment in that a modulator 116 which, in the present example, is a liquid crystal element whose transmission can be controlled by the control unit 106' is arranged in the beam path of the laser beam 3 between the laser 107 and the deflecting device 108. Moreover, the control unit 106', compared to the control unit 106, comprises an output for control of the modulator 116, and the computer program executed in the data processing device 105 is provided to control fluence, not by controlling the laser 107, but by changing the transmission of the modulator 116.

The fluence of the laser 107 is then set such that the maximum fluence required for ablation according to the ablation program is achieved by maximum transmission of the modulator 116. During ablation in accordance with the ablation program, the modulator 116 is controlled such that the pulses impinging on the surface have the desired energy or fluence.

In another variant, a beam-shaping device may be provided instead of the modulator 116, which device responds to signals from the control unit by modifying the beam cross-section and, thus, fluence.

In other embodiments of the above-described method, the ablation threshold value $F_{thr}$ for fluence may also depend on the water content H.

In a fifth preferred embodiment of a control signal-forming method of the invention according to the invention's second aspect, equation (9) is used directly in generating the ablation program, by giving a pattern of target locations and resolving equation (9) for each target location as a function of the number of pulses $N_{W,i}$ to be emitted.

In a sixth preferred embodiment of a signal-forming method according to the second aspect of the invention, the inclination of the surface of the cornea with respect to the laser beam 3 or to the z-direction is also taken into consideration, in addition to the water content, as an approximation for the direction of the laser beam 3 in combination with the actual shape of the beam profile. Insofar, this exemplary embodiment and modifications thereof, in particular, also represents an exemplary embodiment of the invention's first aspect. In the example, the laser beam 3 emitted by the laser 107 has a beam profile with a Gaussian shape.

Whereas conventional methods assume the effective fluence F(x, y) to be constant over the area of the pulse or of the spot, respectively, two further influences are now taken into consideration in addition to the influence of the water content. On the one hand, it is taken into consideration that the inclination of the surface to be processed reduces the effective fluence according to said inclination relative to the fluence of the laser beam 3. If the surface to be processed is described by a height function f(x, y), which indicates the height of the surface above the x-y plane, the angle of inclination θ of the surface can be determined relative to the z axis and, thus, in approximation to the laser beam 3 incident on the surface 2', according to the formula $$\theta(x,y)=\arctan(|\mathrm{grad}\, f(x,y)|) \tag{12}$$

Thus, the fluence F(x, y) effective during ablation on the surface is obtained as $$F(x,y)=F_P(x,y)\cdot\cos\theta(x,y) \tag{13}$$

wherein $F_P(x,y)$ designates the fluence for vertical incidence of the laser beam 3 on the surface, i.e. at an angle θ=0. Therefore, $F_P$ corresponds to the fluence or the beam profile of the laser beam 3.

The second effect taken into consideration is that the effective fluence varies in accordance with the intensity or energy profile of the pulses in a plane orthogonal to the direction of the laser beam 3 and that it may thereby, in particular, also be below the threshold value $F_{thr}$.

Thus, the actual single-pulse ablation volume results from the following formula:

$$V_{pulse} = \iint_{Spot} D_P(x, y)dxdy \qquad (14)$$

$$= \mu \iint_{Spot} \ln\frac{F(x, y)}{F_{thr}} dxdy$$

$$= \mu \iint_{Spot} \ln\frac{F_P(x, y)\cos\theta(x, y)}{F_{thr}} dxdy.$$

Therefore, the single-pulse ablation volume non-linearly depends on the angle of inclination of the surface and on the fluence profile $F_P(x,y)$.

In the case of known single-pulse ablation volumes, an ablation program can be generated by known, simple generating methods, as described, for example, in DE 19727573 C1 or EP 1060710 A2, according to which ablation program the mean ablation depth $D_M$ results, in a uniformly or slowly varying manner, for a distance d of laser beam pulses directed onto the surface according to $$D_M = c\frac{V_{pulse}}{d^2} \qquad (15)$$

In this case, c is a proportionality factor resulting from the pattern of the points of incidence of the laser beam's pulses. For example, an approximately square pattern yields c=1, whereas an approximately hexagonal pattern yields c=2/√3.

In the following, it will be assumed that the ablation profile as well as the water content slowly changes in space with respect to the site of the distance d, or that the inclination slowly changes with respect to the diameter of the laser beam 3 on the surface. In order to describe the spatial dependence of these spatially slowly changeable parameters, coordinates u and v will be used in the following, which are given in a u-v coordinate system that coincides with the x-y coordinate system. Thus, the single-pulse ablation volume and, likewise, the mean depth $D_M$ resulting from the pulses placed next to each other are to be understood as a function of u and v.

The effective ablation depth then results from $$D_{M,lst}(u, v) = c\frac{V_{pulse,lst}(u, v)\cos\theta(u, v)}{d^2} \qquad (16)$$

Now, it is only required to substitute $D_{M,lst}$ for $D_{P,W}$ in formula (9), wherein $V_{pulse,lst}$ is determined using formula (14) in which $D_P$ is replaced by $D_{P,W}$.

Thus, for all of the different surface regions to be ablated one respective value of the beam-dependent and/or inclination-dependent modification function as a function of at least the beam profile shape and/or the surface inclination in the respective region, and a value of the water content-dependent modification function is determined, as well as determining the pre-compensated desired ablation profile by the use of the desired ablation profile and of the values of the modification functions, in particular the product of the modification functions.

In order to determine the locations onto which the laser pulses are to be emitted, various known methods can be used, e.g. the methods already mentioned above and described in DE 19727573 C1 and EP 1060710 A2. In DE 19727573 C1, ablation is effected in layers, i.e. locations of impingement or target locations are determined in a layer-wise fashion for pulses, with the desired profile then resulting from superposition of these layers. According to the method in EP 1060710 A2, the spot distance is varied in a quasi-continuous manner in order to achieve the desired ablation depth.

The calculation of the modification function is explained using as an example the ablation of a spherical surface by a laser beam having a Gauss-shaped beam profile (cf. FIG. 3).

The beam profile or fluence is described by the formula $$F_P(r) = F_0 e^{-\frac{r^2}{w^2}} \qquad (17)$$

wherein $F_0$ is the peak fluence value, r is the radial distance from the center of the beam profile, and w is the distance after the profile has dropped to 1/e relative to the value at the center.

For the actual ablation profile of a laser pulse impinging orthogonally on a planar surface, this results in:

$$D_{lst}(r) = \mu\ln\frac{F_0}{F_{thr}} - \mu\frac{r^2}{w^2}, \qquad (18)$$

so that the single-pulse ablation volume for this pulse is calculated as $$V_{pulse,E} = \frac{\pi}{2}\mu(H)w^2\left[\ln\frac{F_0}{F_{thr}}\right]^2. \qquad (19)$$

As the mean depth of the desired profile for a square pattern of the points of impingement of the pulses, or spot pattern, having an edge length a, a mean depth of ablation according to $$D_E(r) = \frac{V_{s,E}}{d^2} = \frac{\pi}{2}\mu\frac{w^2}{d^2}\left[\ln\frac{F_0}{F_{thr}}\right]^2 \qquad (20)$$

can be expected. If $D_E$ were assumed to be equal to $D_{Soll}$, d could be determined as a function of the location.

However, the spherical surface is actually inclined, except at the center, with respect to the laser beam 3 that is assumed to impinge parallel to the z-axis with sufficiently good approximation. As is evident from FIG. 3, the angle of inclination can be calculated in the following manner as a function of the distance ρ of a location on the surface of the eye 2:

$$\theta(\rho) = \arcsin\left(\frac{-\rho}{R}\right) = \arctan\left(\frac{-\rho}{\sqrt{R^2-\rho^2}}\right). \qquad (21)$$

The inclination of the surface at the location ρ then has the effect that both the spot distance in the direction of inclination and the spot width w in the direction of inclination are increased by the factor $1/\cos(\theta(\rho))$. Therefore, the ratio w/d in the equation for D does not change with the inclination. However, the fluence does change in this equation. Further, μ now depends on the water content H, for example according to the equations (6) and (7). Therefore, the following result is obtained for the depth profile to be expected on the spherical surface:

$$D_{M,lst}(\rho) = c\frac{V_{pulse,lst}(\rho)\cos\theta(\rho)}{d^2} \quad (22)$$
$$= c\frac{\pi}{2}\mu(H)\frac{w^2}{d^2}\left[\ln\frac{F_0 \cdot \cos\theta(\rho)}{F_{thr}}\right]^2$$

This result may be systematically obtained also by assuming $\cos(\theta)$ and $\mu=\mu(H)$ to be constant over the spot area in the formula for the single-pulse ablation volume.

Figure 19:
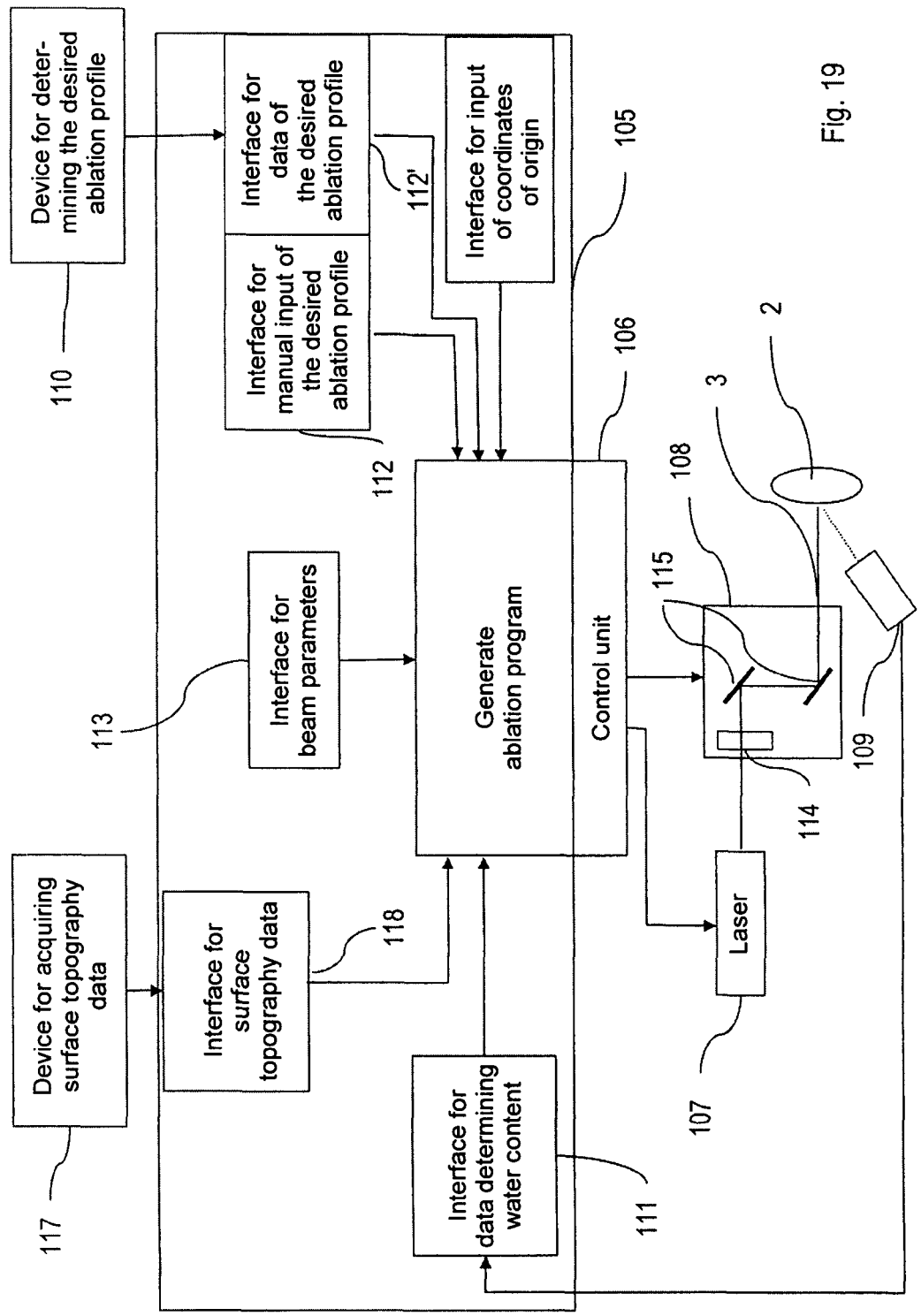
FIG. 19 shows a block diagram of an ablation device and a signal-forming device according to a further preferred embodiment of the second aspect of the invention.

FIG. 19 shows a laser ablation device comprising a generating device or a control signal-forming device according to a further preferred embodiment of the invention, which differs from the laser ablation device of the first exemplary embodiment according to the invention's second aspect in that the data processing device 105 is replaced by a data processing device 105' and that a device 117 for acquiring the surface topography of the eye 2 is provided, which device is connected, via a data link, to an interface of the data processing device 105' for the input of surface topography data to the data processing device 105'. Control commands for acquisition of surface topography data can also be output to the device 117 via this interface. The other components are unchanged so that the same reference numerals are used for them, and the statements made in the exemplary embodiment with respect to these components accordingly apply here as well.

In the example, the device 117 for acquisition of the surface topography of the eye may comprise an optical coherence tomograph.

The data processing device 105' differs from the data processing device 105 only by the interface 118 and the computer program used to program the data processing device 105' or its processor. The computer program comprises program code so that, during execution of the computer program in the data processing device 105', the method described below is carried out.

Figure 20:
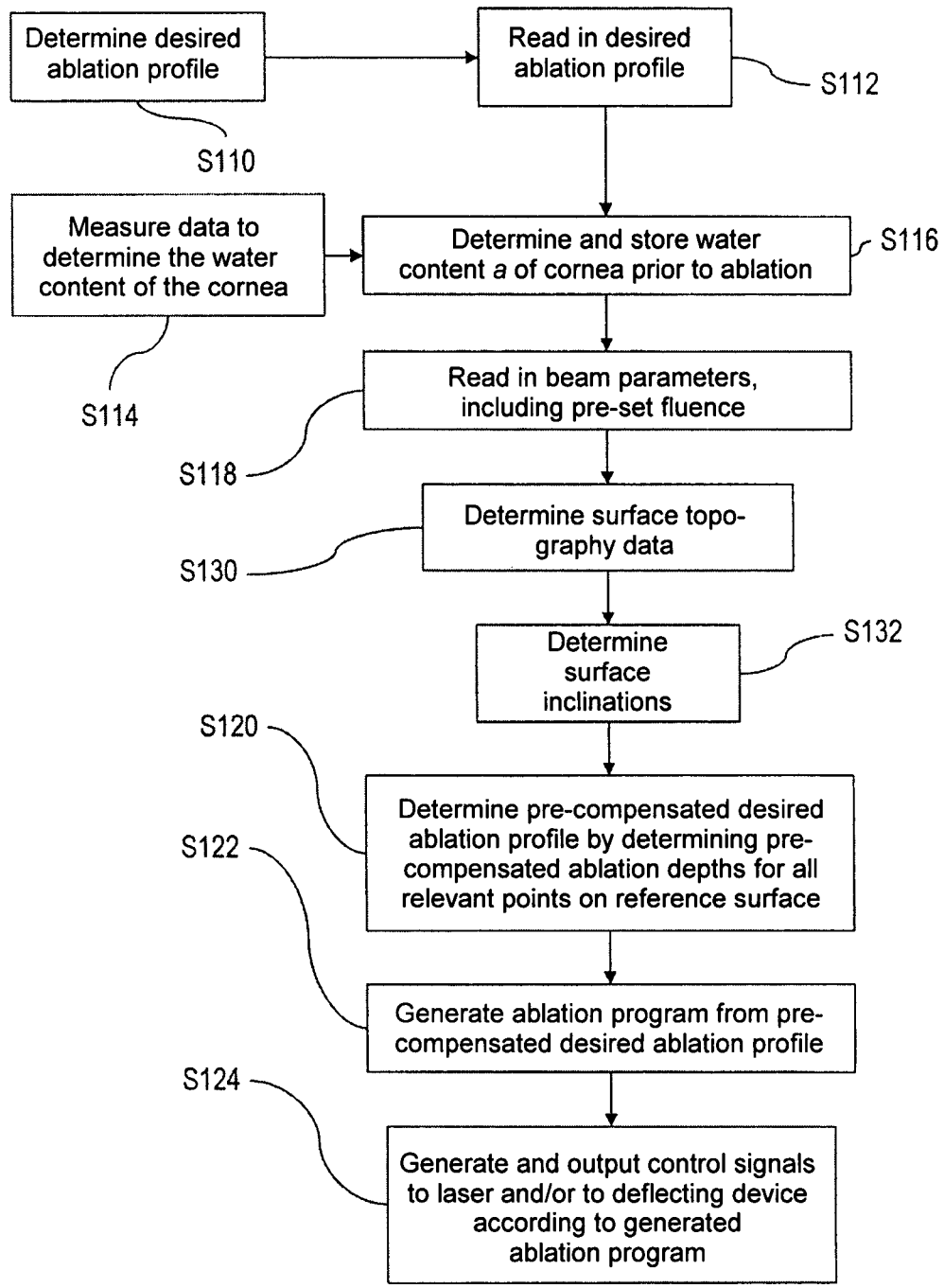
FIG. 20 shows a flow scheme of a method for forming and emitting control signals according to an ablation program generated by said method according to the further preferred embodiment of the second aspect of the invention in the second variant.

In order to determine the ablation program and to form and emit the control signal, the method steps schematically shown in the flow scheme of FIG. 20 are carried out, among which the steps designated by the same reference numerals as in FIG. 15 are carried out as in the first exemplary embodiment of the invention's second aspect, and the explanations pertaining to those steps also apply here accordingly.

Thus, in steps S110 and S112 or S114 and S116, respectively, data relating to the desired ablation profile or to the water content of the corneal tissue, respectively, are determined and stored prior to ablation.

In step S118, which follows then, a beam radius w and a pre-set fluence value $F_0$ are input, the latter being the peak value of fluence over the Gaussian beam profile of the laser 107. The shape of the beam profile is taken into consideration through the formulae used.

Then, in the next step S130, controlled by the data processing device 105', the surface topography of the region to be treated is determined by means of the device 117 for acquiring the surface topography data. For example, the corresponding data may comprise heights of the surface with respect to the x-y plane, said heights being detected above a grid of points in the x-y plane.

In step S132, these data are then read into the data processing device 105 via the interface 118' for the surface topography data. Surface inclinations are then determined from the height data by numerical determinations of gradients, as well as determining the above-indicated formula for the angle of inclination. The corresponding data are then stored in the memory of the data processing device 105'.

The next steps then correspond to the steps of the method in the first exemplary embodiment, although $N_{W,i}$ is now determined using formula (22) for $D_{P,W}$ in equation (8).

In this way, a pre-compensation takes place both with respect to the water content as well as the inclination of the surface and the shape of the beam profile such that their influences, which are neglected when generating the ablation program by a simple generating method, are taken into consideration in advance in a compensating or pre-compensating manner, and the actual ablation profile comes very close to the desired ablation profile.

The ablation method is suitable for both photorefractive keratectomy and LASIK. Since these methods involve the removal of material in different layers of the eye, the use of different desired ablation profiles may be accordingly required in some cases.

The coherence tomograph of the device 117 may further be used to determine the thickness of the cornea before and/or during ablation, i.e. to effect a pachymetric measurement. In particular, this allows to prevent the residual thickness of the cornea being below a predetermined minimum value.

In another exemplary embodiment, a temperature measuring device, e.g. an infrared camera whose optical axis is inclined at a sharp angle to the direction of the laser beam 3, may be used instead of the device 109 for carrying out confocal Raman spectroscopy. Said camera acquires data from which the temperature of the cornea and, thereby, its water content can be determined in a spatially resolved manner.

As an alternative, an optical coherence tomograph allowing to acquire data which allow the refractive index of the corneal tissue to be calculated can be used instead of the device 109 for carrying out confocal Raman spectroscopy. The water content can then be determined in turn from the refractive index data by means of the data processing device 105. The coherence tomograph may be present in addition to a coherence tomograph for determining the surface topography, if the latter tomograph is provided. However, it is also possible to use the same coherence tomograph for both functions. The coherence tomograph may further be used to determine the thickness of the cornea before and/or during ablation, i.e. to effect a pachymetric measurement. In particular, this allows to prevent the residual thickness of the cornea being below a predetermined minimum value.

Further, a device for determining the air humidity in the region of the cornea may be provided, which device transmits humidity data via a data link to the data processing device 105, where it can be included in the model for the ablation depth.

In further exemplary embodiments, the repetition frequency at which the pulses are emitted onto the material or the cornea, respectively, can also be modified as a function of the water content.

The invention claimed is:

1. A computer implemented method of generating an ablation control program to control emission of a pulsed laser energy beam from a laser to accomplish ablation of material from a surface of a body by application of the pulsed laser energy, comprising:
predetermining a predetermined desired ablation profile which indicates ablation depth as a function of a location on the surface of the body or which indicates ablation depth as a function of a direction of the laser beam with respect to the body;
modifying the predetermined desired ablation profile as a function of a beam profile of the laser beam, the beam profile being a course of intensity or of surface area related energy or fluence of a pulse of laser energy over a beam cross section near the surface of the body, and also as a function of an inclination of the surface of the body to be ablated to create a pre-compensated desired ablation profile that is based on the energy distribution across the beam profile and the inclination of the surface at a respective target location on the surface; and then, generating the ablation control program based on the pre-compensated desired ablation profile following the modification of the predetermined desired ablation profile;

wherein the ablation control program comprises at least one of a series of target locations related to the surface of the body or target directions onto or into which the pulsed laser energy beam is to be applied.

2. The method as claimed in claim 1, wherein generating the ablation control program further comprises determining a preliminary ablation program from the desired ablation profile;

using the preliminary ablation program to predict a predicted ablation profile as a function of an energy distribution across the beam profile and of the inclination of the surface; and generating the ablation program to be used using the predicted ablation profile;

determining the predicted ablation profile utilizing at least two locations which are spaced apart from each other by one tenth or less than one tenth of the diameter of the laser beam on the surface of the body;

using the predicted ablation profile and the predetermined desired ablation profile to determine a pre-compensated desired ablation profile; and generating the ablation program to be used from the pre-compensated desired ablation profile.

3. The method as claimed in claim 2, further comprising generating the ablation program to be used in an iterative manner such that, in an actual iteration step, a preliminary ablation program is determined from a modified desired ablation profile determined in a preceding iteration step, an actual predicted ablation profile is predicted on the basis of the preliminary ablation program as a function of an energy distribution across the beam profile and of the inclination of the surface, an actual modified desired ablation profile is determined using the actual predicted ablation profile, and the ablation program to be used is generated as a function of the predetermined desired ablation profile and at least one of the modified desired ablation profiles after the last iteration loop.

4. The method as claimed in claim 1, further comprising using a model by which a course of ablation depth can be predicted for a pulse as a function of the energy distribution across the beam profile or measuring the beam profile to generate the ablation program, the model comprising a representation of an entire volume ablated by the pulse or comprising a local representation of ablation depth as a function of fluence at an ablated location at a resolution greater than the beam cross section.

5. The method as claimed in claim 1, further comprising:
effecting pre-compensation as a function of an ablation property of the material, the property being dependent on the individual body; and/or;
effecting pre-compensation as a function of a change in surface and/or material properties expected during and/or as a result of ablation.

6. The method as claimed in claim 1, wherein generating the ablation program further comprises acquiring topographical data of the surface in addition to the inclination of the surface, wherein the topographical data is acquired by Placido ring methods or devices, strip projection methods or devices or from optical coherence tomography.

7. The method as claimed in claim 1, wherein the material to be ablated has a water content, and further comprising:
measuring the water content of the material;
using the measured water content of the material along with the desired ablation profile to generate the ablation program; and
guiding the laser beam over the surface during the ablation to be effected based on the ablation program.

8. The method as claimed in claim 7, wherein generation of the ablation program further comprises taking into account the water content as a function of the location on the surface or as a function of the location in a region to be ablated.

9. The method as claimed in claim 7, wherein taking into account the water content further comprises utilizing a further model that correlates, for a predetermined region of the material, the influence that pulses of the pulsed laser beam impinging on the predetermined region or on adjacent regions have on the water content of the predetermined region.

10. The method as claimed in claim 7, further comprising utilizing a model for the water content or change in the water content of the material as a function of at least the number and/or the position of pulses previously emitted onto the same location and/or adjacent locations in order to take the water content into consideration when generating the ablation program.

11. The method as claimed in claim 7, wherein measuring the water content of the material further comprises measuring a temperature of the surface.

12. The method as claimed in claim 7, wherein taking into account the water content further comprises determining from the predetermined desired ablation profile a pre-compensated ablation profile as a function of the water content and generating the ablation program from the pre-compensated ablation profile.

13. The method as claimed in claim 12, wherein determining the pre-compensated ablation profile further comprises utilizing a modification function, said modification function depending explicitly or implicitly on the water content of the material to be ablated and wherein a value of the modification function at a respectively predetermined location depends on a desired ablation depth given by the desired ablation profile at said location.

14. The method as claimed in claim 7 further comprising generating a preliminary ablation program from the desired ablation profile and, to establish the ablation program to be generated as a function of the water content, modifying at least a fluence value implicitly or explicitly given by the preliminary ablation program, or modifying a pulse energy of a pulse to be emitted onto the target location given by the ablation program, the pulse energy being implicitly or explicitly given by the preliminary ablation program, as a function of the water content at the target location and being assigned to the target location as an indication.

15. The method as claimed in claim 7, wherein in order to consider at least one of the following: the energy distribution across the beam profile, the inclination of the surface, the method further comprises:
determining a desired ablation profile, which is pre-compensated with respect to the influences of the energy distribution across beam profile or of the inclination of the surface, respectively, from the desired ablation profile, using a modification function which depends on the energy distribution across the beam profile or on the inclination of the surface, respectively; and generating the ablation program from the determined desired ablation profile which has been pre-compensated with respect to the influences of the energy distribution across the beam profile or of the inclination of the surface, respectively.

16. The method as claimed in claims 15 and 13, further comprising:
determining for at least two regions to be ablated from the surface one value each of the beam-dependent and/or inclination-dependent modification function as a function of at least the energy distribution across the beam profile and/or the inclination of the surface in the respective region, and
determining a value of a water content-dependent modification function, and
determining the pre-compensated desired ablation profile using the desired ablation profile and the values of the modification functions, including the modification functions' product.

17. The method as claimed in claim 7, wherein measuring the water content of the material further comprises measuring optical radiation that is returned from or arises from the material in the region to be ablated from the body.

18. The method as claimed in claim 17, further comprising performing confocal Raman spectroscopy of the optical radiation that is returned from or arises from the material, receiving fluorescent radiation that is returned from or arises from the material, or measuring refractive index of the material based on the optical radiation that is returned from or arises from the material.

19. A device for generating an ablation program for ablation of material from a surface according to a desired ablation profile by emission of pulses of a pulsed laser beam onto the surface, said device comprising a data processing device which is provided to carry out a generating method as claimed in claim 1.

20. The device as claimed in claim 19, comprising a control unit by means of at least one of the following can be controlled: a laser to emit the laser beam, a deflecting device to deflect the laser beam according to a generated ablation program, and a modulator attenuating the laser beam.

21. The device as claimed in claim 19, wherein the data processing device comprises at least one of the following: an interface for input of data which characterize the shape of the beam profile of the laser beam, a device for detection of the beam profile of the laser beam and a device for acquisition of topographical data of the surface to be ablated.

22. A device for ablation of material from a surface of a body, said device comprising a laser for emission of a pulsed laser beam, a deflecting device for controlled deflection of the laser beam, and a generating device as claimed in claim 19.

23. A computer implemented method of generating an ablation control program to control emission of pulsed laser energy from a laser to accomplish ablation of material from a surface of a body by application of the pulsed laser energy, comprising:
predetermining a predetermined desired ablation profile which indicates ablation depth as a function of a location on the surface of the body or which indicates ablation depth as a function of a direction of the laser beam with respect to the body;
modifying the predetermined desired ablation profile as a function of a beam profile of the laser beam, the beam profile being a course of intensity or of surface area related energy or fluence of a pulse of laser energy over a beam cross section near the surface of the body, and also as a function of an inclination of the surface of the body to be ablated;
using the desired ablation profile to determine a pre-compensated desired ablation profile based on the energy distribution across the beam profile and the inclination of the surface at a respective target location on the surface; and
generating the ablation control program based on the pre-compensated desired ablation profile following the modification of the predetermined desired ablation profile;
wherein determining the desired ablation profile further comprises determining one value of a modification function for each of at least two regions to be ablated from the surface as a function of the energy distribution across the beam profile and the inclination of the surface in the respective region; and
determining the pre-compensated desired ablation profile using the desired ablation profile and the values of the modification function;
wherein the ablation control program comprises at least one of a series of target locations related to the surface of the body or target directions onto or into which the pulsed laser energy beam is to be applied.

24. The method as claimed in claim 23, wherein determining the one value of the modification function further comprises taking into account intensity, energy or fluence of the pulses to be used for ablation.

25. A computer implemented method of generating an ablation control program to control emission of pulsed laser energy from a laser to accomplish ablation of material from a surface of a body by application of the pulsed laser energy, comprising:
predetermining a predetermined desired ablation profile which indicates ablation depth as a function of a location on the surface of the body or which indicates ablation depth as a function of a direction of the laser beam with respect to the body;
modifying the predetermined desired ablation profile as a function of a beam profile of the laser beam, the beam profile being a course of intensity or of surface area related energy or fluence of a pulse of laser energy over a beam cross section near the surface of the body, and as a function of an inclination of the surface of the body to be ablated;
using the desired ablation profile to determine a pre-compensated desired ablation profile based on the energy distribution across of the beam profile and the inclination of the surface at a respective target location on the surface;
wherein generating the ablation control program the further comprises determining a preliminary ablation program from the desired ablation profile; and
determining, for at least one of the pulses to be emitted, a desired value for energy or fluence depending on the energy distribution across of the beam profile, on the inclination of the surface at the region onto which the pulse is to be emitted, and on a prediction of the ablation depth using the preliminary ablation program, and
generating the ablation program such that the ablation program comprises the target location of the pulse according to the preliminary ablation program and determined ideal value for energy or fluence of the pulse;
wherein the ablation control program comprises at least one of a series of target locations related to the surface of the body or target directions onto or into which the pulsed laser energy beam is to be applied.

26. A method for ablation of material from a surface of a body, comprising:
generating an ablation control program to control emission of a pulsed laser energy beam from a laser by application of the pulsed laser energy, including:
predetermining a predetermined desired ablation profile which indicates ablation depth as a function of a location on the surface of the body or which indicates ablation depth as a function of a direction of the laser beam with respect to the body;
modifying the predetermined desired ablation profile as a function of a beam profile of the laser beam, the beam profile being a course of intensity or of surface area related energy or fluence of a pulse of laser energy over a beam cross section near the surface of the body, and as a function of an inclination of the surface of the body to be ablated to create a pre-compensated desired ablation profile that is based on the shape of the beam profile and the inclination of the surface at a respective target location on the surface; and
generating the ablation control program based on the pre-compensated desired ablation profile; and
guiding the pulsed laser energy beam over the surface to be ablated utilizing the ablation program generated;
wherein the ablation control program comprises at least one of a series of target locations related to the surface of the body or target directions onto or into which the pulsed laser energy beam is to be applied.

27. The method as claimed in claim 26, further comprising adjusting the fluence or energy of at least one laser pulse by either attenuating the laser beam or by controlling the laser to emit a beam having desired fluence or energy level.

28. The method as claimed in claim 27, further comprising determining the energy or fluence for at least two pulses during ablation as a function of the energy distribution across the beam profile and of the inclination of the surface in the region onto which the respective pulse is emitted.

29. A computer program comprising program code to carry out a method including:
predetermining a predetermined desired ablation profile which indicates ablation depth as a function of a location on the surface of the body or which indicates ablation depth as a function of a direction of the laser beam with respect to the body;
modifying the predetermined desired ablation profile as a function of a beam profile of the laser beam, the beam profile being a course of intensity or of surface area related energy or fluence of a pulse of laser energy over a beam cross section near the surface of the body, and as a function of an inclination of the surface of the body to be ablated to create a pre-compensated desired ablation profile that is based on the energy distribution across the beam profile and the inclination of the surface at a respective target location on the surface; and
generating the ablation control program based on the pre-compensated desired ablation profile when the program is being executed on a computer coupled to and operably controlling a pulsed laser energy beam from a laser to accomplish ablation of material from a surface of a body by application of the pulsed laser energy;
wherein the ablation control program comprises at least one of a series of target locations related to the surface of the body or target directions onto or into which the pulsed laser energy beam is to be applied.

30. A computer-readable data carrier including a computer program comprising program code to carry out a method including:
predetermining a predetermined desired ablation profile which indicates ablation depth as a function of a location on the surface of the body or which indicates ablation depth as a function of a direction of the laser beam with respect to the body;
modifying the predetermined desired ablation profile as a function of a beam profile of the laser beam, the beam profile being a course of intensity or of surface area related energy or fluence of a pulse of laser energy over a beam cross section near the surface of the body, and as a function of an inclination of the surface of the body to be ablated to create a pre-compensated desired ablation profile that is based on the energy distribution across the beam profile and the inclination of the surface at a respective target location on the surface; and
generating the ablation control program based on the pre-compensated desired ablation profile when the program is being executed on a computer;
wherein the ablation control program comprises at least one of a series of target locations related to the surface of the body or target directions onto or into which the pulsed laser energy beam is to be applied.

\* \* \* \* \*